United States Patent
Decicco et al.

(10) Patent No.: US 7,557,137 B2
(45) Date of Patent: Jul. 7, 2009

(54) GAMMA-LACTAMS AS BETA-SECRETASE INHIBITORS

(75) Inventors: Carl P. Decicco, New Hope, PA (US); Andrew J. Tebben, New Hope, PA (US); Lorin A. Thompson, III, Higganum, CT (US); Andrew P. Combs, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1044 days.

(21) Appl. No.: 10/634,078

(22) Filed: Aug. 4, 2003

(65) Prior Publication Data

US 2007/0265331 A1 Nov. 15, 2007

Related U.S. Application Data

(60) Provisional application No. 60/401,390, filed on Aug. 5, 2002.

(51) Int. Cl.
*A61K 31/40* (2006.01)
*A01N 43/36* (2006.01)

(52) U.S. Cl. ........................ 514/424; 514/426; 514/428; 514/429

(58) Field of Classification Search ................ 514/424, 514/426, 428, 429
See application file for complete search history.

(56) References Cited

U.S. PATENT DOCUMENTS

| 4,705,846 | A | 11/1987 | Thaisrivongs |
| 5,120,718 | A | 6/1992 | Goldman et al. |
| 5,164,388 | A | 11/1992 | De |
| 5,719,296 | A | 2/1998 | Acton, III et al. |

FOREIGN PATENT DOCUMENTS

| WO | WO 87/05909 | 10/1987 |
| WO | WO 90/04917 | 5/1990 |
| WO | WO 96/16950 | 6/1996 |
| WO | WO 97/16425 | 5/1997 |
| WO | WO 01/07407 | 2/2001 |

OTHER PUBLICATIONS

Chapman, P. F.; et al., *Nature Neurosci.* (1999), 2, 271-276.
Dahlgren, K. N.;. et al., *J. Biol. Chem.* (2002) 277, 32046-32053.
Gotz, J., et al., *Science* (2001) 293, 1491-1495.
Hussain, I. et al., *Mol. Cell. Neurosci.*, (1999) 14: 419-427.
Lewis, J.; et al., *Science* (2001), 293, 1487-1491.
Lin, X. et al., Proceedings of the National Academy of Sciences of the USA, (2000) 97: 1456-1460.
Luo, Y., et al., *Nature Neuroscience* (2001) 4: 231-232.
Martin, J. L. et al., *Biochemistry* (1999) 38: 7978-7988.
McLean, C. A., et al., *Ann. Neurol.* (1999) 46, 860-866.
Roberds, S.L. et al., *Human Molecular Genetics* (2001) 10: 1317-1324.
Seiffert, D.; et al., *J. Biol. Chem.* (2000) 275, 34086-34091.
Selkoe, D. J., *Physiol. Rev.* (2001) 81, 741-766.
Selkoe, D. J., *Ann. Rev. Cell Biol.* (1994) 10: 373-403.
Sinha, S., et al., *Nature (London)* (1999) 402: 537-540.
Thaisrivongs et al., *J. Hypertension* (1989), Suppl. (2), S21-S23.
Thaisrivongs, S. et al., *J. Med. Chem.* (1988) 31(7): 1369-1376.
Thal, D. R., et al., *J. Neuropath. Exp. Neuro.* (2002) 61: 82-293.
Vassar, R., et al., *Science (Washington, D. C.)* (1999) 286: 735-741.
Walsh, D. M., et al., *Nature* (2002) 416, 535-539.
Wolfe, M. S., *J. Med. Chem.* (2001) 44, 2039-2060.
Yan, R. et al., *Nature (London)* (1999) 402: 533-537.

*Primary Examiner*—Ardin Marschel
*Assistant Examiner*—Leslie A Royds
(74) *Attorney, Agent, or Firm*—John F. Levis; Aldo A. Algieri

(57) ABSTRACT

There is provided a series of novel substituted gamma-lactams of Formula (I)

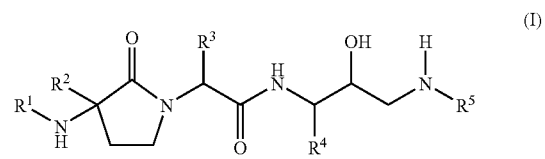

wherein $R^1$, $R^2$, $R^3$, $R^4$ and $R^5$ are defined herein, their pharmaceutical compositions and methods of use. These novel compounds inhibit the processing of amyloid precursor protein (APP) by β-secretase and, more specifically, inhibit the production of Aβ-peptide. The present invention is directed to compounds useful in the treatment of neurological disorders related to β-amyloid production, such as Alzheimer's disease and other conditions affected by anti-amyloid activity.

7 Claims, No Drawings

SEQUENCE LISTING

<160> NUMBER OF SEQ ID NOS: 1

<210> SEQ ID NO 1
<211> LENGTH: 9
<212> TYPE: PRT

```
<213> ORGANISM: Drosophila melanogaster
<220> FEATURE:
<221> NAME/KEY: MISC_FEATURE
<222> LOCATION: (1)..(1)
<223> OTHER INFORMATION: in which a chemical group is appended to the
      N-terminus of the peptide
<220> FEATURE:
<221> NAME/KEY: MISC_FEATURE
<222> LOCATION: (9)..(9)
<223> OTHER INFORMATION: wherein a chemical group is appended to the
      epsilon amino group of the C-terminal lysine side chain

<400> SEQUENCE: 1

Glu Val Asn Leu Asp Ala Glu Phe Lys
1               5
```

GAMMA-LACTAMS AS BETA-SECRETASE INHIBITORS

CROSS-REFERENCE TO RELATED APPLICATIONS

This is a non-provisional application which claims the benefit of U.S. Provisional Application No. 60/401,390 filed Aug. 5, 2002.

FIELD OF THE INVENTION

This invention provides novel substituted gamma-lactam compounds having drug and bio-affecting properties, their pharmaceutical compositions and method of use. In particular, the invention is concerned a series of novel gamma-lactams which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present invention relates to the treatment of Alzheimer's Disease (AD) and similar diseases.

BACKGROUND OF THE INVENTION

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.*, 1994, 10: 373-403).

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules.

Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

Multiple lines of evidence together strongly suggest that a reduction in brain Aβ levels will prevent the onset and progression of AD. First, Aβ is a major constituent of the parenchemyal plaques observed in all AD patients and the cerebral vasculature amyloid deposits observed in 90% AD patients (reviewed in Selkoe, D. *Physiol. Rev.* 2001, 81, 741-766; Wolfe, M. *J. Med. Chem.* 2001, 44, 2039-2060). These plaques are formed from the aggregation of soluble Aβ whose brain levels are highly correlated with the severity of AD neurodegeneration (McLean, C., Cherny, R. et al., *Ann. Neurol.* 1999, 46, 860-866). Second, mutations in three genes (APP, PS-1, or PS-2) that increase Aβ cause familial AD (FAD), where AD onset is accelerated by at least a decade. Included in the mutations that increase Aβ are chromosome 21 Trisomy that causes Down's syndrome. Third, transgenic mice that express one or more of the mutant FAD genes have increased Aβ levels, form parenchymal plaques and cerebral vascular deposits containing AD, exhibit memory deficits (Chapman, P.; White, G. et al., *Nature Neurosci.* 1999, 2, 271-276) and enhance neurofibrillary degeneration in mice that also overexpress mutant tau (Lewis, J.; Dickson, D. et al., *Science* 2001, 293, 1487-1491). Fourth, Aβ is toxic to cultured cells (Dahlgren, K.; Manelli, A. et al., *J. Biol. Chem.* 2002 277, 32046-32053), induces neurofibrillary tangles in mice with mutant tau (Gotz, J., Chen, F. et al., *Science* 2001, 293, 1491-1495) and interferes with long-term potentiation, a likely component of memory (Walsh, D., Klyubin, I. et al., *Nature* 2002, 416, 535-539 and references therein). Taken together, these data lead one skilled in the art to conclude that excess Aβ production and/or reduced Aβ clearance cause AD. From this it follows that reducing brain Aβ levels by inhibition of γ-secretase will prevent the onset and progression of AD.

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al., (1999) *Nature (London)*, 402: 537-540; Vassar, R., et al., (1999) *Science* (Washington, D.C.), 286: 735-741; Walsh, D. M. et al., (2002); Wolfe, M. S. (2001); Yan, R. et al., (1999) *Nature* (London), 402: 533-537].

Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324].

BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

Published article Martin, J. L. et al., (1999), *Biochemistry*, 38: 7978-7988 discloses macrocyclic inhibitors of the HIV 1 protease.

PCT Publication WO 96/16950, published Jun. 6, 1996, discloses macrocyclic inhibitors of the HIV 1 protease.

PCT Publication WO 01/07407, published Feb. 1, 2001, discloses lactam inhibitors of the hepatitis C virus NS3 protease.

PCT Publication WO 97/16425, published May 9, 1997, and related U.S. Pat. No. 5,719,296 disclose pseudolactam inhibitors of peptide binding to MHC class II receptors.

U.S. Pat. No. 5,120,718 to Goldman et al., granted Jun. 9, 1992, discloses candida acid protease inhibiting compounds.

PCT Publication WO 90/04917, published May 17, 1990, and related U.S. Pat. No. 5,164,388 discloses heterocyclic peptide renin inhibitors.

PCT Publication WO 87/05909, published Oct. 8, 1987, and related U.S. Pat. No. 4,705,846 disclose renin inhibitors having a lactam pseudo dipeptide insert.

Published article Thaisrivongs et al., *J. Hypertension* (1989), Suppl. (2), S21-S23 discusses related renin inhibitors.

Published article Thaisrivongs, S. et al., *J. Med. Chem.* (1988), 31(7): 1369-76 discusses related renin inhibitors.

U.S. Pat. No. 5,164,388 to De et al., granted Nov. 17, 1992, discloses heterocyclic renin inhibitors.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE INVENTION

A series of gamma-lactam derivatives having the Formula (I)

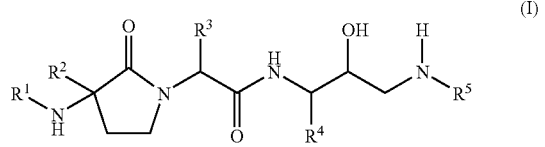

or a stereoisomer; or a pharmaceutically acceptable salt thereof, wherein $R^1$, $R^2$, $R^3$, $R^4$, and $R^5$ as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION OF THE INVENTION

The present invention comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

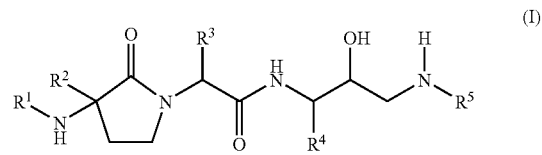

wherein $R^1$ is selected from the group consisting of —C(=O)$R^{1a}$, —S(=O)$R^{1a}$, —S(=O)$_2R^{1a}$, —C(=O)O$R^{1a}$, —C(=O)NH$R^{1a}$, and $C_1$-$C_6$ alkyl optionally substituted with $R^{1b}$;

$R^{1a}$ is $C_1$-$C_6$ alkyl optionally substituted with $R^{1b}$;

$R^{1b}$ is independently selected from the group consisting of halogen, —CF$_3$, —OCF$_3$, —CO$_2R^6$, —C(=O)NR$^6$R$^6$, —NR$^6$C(=O)R$^6$, —NR$^6$R$^6$, —NR$^6$SO$_2$R$^6$, —C(=O)R$^6$, —S(=O)R$^6$, —SO$_2$R$^6$, —SO$_2$NR$^6$R$^6$, —SR$^6$, —S(C$_1$-C$_4$ haloalkyl), —OR$^6$, —O(C$_1$-C$_4$ haloalkyl), —(C$_3$-C$_7$)cycloalkyl, -imidazole, -thiazole, -oxazole, —(C$_2$-C$_6$)alkenyl, and —(C$_2$-C$_6$)alkynyl;

$R^2$ is selected from the group consisting of C$_1$-C$_4$ alkyl, C$_2$-C$_4$ alkenyl, C$_2$-C$_4$ alkynyl, and C$_3$-C$_6$ cycloalkyl in which each group is optionally substituted with halogen, —CF$_3$, —OCF$_3$, —CH$_3$, —CH$_2$CH$_3$, —OCH$_3$, —OCH$_2$CH$_3$, or —(C$_3$-C$_7$)cycloalkyl;

$R^3$ is selected from the group consisting of C$_1$-C$_4$ alkyl, C$_2$-C$_4$ alkenyl, and C$_2$-C$_4$ alkynyl optionally substituted with $R^{3a}$, or phenyl optionally substituted with $R^{3b}$;

$R^{3a}$ is selected from the group consisting of $R^{3b}$, C$_3$-C$_6$ cycloalkyl optionally substituted with $R^{3b}$, phenyl optionally substituted with $R^{3b}$, and 3,4-methylenedioxyphenyl;

$R^{3b}$ is independently selected at each occurrence from the group consisting of halogen, —NO$_2$, —CN, —C$_1$-C$_4$alkyl, —OH, —OCH$_3$, —OCH$_2$CH$_3$, —CF$_3$, —OCF$_3$, —SCF$_3$, —C(=O)R$^6$, —NR$^6$C(=O)R$^6$, —NR$^6$SO$_2$R$^6$, —NR$^6$R$^6$, —OC(=O)NR$^6$R$^6$, —NR$^6$C(=O)NR$^6$R$^6$, —C(=O) NR$^6$R$^6$, —C(=O)OR$^6$, —SR$^6$, —S(=O)R$^6$, —S(=O)$_2$ R$^6$, and —S(=O)$_2$NR$^6$R$^6$;

$R^4$ is selected from the group consisting of C$_1$-C$_4$ alkyl, C$_2$-C$_4$ alkenyl, and C$_2$-C$_4$ alkynyl optionally substituted with $R^{4a}$;

$R^{4a}$ is selected from $R^{4b}$, or phenyl optionally substituted with $R^{4b}$;

$R^{4b}$ is selected from the group consisting of halogen, —NO$_2$, —CN, —NCS, —CH$_3$, —CH$_2$CH$_3$, —CH$_2$CH$_2$CH$_3$, —CH(CH$_3$)$_2$, —CF$_3$, —OCF$_3$, —SCF$_3$, —OH, —OCH$_3$, —OCH$_2$CH$_3$, —SH, —SCH$_3$, —SCH$_2$CH$_3$, —CO$_2$H, —CO$_2$CH$_3$, —CO$_2$CH$_2$CH$_3$, —NH$_2$, —NH(CH$_3$), —N(CH$_3$)$_2$, —C(═O)NH$_2$, —C(═O)NH(CH$_3$), —C(═O)N(CH$_3$)$_2$, —C(═O)H, —C(═O)CH$_3$, —NHC(═O)CH$_3$, and —NHSO$_2$CH$_3$;

$R^5$ is $C_1$-$C_{10}$ alkyl optionally substituted with $R^{5a}$;

$R^{5a}$ is selected from the group consisting of $R^{5b}$, $C_3$-$C_8$ cycloalkyl, $C_2$-$C_6$ alkenyl, $C_2$-$C_6$ alkynyl, and phenyl optionally substituted with $R^{5b}$;

$R^{5b}$ is selected from the group consisting of $R^6$, halogen, —CN, —CF$_3$, —NO$_2$, —NCS, —OCF$_3$, —CO$_2$H, —C(═O)H, —OR$^6$, —NR$^6$R$^6$, —OC(═O)NR$^6$R$^6$, —NR$^6$C(═O)NR$^6$R$^6$, —C(═O)NR$^6$R$^6$, —C(═O)OR$^6$, —SR$^6$, —S(═O)R$^6$, —S(═O)$_2$R$^6$, and —S(═O)$_2$NR$^6$R$^6$; and $R^6$ is independently selected at each occurrence from the group consisting of hydrogen, $C_1$-$C_6$ alkyl and phenyl.

The present invention also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, November 2001, 108 (9): 1243-1246; as well as PCT international patent application WO 01/92235, filed Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_1$-$C_6$ alkyl" and "$C_1$-$C_{10}$ alkyl" denotes alkyl having 1 to 6 or 1 to 10 carbon atoms. Examples of alkyl include, but are not limited to, methyl, ethyl, n-propyl, i-propyl, n-butyl, i-butyl, sec-butyl, t-butyl, pentyl, hexyl, octyl and decyl. Preferred "alkyl" group, unless otherwise specified, is "$C_1$-$C_4$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain. Examples of "$C_2$-$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_3$-$C_6$ cycloalkyl" and "$C_3$-$C_8$ cycloalkyl" denotes such as cyclopropyl, cyclobutyl, cyclopentyl, cyclohexyl, or cyclooctyl.

The compounds described herein may have asymmetric centers. An example of a preferred stereochemical configuration is the isomer:

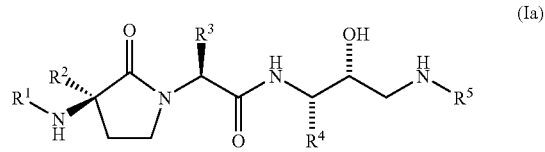

(Ia)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Additionally, the carbon atom to which $R^1NH$— and $R^2$ is attached may describe a chiral carbon. Compounds of the present invention containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present invention, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

In a preferred embodiment, the present invention provides for compounds of Formula (I)

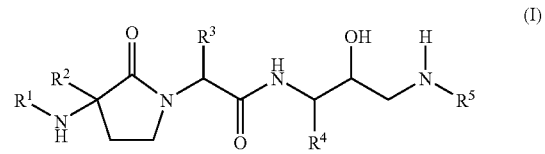

or a stereoisomer; or a pharmaceutically acceptable salt thereof, wherein $R^1$ is selected from the group consisting of —C(=O)$R^{1a}$, —S(=O)$R^{1a}$, —S(=O)$_2R^{1a}$, —C(=O)O$R^{1a}$, and —C(=O)NH$R^{1a}$;

$R^{1a}$ is $C_1$-$C_6$ alkyl optionally substituted with $R^{1b}$;

$R^{1b}$ is independently selected from the group consisting of halogen, —CF$_3$, —OCF$_3$, —CO$_2R^6$, —C(=O)N$R^6R^6$, —N$R^6$C(=O)$R^6$, —N$R^6R^6$, —O$R^6$, —(C3-C7)cycloalkyl, -imidazole, -thiazole, -oxazole, —(C$_2$-C$_6$)alkenyl, and —(C$_2$-C$_6$)alkynyl;

$R^2$ is selected from the group consisting of $C_1$-$C_4$ alkyl, $C_2$-$C_4$ alkenyl, $C_2$-$C_4$ alkynyl, and $C_3$-$C_6$ cycloalkyl in which each group is optionally substituted with halogen, —CF$_3$, —OCF$_3$, —CH$_3$, —CH$_2$CH$_3$, —OCH$_3$, —OCH$_2$CH$_3$, or $C_3$-$C_7$ cycloalkyl;

$R^3$ is $C_1$-$C_4$ alkyl optionally substituted with $R^{3a}$;

$R^{3a}$ is selected from the group consisting of $R^{3b}$, $C_3$-$C_6$ cycloalkyl optionally substituted with $R^{3b}$, phenyl optionally substituted with $R^{3b}$, and 3,4-methylenedioxyphenyl;

$R^{3b}$ is independently selected at each occurrence from the group consisting of halogen, —NO$_2$, —CN, —$C_1$-$C_4$alkyl, —OH, —OCH$_3$, —OCH$_2$CH$_3$, —CF$_3$, —OCF$_3$, —SCF$_3$, —C(=O)$R^6$, —N$R^6$C(=O)$R^6$, —N$R^6$SO$_2R^6$, —N$R^6R^6$, —OC(=O)N$R^6R^6$, —N$R^6$C(=O)N$R^6R^6$, —C(=O)N$R^6R^6$, —C(=O)O$R^6$, —S$R^6$, —S(=O)$R^6$, —S(=O)$_2R^6$, and —S(=O)$_2$N$R^6R^6$;

$R^4$ is $C_1$-$C_4$ alkyl optionally substituted with $R^{4a}$;

$R^{4a}$ is $R^{4b}$ or phenyl optionally substituted with $R^{4b}$;

$R^{4b}$ is selected from the group consisting of halogen, —NO$_2$, —CN, —NCS, —CH$_3$, —CH$_2$CH$_3$, —CH$_2$CH$_2$CH$_3$, —CH(CH$_3$)$_2$, —CF$_3$, —OCF$_3$, —SCF$_3$, —OH, —OCH$_3$, —OCH$_2$CH$_3$, —SH, —SCH$_3$, —SCH$_2$CH$_3$, —CO$_2$H, —CO$_2$CH$_3$, —CO$_2$CH$_2$CH$_3$, —NH$_2$, —NH(CH$_3$), —N(CH$_3$)$_2$, —C(=O)NH$_2$, —C(=O)NH(CH$_3$), —C(=O)N(CH$_3$)$_2$, —C(=O)H, —C(=O)CH$_3$, —NHC(=O)CH$_3$, and —NHSO$_2$CH$_3$;

$R^5$ is $C_1$-$C_{10}$ alkyl optionally substituted with $R^{5a}$;

$R^{5a}$ is selected from the group consisting of $R^{5b}$, $C_3$-$C_8$ cycloalkyl, $C_2$-$C_6$ alkenyl, $C_2$-$C_6$ alkynyl optionally substituted with $R^{5b}$, and phenyl optionally substituted with $R^{5b}$;

$R^{5b}$ is selected from the group consisting of $R^6$, halogen, —CN, —CF$_3$, —NO$_2$, —NCS, —OCF$_3$, —CO$_2$H, —C(=O)H, —O$R^6$, —N$R^6R^6$, —OC(=O)N$R^6R^6$, —N$R^6$C(=O)N$R^6R^6$, —C(=O)N$R^6R^6$, —C(=O)O$R^6$, —S$R^6$, —S(=O)$R^6$, —S(=O)$_2R^6$, and —S(=O)$_2$N$R^6R^6$; and $R^6$ is independently selected at each occurrence from the group consisting of hydrogen, $C_1$-$C_6$ alkyl and phenyl.

In another preferred embodiment, the present invention provides compounds of Formula (I)

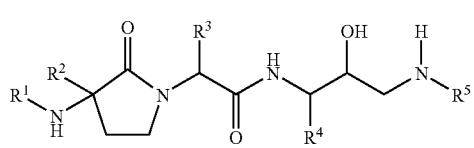
(I)

or a stereoisomer; or a pharmaceutically acceptable salt thereof, wherein
$R^1$ is selected from the group consisting of —C(=O)$R^{1a}$, —S(=O)$R^{1a}$, —S(=O)$_2$$R^{1a}$, —C(=O)O$R^{1a}$, and —C(=O)NH$R^{1a}$;
$R^{1a}$ is $C_1$-$C_6$ alkyl optionally substituted with $R^{1b}$;
$R^{1b}$ is independently selected from the group consisting of halogen, —CF$_3$, —OCF$_3$, —CO$_2$$R^6$, —C(=O)N$R^6$$R^6$, —N$R^6$C(=O)$R^6$, —N$R^6$$R^6$, —O$R^6$, —(C3-C7)cycloalkyl, -imidazole, -thiazole, -oxazole, —(C$_2$-C$_6$)alkenyl, and —C$_2$-C$_6$)alkynyl;
$R^2$ is selected from the group consisting of $C_1$-$C_4$ alkyl, $C_2$-$C_4$ alkenyl, $C_2$-$C_4$ alkynyl, and $C_3$-$C_6$ cycloalkyl in which each group is optionally substituted with halogen, —CF$_3$, —OCF$_3$, —CH$_3$, —CH$_2$CH$_3$, —OCH$_3$, —OCH$_2$CH$_3$, and $C_3$-$C_7$ cycloalkyl;
$R^3$ is $C_1$-$C_4$ alkyl optionally substituted with $R^{3a}$;
$R^{3a}$ is selected from the group consisting of $R^{3b}$, $C_3$-$C_6$ cycloalkyl optionally substituted with $R^{3b}$, phenyl optionally substituted with $R^{3b}$, and 3,4-methylenedioxyphenyl;
$R^{3b}$ is independently selected at each occurrence from the group consisting of halogen, —NO$_2$, —CN, —(C$_1$-C$_4$)alkyl, —CF$_3$, —OH, —OCH$_3$, —OCH$_2$CH$_3$, OCF$_3$, —SCF$_3$, —C(=O)$R^6$, —N$R^6$C(=O)$R^6$, —N$R^6$SO$_2$$R^6$, —N$R^6$$R^6$, —OC(=O)N$R^6$$R^6$, —N$R^6$C(=O)N$R^6$$R^6$, —C(=O)N$R^6$$R^6$, —C(=O)O$R^6$, —S$R^6$, —S(=O)$R^6$, —S(=O)$_2$$R^6$, and —S(=O)$_2$N$R^6$$R^6$;
$R^4$ is $C_1$-$C_4$ alkyl substituted with $R^{4a}$;
$R^{4a}$ is selected from the group consisting of

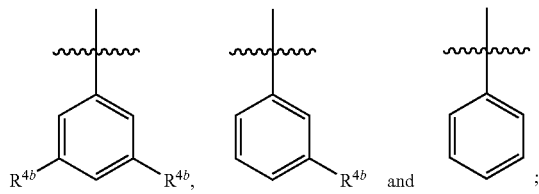

$R^{4b}$ is selected from the group consisting of F, Cl, Br, —CH$_3$, —CH$_2$CH$_3$, —CF$_3$, —OCF$_3$, —SCF$_3$, —OH, —OCH$_3$, —SH, —SCH$_3$, —CO$_2$H, —CO$_2$CH$_3$, —NH$_2$, —NH(CH$_3$), —N(CH$_3$)$_2$, —C(=O)NH$_2$, —C(=O)CH$_3$, and —NHC(=O)CH$_3$;
$R^5$ is $C_1$-$C_{10}$ alkyl optionally substituted with $R^{5a}$;
$R^{5a}$ is selected from the group consisting of $R^{5b}$, $C_3$-$C_8$ cycloalkyl optionally substituted with $R^{5b}$, $C_2$-$C_6$ alkynyl optionally substituted with $R^{5b}$, and phenyl optionally substituted with $R^{5b}$;
$R^{5b}$ is selected from the group consisting of $R^6$, halogen, —CN, —CF$_3$, —NO$_2$, —OCF$_3$, —CO$_2$H, —C(=O)H, —O$R^6$, —N$R^6$$R^6$, —OC(=O)N$R^6$$R^6$, —N$R^6$C(=O)N$R^6$$R^6$, —C(=O)N$R^6$$R^6$, —C(=O)O$R^6$, —S$R^6$, —S(=O)$R^6$, —S(=O)$_2$$R^6$, and —S(=O)$_2$N$R^6$$R^6$; and $R^6$ is independently selected at each occurrence from the group consisting of hydrogen, $C_1$-$C_6$ alkyl and phenyl.

In yet another preferred embodiment, the present invention provides compounds of Formula (I)

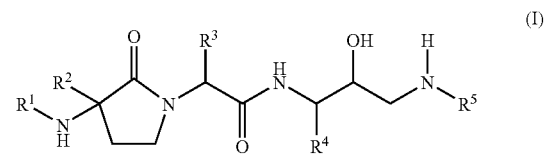
(I)

or a stereoisomer; or a pharmaceutically acceptable salt thereof, wherein
$R^1$ is selected from the group consisting of —C(=O)$R^{1a}$, —S(=O)$R^{1a}$, —S(=O)$_2$$R^{1a}$, —C(=O)O$R^{1a}$, and —C(=O)NH$R^{1a}$;
$R^{1a}$ is $C_1$-$C_6$ alkyl optionally substituted with $R^{1b}$;
$R^{1b}$ is independently selected from the group consisting of halogen, —CF$_3$, —OCF$_3$, —N$R^6$$R^6$, —O$R^6$, —(C$_3$-C$_7$) cycloalkyl, -imidazole, thiazole, and oxazole;
$R^2$ is selected from the group consisting of $C_1$-$C_4$ alkyl optionally substituted with halogen, —CF$_3$, —OCH$_3$, —OCH$_2$CH$_3$, or $C_3$-$C_7$ cycloalkyl;
$R^3$ is $C_1$-$C_4$ alkyl optionally substituted with $R^{3a}$;
$R^{3a}$ is selected from the group consisting of phenyl optionally substituted with $R^{3b}$, and 3,4-methylenedioxyphenyl;
$R^{3b}$ is independently selected at each occurrence from the group consisting of F, Cl, $R^6$, —CF$_3$, OH, —OCH$_3$, —OCH$_2$CH$_3$, and —N$R^6$$R^6$;
$R^4$ is $C_1$-$C_4$ alkyl substituted with $R^{4a}$;
$R^{4a}$ is selected from the group consisting of

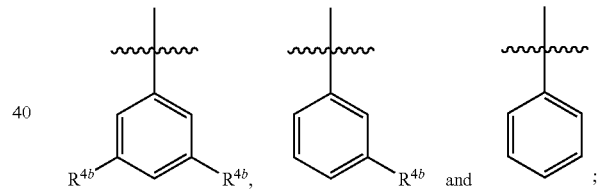

$R^{4b}$ is selected from the group consisting of F, Cl, Br, —CH$_3$, —CF$_3$, —OH, —OCH$_3$, —NH$_2$, —NH(CH$_3$), and —N(CH$_3$)$_2$;
$R^5$ is $C_1$-$C_2$ alkyl optionally substituted with $R^{5a}$;
$R^{5a}$ is selected from the group consisting of $R^{5b}$, $C_3$-$C_4$ cycloalkyl optionally substituted with $R^{5b}$, alkynyl, and phenyl optionally substituted with $R^{5b}$;
$R^{5b}$ is selected from the group consisting of $R^6$, F, Cl, —CN, —O$R^6$, and —N$R^6$$R^6$; and
$R^6$ is independently selected at each occurrence from the group consisting of hydrogen, $C_1$-$C_6$ alkyl and phenyl.

In still yet another preferred embodiment, the present invention provides stereoisomer compounds of Formula (Ia)

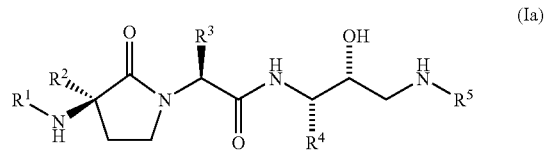
(Ia)

or a pharmaceutically acceptable salt thereof.

Preferred compounds for use in the method of the present invention include the compounds of Formula (I) listed below:

(2S)-2-(3(S)-Acetylamino-3-((S)-sec-butyl)-2-oxo-pyrrolidin-1-yl)-N-[(1S,2R)-1-(3,5-difluoro-benzyl)-2-hydroxy-3-(3-methoxy-benzylamino)-propyl]-4-phenyl-butyramide;

(2S)-2-(3(S)-Acetylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-Acetylamino-3(-cyclopropylmethyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-(2(S)-amino-5-carboxypentanoylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-(2-methoxy-acetylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-propionylamino-3-((S)-sec-butyl-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-ethoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-methoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-ethylureido-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-(3-hydroxypropionylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-(4-hydroxybutyrylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-acetylamino-3-(isobutyl)-2-oxo-pyrrolidin-1-yl)-N-[(1S,2R)-1-benzyl-2-hydroxy-3-(3-methoxy-benzylamino)-propyl]-4-phenyl-butyramide;

(2S)-2-(3(S)-acetylamino-3-((S)-sec-butyl)-2-oxo-pyrrolidin-1-yl)-N-[(1S,2R)-1-benzyl-2-hydroxy-3-(3-chloro-benzylamino)-propyl]-4-phenyl-butyramide;

(2S)-2-(3(S)-acetylamino-3-((S)-sec-butyl)-2-oxo-pyrrolidin-1-yl)-N-[(1S,2R)-1-benzyl-2-hydroxy-3-(propargylamino)-propyl]-4-phenyl-butyramide;

(2S)-2-(3(S)-acetylamino-3-((S)-sec-butyl)-2-oxo-pyrrolidin-1-yl)-N-[(1S,2R)-1-benzyl-2-hydroxy-3-(3,5-difluorobenzylamino)-propyl]-4-phenyl-butyramide;

(2S)-2-(3(S)-acetylamino-3-((S)-sec-butyl)-2-oxo-pyrrolidin-1-yl)-N-[(1S,2R)-1-benzyl-2-hydroxy-3-((3-trifluoromethylbenzyl)amino)-propyl]-4-phenyl-butyramide;

2-(3(S)-Acetylamino-3-((S)-isobutyl)-2-oxo-pyrrolidin-1-yl)-N-[(1S,2R)-1-benzyl-2-hydroxy-3-benzylamino-propyl]-4-phenyl-butyramide;

(2S)-2-(3(S)-acetylamino-3-((S)-sec-butyl)-2-oxo-pyrrolidin-1-yl)-N-[(1S,2R)-1-benzyl-2-hydroxy-3-(3-fluoro,5-(trifluoromethyl)benzylamino)-propyl]-4-phenyl-butyramide;

2-(3(S)-Acetylamino-3-(S)-isobutyl-2-oxo-pyrrolidin-1-yl)-N-[(1S,2R)-1-benzyl-3-(2-cyano-ethylamino)-2-hydroxy-propyl]-4-phenyl-butyramide;

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(2-methoxyphenyl)-butyramide;

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3,4-methylenedioxyphenyl)-butyramide;

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-fluorophenyl)-butyramide;

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(4-fluorophenyl)-butyramide; and (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-methoxyphenyl)-butyramide;

or a pharmaceutically acceptable salt thereof.

In another aspect, the present invention provides a pharmaceutical composition for the treatment of disorders responsive to the inhibition of β-amyloid peptide production comprising a therapeutically effective amount of Formula (I) in association with a pharmaceutically acceptable carrier or diluent.

In yet another aspect, the present invention provides a method for the treatment of a neurological disorder associated with β-amyloid production by β-secretase comprising administering to a host in need of such treatment a therapeutically effective amount of a compound of Formula (I).

In a preferred embodiment the neurological disorder associated with β-amyloid production by β-secretase is Alzheimer's disease, cerebral amyloid angiopathy and Down's Syndrome.

Thus, the present invention provides a method for inhibiting β-secretase activity comprising administering to a host in need of such inhibition a therapeutically effective amount of a compound of Formula (I) that inhibits β-secretase activity.

In still another aspect, the present invention provides for the use of a compound of Formula (I) for the manufacture of a medicament for the treatment of Alzheimer's disease.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, compounds of the invention represented by Formula I (General Reaction Scheme A) can be prepared by coupling, under standard conditions known to one skilled in the art, a substituted γ-lactam 2 and a substituted 2-hydroxy-1,3-diaminopropane 3. Methods for the synthesis of γ-lactams 2 are known in the art and are disclosed in a number of references including but not limited to those given below. Similarly, the synthesis of substituted 2-hydroxy-1,3-diaminopropanes 3 is known to one skilled in the art and is disclosed in a number of references including but not limited to those given below.

as sodium borohydride or derivatives thereof. The dipeptide precursor 5 is prepared by coupling a natural or unnatural amino acid ester 9 to a quaternary α-allyl amino acid 8, followed by oxidation of the allyl group to the requisite aldehyde and cyclization. Substituted 2-hydroxy-1,3-diaminopropanes 3 are prepared by reacting an amine with an epoxide 6 which is derived from an amino acid. Further details of the preparation of compounds of the invention are provided below.

Synthesis of a substituted quaternary α-allyl amino acid 8 is carried out according to one of several literature methods.

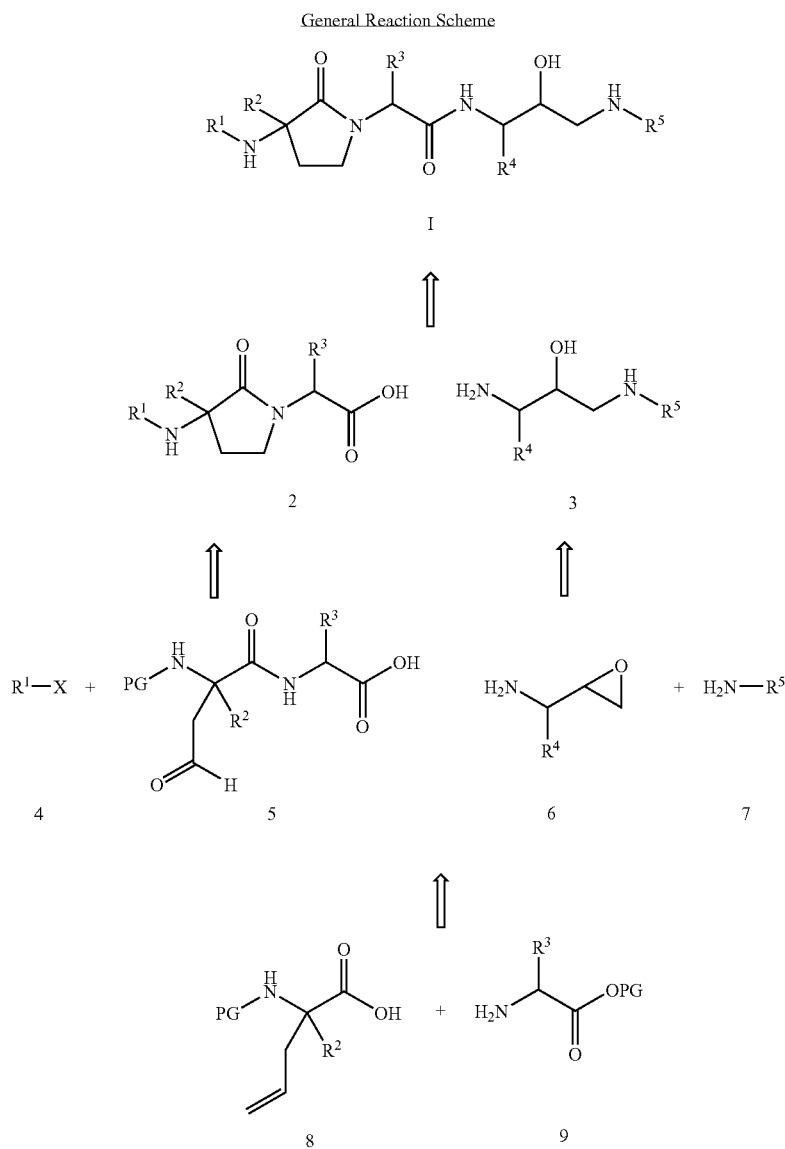

Substituted γ-lactams 2 can be prepared by cyclization of an aldehyde-containing dipeptide precursor 5 followed by deprotection of the amino group and functionalization with a suitable reaction partner 4, such as a carboxylic acid or an activated derivative thereof, a sulfonyl halide, isocyanate, or chloroformate. Alternatively, the amino group can be alkylated under standard conditions known to one skilled in the art, for example, using an aldehyde and a reducing agent such Scheme 1 shows the method of Seebach, et. al., (Seebach, D.; Hoffmann, M. *European Journal of Organic Chemistry* 1998, 1337-1351, Hoffmann, M.; Blank, S.; Seebach, D.; Kusters, E.; Schmid, E. *Chirality* 1998, 10, 217-222, Hoffmann, M.; Seebach, D. *Chimia* 1997, 51, 90-92, Blank, S.; Seebach, D. *Angew. Chem.* 1993, 105, 1780-1781 (See also Angew. Chem., Int. Ed. Engl., 1993, 1732(1712), 1765-1786), where (R)- or (S)-tert-butyl 2-tert-butyl-4-methoxy-2,5-dihydro-1, 3-imidazole-1-carboxylate (10) is alkylated sequentially with allyl iodide and a $R^2$-group eletrophile (which can be suitably protected by one skilled in the art if necessary) to provide a protected amino acid equivalent with high diastereoselectivity.

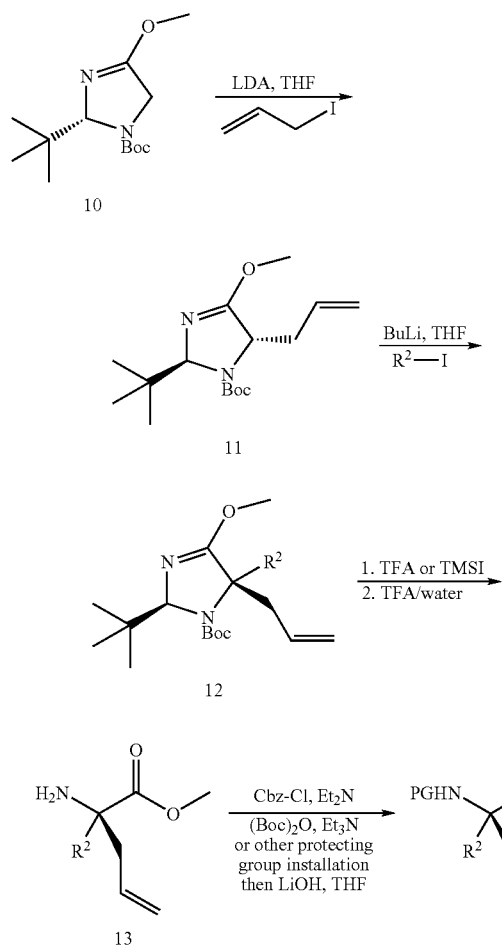

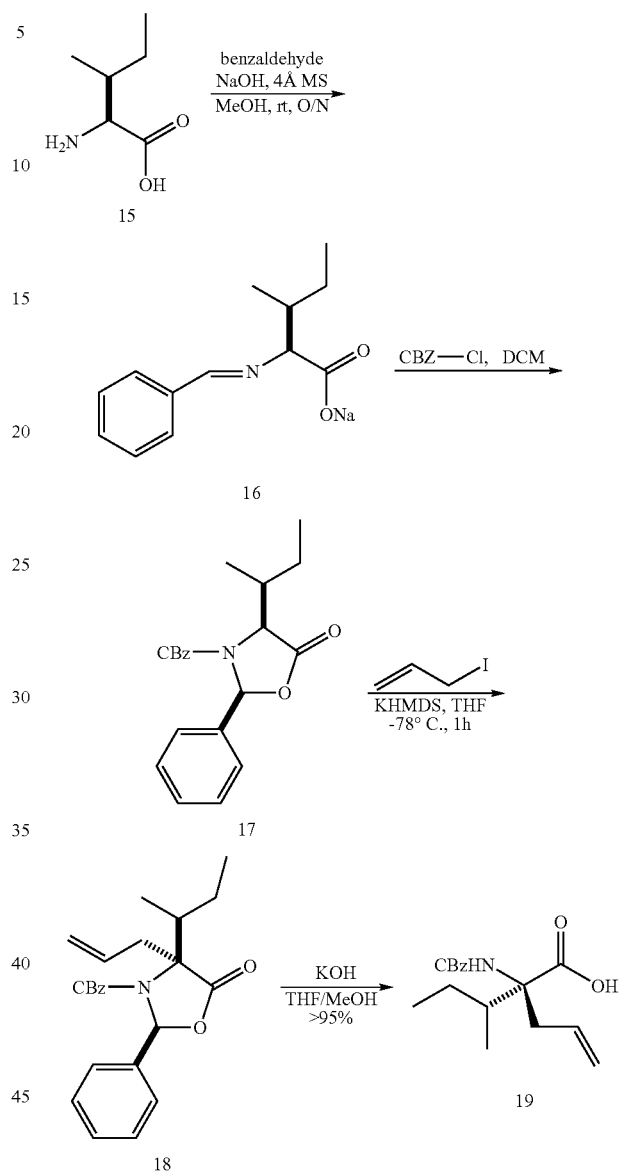

The scalemic amino acid is then regenerated by deprotection of the Boc group and acidic deprotection of the trimethylacetyl acetal., The resulting amino acid methyl ester (13) can then be protected under standard conditions with protecting groups well known to those skilled in the art, such as t-butyloxycarbonyl (Boc) or benzyloxycarbonyl (Cbz), and saponification provides the free carboxylic acid 14.

Alternatively, quaternary amino acids can be synthesized from the corresponding amino acid (Scheme 2). Using isoleucine as an example, formation of the benzylidene imine followed by cyclization with benzyloxycarbonyl chloride provides a protected amino acid precursor 17 (Seebach, D.; Fadel, A. *Helv. Chim. Acta.* 1985, 68, 1243 and Altmann, E.; Nebel, K.; Mutter, M. *Helv. Chim, Acta* 1991, 74, 800; De, B.; Dellaria, J. F.; Baker, W. R.; Zydowsky, T. M.; Rosenberg, S. H. et al., EP 365992, 1990). Alkylation with allyl bromide or iodide provides the alkylated lactone 18 which can be deprotected under basic conditions to provide the protected amino acid derivative 19 which can be directly coupled as is shown in Scheme 2.

An additional method for the preparation of quaternary amino acids is shown in Scheme 3. Treatment of an amino acid 20 with allyl bromide in the present of $Cs_2CO_3$ provides the amino acid allylic ester 21.

Ester enolate Claisen rearrangement of 21 results in 22 (Kazmaier, U. and Maier, S. *Tetrahedron* 1996, 52, 941).

Scheme 3

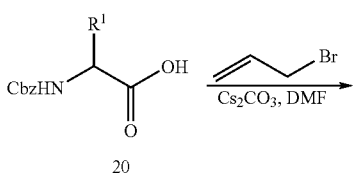

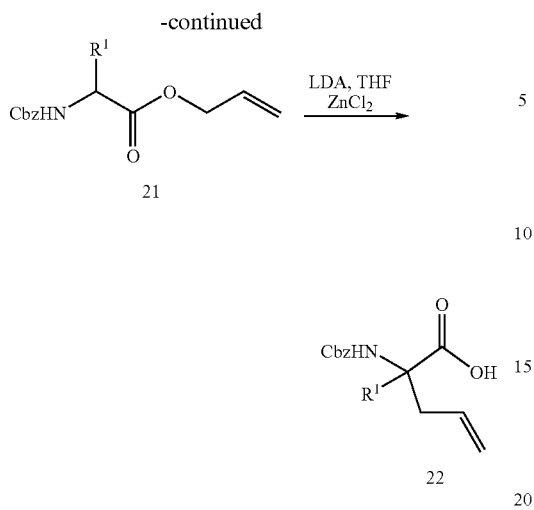

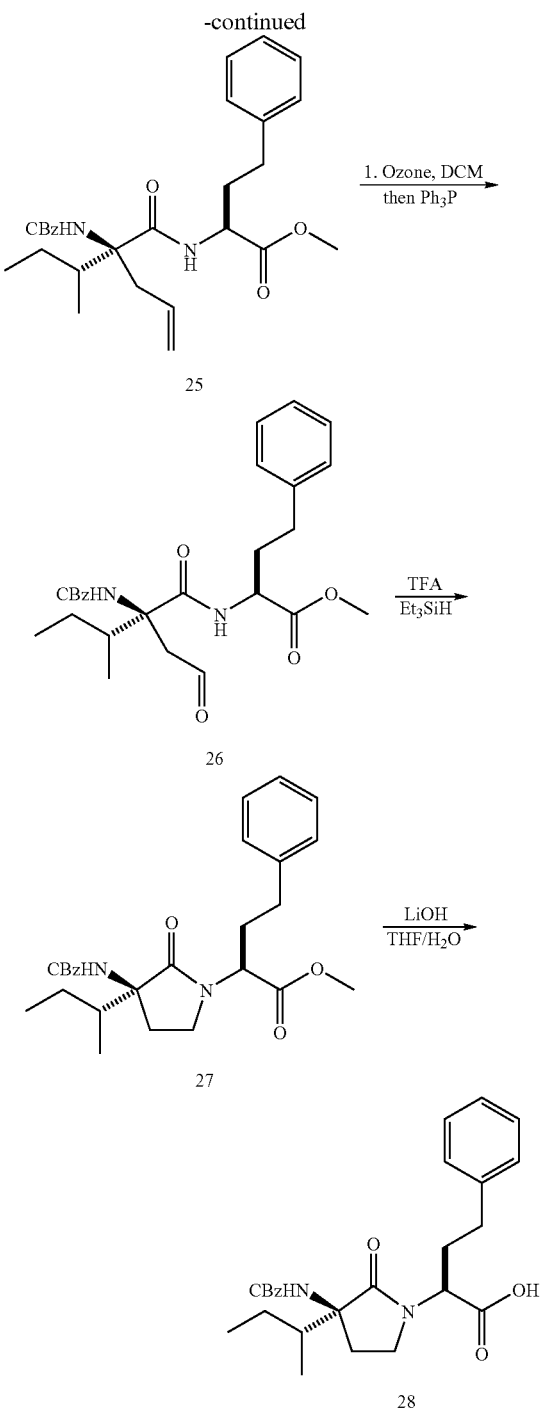

Amino acids used as the starting materials in the chemistry reported herein can be natural or unnatural. Many are available as items of commerce in suitably protected form, or unprotected where protecting groups can be installed under standard conditions to one skilled in the art. Additional methods for the preparation of unnatural amino include the Strecker synthesis or amidomalonate synthesis. In addition, the Myers pseudoephedrine glycinamide alkylation method (Myers, A. G.; Gleason, J. L.; Yoon, T.; Kung, D. W. *J. Am. Chem. Soc.* 1997, 119, 656-673), Schollkopf stereoselective alkylation (Schollkoft, U.; Hartwig, W.; Groth, U. *Angew. Chem. Int.* Ed. Engl. 1979, 18, 863), and Evans electrophilic azidation (Evans, D. A.; Britton, T. C.; Ellman, J. A.; Dorow, R. L. *J. Am. Chem. Soc.* 1990, 112, 4011) may be used to prepare natural or unnatural amino acids in enantionmerically pure form.

The quaternary amino acid 23 may then be coupled under standard conditions to a natural or unnatural amino acid ester using standard coupling reagents like HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) in the presence of a tertiary amine base such as triethylamine, N,N-diisopropyl-ethylamine, or N-methylmorpholine (Scheme 4). Oxidation of the allyl group using oxonolysis or osmium tetroxide/sodium periodate gives the aldehyde which is cyclized to the γ-lactam 27 using trietthylsilane and trifluoroacetic acid (Holladay, M. W.; Nadzan, A. M. *J. Org. Chem.* 1991, 56, 3900-3905; Duan, J. PCT International Publication WO 0059285, 2000.

Cleavage of the amino acid ester using saponification conditions such as lithium or sodium hydroxide in aqueous solution provides the protected lactam 28 for coupling to the diaminopropane fragment.

Lactams may also be synthesized in the manner demonstrated in Scheme 5, where the quaternary amino acid is directly oxidized to the aldehyde, and a second amino acid ester is introduced by reductive alkylation using a reducing agent such as sodium borohydrode, sodium triacetoxyborohydride, or sodium cyanoborohydride to produce an amine 32. The product can then be cyclized directly to form the Scheme 4

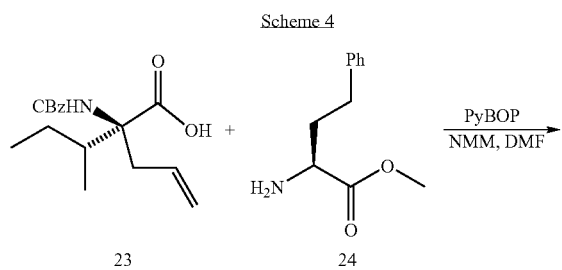

desired γ-lactam (see, for instance, Scheidt, K. A.; Roush, W. R.; McKerrow, J. H.; Selzer, P. M.; Hansell, E.; Rosenthal, P. J. *Bioorganic & Medicinal Chemistry* 1998, 6, 2477-2494.

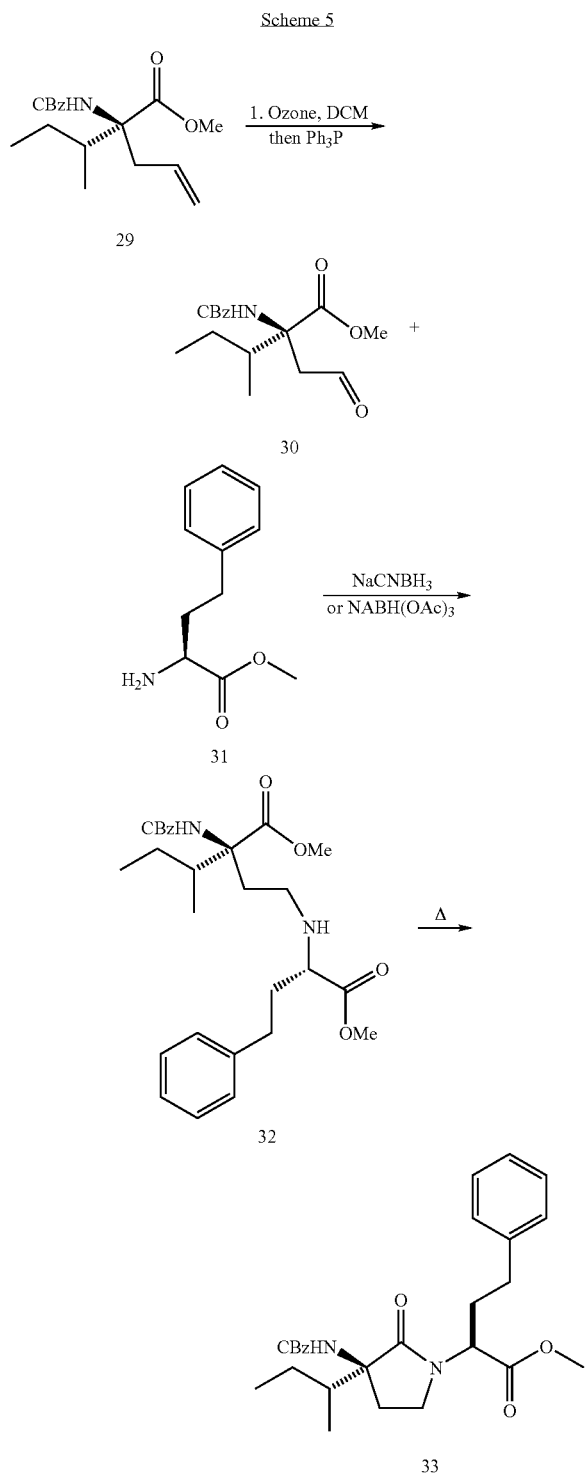

The lactam amine protecting group may now be removed by catalytic hydrogenation or other suitable methods (Scheme 6), and the primary amine center may be further functionalized by reacting with agents such as carboxylic acids or their activated variants such as acid chlorides or acid anhydrides to make amides such as 36. A number of other derivatives 36 can be prepared, including but not limited to the reaction with sulfonic acids or sulfonyl halides to prepare sulfonamides, chloroformates to provide carbamates, or carbamoyl chlorides or isocyanates to provide ureas. Saponification of the methyl ester of these derivatives provides the carboxylic acid 37 ready to couple to the diaminopropane fragment in protected or unprotected form.

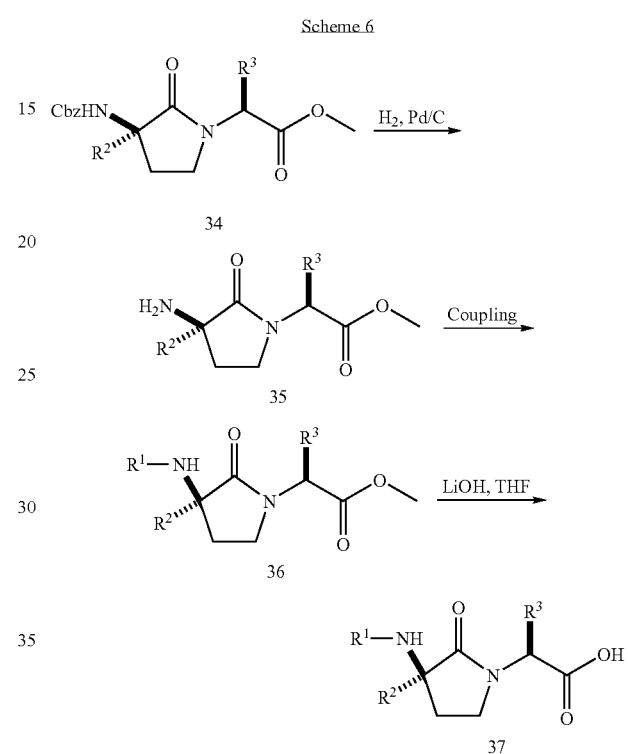

Scheme 7 discloses methods for preparing 2-hydroxy-1,3-diaminopropanes of type 43 that are used as a coupling partner to lactam acids 37. The starting materials for the process of preparing amino alcohols 43 in accordance with the present invention are activated esters represented by 38 wherein $R^4$ and $R^5$ are as defined above and X is Cl or a phenyl ester substituted in the ortho or para position on the phenyl ring by hydrogen, halogen or a nitro group. The compounds represented by formula 38 are commercially available or can be prepared by techniques well known to those of ordinary skill in the art. The protecting group on the amino function is preferably Boc or Cbz, but can also be other art recognized amino function protecting groups.

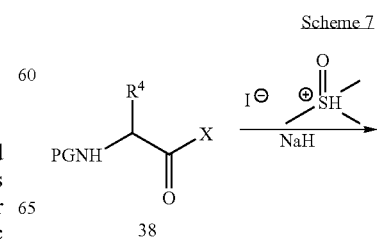

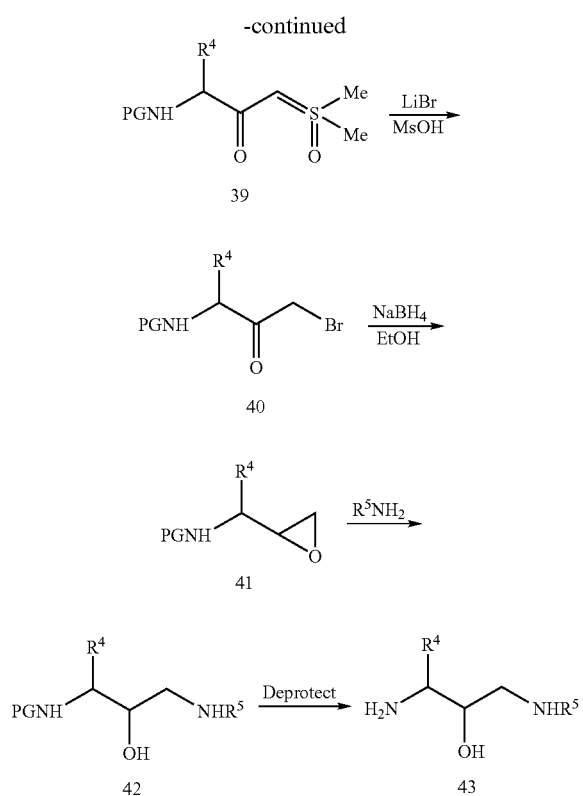

borohydride or aluminum hydride, most preferably sodium borohydride. The reaction is carried out in a protic solvent such as alcohol or water, most preferably in ethanol. The reaction is initiated at low temperature such as 0° C. to about 5° C. and as the reaction proceeds the temperature is elevated to about 25° C.

The epoxide 41 is then converted to amino alcohol 42 by reaction with an amine as defined above in a suitable polar solvent such as tetrahydrofuran, acetonitrile or alcohol. The reaction can be carried out with a Lewis acid additive such as lithium-based salts, titanium-based salts or aluminum-based salts. The reaction is carried out at a temperature range of 20-80° C.

The amine protecting group of compound 42 is then removed to give amine 43. The conditions for protecting group removal are dictated by the nature of the protecting group and are widely known to those skilled in the art. Optionally, the free amine intermediate 42 may be reacted with a suitable, orthogonal protecting group to provide a bis-protected intermediate (Scheme 8). Unmasking of the primary amino group then provides a protected suitable coupling partner 44. Preferred protecting groups $PG_1$ include Cbz, preferred protecting groups X for $NHR^5$ include Boc.

In accordance with the process of the present invention, the starting material represented by formula 38 above is treated with a sulfur ylide to produce an intermediate keto ylide compound represented by 39 [Kronenthal, D. et al., WO 02/14256 A1]. The sulfur ylide reagent is conveniently prepared from a sulfoxonium salt by reaction with a suitable base in an organic solvent. Suitable sulfoxonium compounds include trialkyl sulfoxonium halides, such as trimethylsuloxonium iodide. Preferable bases include, for example, sodium hydride, potassium tert-butoxide and potassium tert-amylate, with the latter being particularly preferred. The reaction is carried out in an organic solvent such as dimethylformamide, tetrahydrofuran or, preferably, toluene with mild heating, i.e. at a temperature of from about 60° C. to about 80° C., preferably about 70° C. Once the sulfur ylide reagent is formed, it is reacted with the starting material 38, optionally in the presence of a co-solvent. As an example of the use of a mixed solvent reaction medium, the reaction of the trialkyl-sulfoxonium compound and base is carried out in toluene as described, the resulting solution is cooled to about 0° C., and then added to a solution of the starting material in tetrahydrofuran to form the keto-ylide intermediate compound represented by 39 above.

The keto-ylide compound 39 is then converted to the bromoketone 40 by reaction with a source of bromide, preferably a basic source of bromide, most preferably lithium bromide, and an organic acid, for example, methanesulfonic acid. The treatment with the bromide source is carried out in an organic solvent, such as tetrahydrofuran, toluene or, preferably, acetonitrile. The reaction is initiated at low temperature, from about 0° C. to about 5° C. As the reaction proceeds however, the temperature is raised to about 65° C.

The bromoketone compound 40 is then converted to the epoxide 41 by reaction with a suitable hydride source such as

Scheme 8

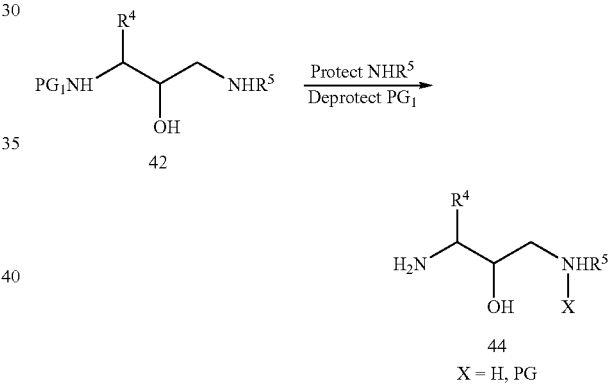

Additional methods for the preparation of 2-hydroxy-1,3-diaminopropanes exist, including those described in Maillaird, M.; Hom, C.; Gailunas, A.; Jagodzinska, B.; Fang, L. Y.; John, V.; Freskos, J. N.; Pulley, S. R.; Beck, J. P.; Tenbrink, R. E. WO 0202512, 2002. Additionally, a modification of the method of Ellman and coworkers (Kick, E. K.; Ellman, J. A. J. Med. Chem. 1995, 38, 1427-30.) provides

Scheme 9

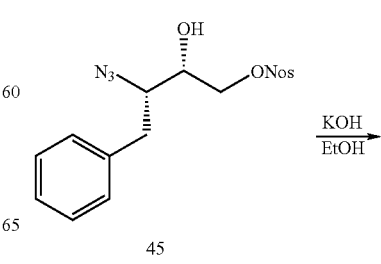

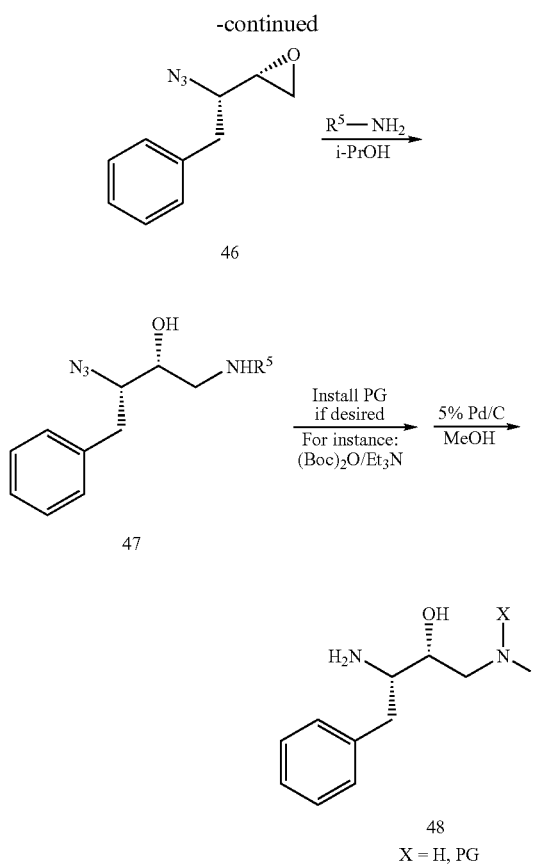

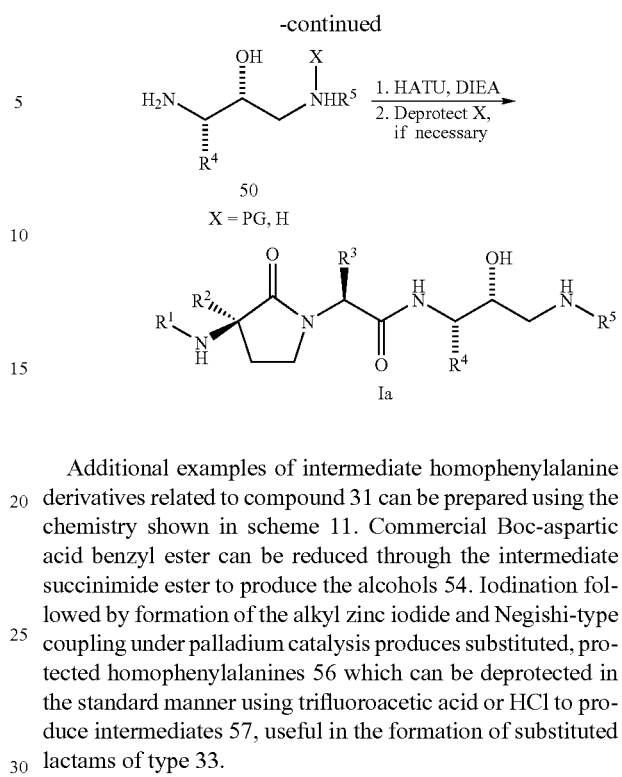

for the preparation of 3-azido-2-hydroxy-1-aminopropanes (47, Scheme 9) which are useful precursors to 2-hydroxy-1,3-diaminopropanes. These intermediates may be prepared from the reported intermediates of type 45. Treatment of the p-nitrophenylsulfonate (Nos) intermediate with base provides the azido epoxide 46. This versatile intermediate can be opened with amines to provide the azido alcohols. Optional protection of the secondary amine can then be performed, and the azide is then reduced under mild conditions to provide the primary amine 48 ready for coupling to lactam acids.

Coupling of a lactam acid 49 with a protected or unprotected amino alcohol 50 using methods previously described for making amide bonds, such as HATU and DIEA in DMF, provides a protected or unprotected product, which can be deprotected if necessary to provide the compounds Ia of the present invention (Scheme 10). Preferably, if a protecting group X is used, it is a Boc group, which is removed by treatment with trifluoroacetic acid in dichloromethane.

Scheme 10

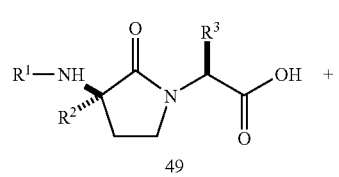

Additional examples of intermediate homophenylalanine derivatives related to compound 31 can be prepared using the chemistry shown in scheme 11. Commercial Boc-aspartic acid benzyl ester can be reduced through the intermediate succinimide ester to produce the alcohols 54. Iodination followed by formation of the alkyl zinc iodide and Negishi-type coupling under palladium catalysis produces substituted, protected homophenylalanines 56 which can be deprotected in the standard manner using trifluoroacetic acid or HCl to produce intermediates 57, useful in the formation of substituted lactams of type 33.

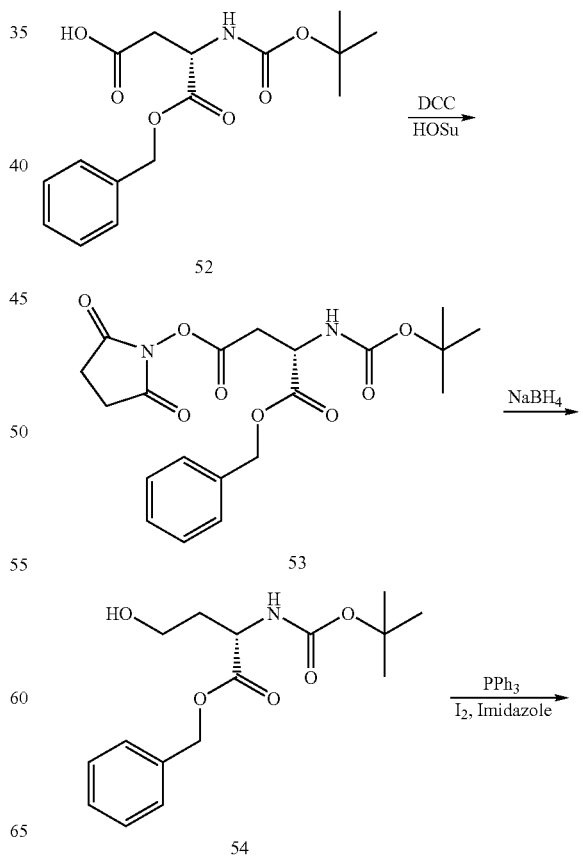

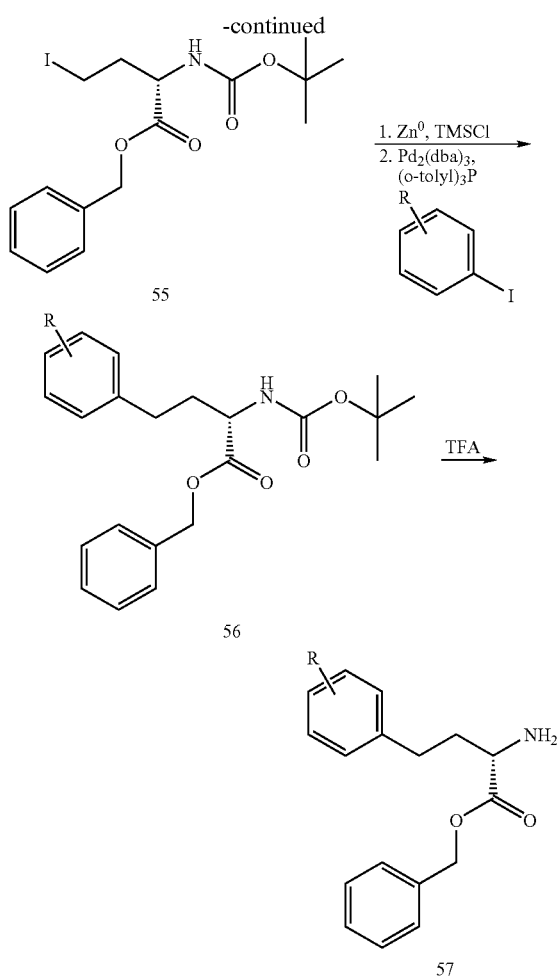

DESCRIPTION OF THE SPECIFIC EMBODIMENTS

The compounds of this invention and their preparation can be understood further by the following working examples. These examples are meant to be illustrative of the present invention, and are not to be taken as limiting thereof.

Chemical abbreviations used in the specification and Examples are defined as follows:

"Ac" for acetate,
"APCI" for atmospheric pressure chemical ionization,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDI" for 1,1'-carbonyldiimidazole,
"CD$_3$OD" for deuteromethanol,
"CDCl$_3$" for deuterochloroform,
"DCC" for 1,3-dicyclohexylcarbodiimide,
"DCM" for dichloromethane
"DEAD" for diethyl azodicarboxylate,
"DIEA" for N,N-diisopropylethylamine,
"DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"EDC" or "EDCI" for 1-(3-dimethylaminopropyl)-3-ethylcarbodiimide hydrochloride,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"TMSCH$_2$N$_2$" for (trimethylsilyl)diazomethane,
"TMSN$_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable. "LC-MS" refers to high pressure liquid chromatography carried out according to the definition for HPLC with a mass spectrometry detector.

Melting points were determined on a Mel-Temp II apparatus and are uncorrected. IR spectra were obtained on a single-beam Nicolet Nexus FT-IR spectrometer using 16 accumulations at a resolution of 4.00 cm-1 on samples prepared in a pressed disc of KBr or as a film on KBr plates. Proton NMR spectra (300 MHz, referenced to tetramethylsilane) were obtained on a Varian INOUA 300, Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer. HPLC analyses were obtained using a Rainin Dynamax C18 column with UV detection at 223 nm using a standard solvent gradient program as follows:

HPLC solvent conditions: When described as performed under "standard conditions", Samples were dissolved in methanol (1 mg/mL) and run using the following gradient program with a solvent flow rate of 1.0 mL/min.

| Time (min) | Acetonitrile (0.05% TFA) | H$_2$O (0.05% TFA) |
|---|---|---|
| Initial | 10 | 90 |
| 20.0 | 90 | 10 |
| 20-30 | 90 | 10 |

Preparatory HPLC: When described as performed under "standard conditions", Samples (approx. 20 mg) were dissolved in methanol (10 mg/mL) and purified on a 25 mm×50 mm Vydac C18 column with a 5 minute gradient elution from 10% to 100% buffer B in buffer A (buffer A: water containing 0.1% trifluoroacetic acid, buffer B: 10% water, 90% acetonitrile containing 0.1% trifluoroacetic acid) at 10 mL/minute.

Analytical HPLC: When described as "Method A", a sample dissolved in a suitable carrier solvent (methanol, acetonitrile, or the like) was analyzed on an Xterra 3.0×50 mm s7 column with a run time of 3 min and a gradient of 0-100% B over 2 min at a flowrate of 5 mL/min. Absorbance was monitored at 220 μM. Solvent A=0% MeOH/90% water/ 0.1% TFA and Solvent B=10% water/90% MeOH/0.1% TFA.

Analytical HPLC: When described as "Method B", a sample dissolved in a suitable carrier solvent (methanol, acetonitrile, or the like) was analyzed on an Xterra 3.0×50 mm s7 column with a run time of 4 min and a gradient of 0-100% B over 3 min at a flowrate of 5 mL/min. Absorbance was monitored at 220 μM. Solvent A=0% MeOH/90% water/ 0.1% TFA and Solvent B=10% water/90% MeOH/0.1% TFA.

The examples provided are intended to assist in a further understanding of the invention. Particular materials employed, species and conditions are intended to be further illustrate of the invention and not limit the reasonable scope thereof.

SYNTHESIS OF INTERMEDIATES

Preparation A (3S,2R)3-Amino-4-(3,4-difluoro-phenyl)-1-(3-methoxy-benzylamino)-butan-2-ol

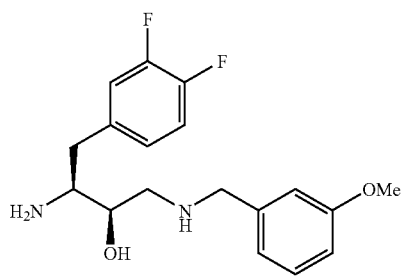

Step A(1). 3-(S)-2-oxo-3-(tertbutyloxycarbonylamino)-4-(3,4-difluoror phenyl)butylide dimethylsulfoxonium Trimethylsulfoxonium iodide (1.1 g, 4.7 mmol) suspended in THF (3.5 mL) was treated with potassium tert-butoxide (3.5 mL, 3.5 mmol, 1 M in THF) via syringe over one minute at RT. The reaction was stirred at 70° C. for two hours to afford the corresponding ylide that was reacted in solution without isolation. The reaction mixture was cooled to 0° C. and a solution of N-(2-t-butoxycarbonyl)-L-3,4-difluorophenylalanine-4-nitrophenyl ester (0.5 g, 1.2 mmol) in THF (3.0 mL) was added via cannula over 1 minute. The reaction was stirred at this temperature for five minutes and then was allowed to warm to ambient temperature over 30 minutes. The reaction mixture was stirred at ambient temperature for a further 30 minutes. The reaction was quenched with saturated sodium bicarbonate solution, diluted with ethyl acetate (25 mL), washed with saturated sodium bicarbonate solution (2×25 mL), the organic layer separated, dried (MgSO$_4$) and the solvent removed at reduced pressure. The yellowish residue was recrytallized from hexane to give the desired product as a yellow solid (0.41 g, 93%). MS: 376 (M+H, 100%).

Step A(2). (1S)-[3-Bromo-1-(3,4-difluoro-benzyl)-2-oxo-propyl]-carbamic acid tert-butyl ester

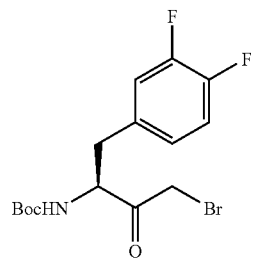

A solution of 3-(S)-2-oxo-3-(tertbutyloxycarbonylamino)-4-(3,4-difluororphenyl)butylide dimethylsulfoxonium (0.34 g, 0.91 mmol) in THF (3 mL) was cooled to 0° C. and treated with lithium bromide (0.087 g, 0.91 mmol) in one portion. After all the lithium bromide dissolved, methanesulfonic acid (0.056 mL, 0.91 mmol) was added dropwise over 30 seconds. A slurry begins to form after 5 minutes and the cooling bath is replaced with an oil bath. The reaction was heated to 65° C. for two hours. The reaction was allowed to cool to ambient temperature, quenched with saturated sodium bicarbonate solution, diluted with ethyl acetate (25 mL), washed with saturated sodium bicarbonate solution (2×25 mL), the organic layer separated, dried (MgSO$_4$) and the solvent removed at reduced pressure. The desired product was obtained as an orange oil and used without further purification (0.3 g, 90%). MS: 380 (M+H, 100%).

Step A(3). (1S,2S) [2-(3,4-Difluoro-phenyl)-1-oxiranyl-ethyl]-carbamic acid tert-butyl ester

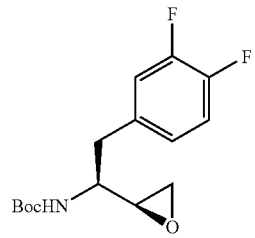

A solution of (1S)-[3-Bromo-1-(3,4-difluoro-benzyl)-2-oxo-propyl]-carbamic acid tert-butyl ester (0.14 g, 0.36 mmol) in ethanol:THF (2:1) (3 mL) was cooled to 0° C. and treated with sodium borohydride (0.014 g, 0.36 mmol) in one portion. After 30 minutes the cooling bath was removed and the reaction mixture was stirred at ambient temperature for 12 hours. The solvent was removed and the residue partitioned between saturated sodium bicarbonate solution (20 mL) and ethyl acetate (20 mL). The organic phase was washed with saturated sodium bicarbonate solution (25 mL), separated, dried (MgSO$_4$) and the solvent removed at reduced pressure. The product was recrystallized from hexane to give the desired product as the major isomer (>9:1) by NMR (0.095 g, 90%). MS: 300 (M+H, 100%).

Step A(4). (1S,2R)-[1-(3,4-Difluoro-benzyl)-2-hydroxy-3-(3-methoxy-benzylamino)-propyl]-carbamic acid tert-butyl ester

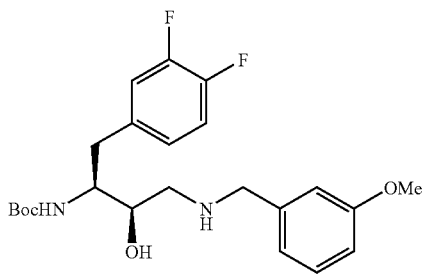

A solution of (1R,2S)-[2-(3,4-difluoro-phenyl)-1-oxiranyl-ethyl]-carbamic acid tert-butyl ester (0.03 g, 0.1 mmol) in acetonitrile (1 mL) was treated with lithium triflate (0.032 g, 0.2 mmol) and stirred at ambient temperature for 20 minutes. Then 3-methoxybenzylamine (0.016 mL, 0.12 mmol) was added to the reaction neat in one portion. The reaction was stirred at ambient temperature for 14 hours. The reaction was poured into saturated ammonium chloride solution (5 mL), extracted with ethyl acetate, the organic phase separated, dried (MgSO$_4$) and the solvent removed at reduced pressure. The product was obtained as an oil and used without further purification (0.041 g, 94%). MS: 437 (M+H, 100%).

Step A(5): Preparation A. (3S,2R)3-Amino-4-(3,4-difluoro-phenyl)-1-(3-methoxy-benzylamino)-butan-2-ol A solution of (1R,2S)-[1-(3,4-Difluorobenzyl)-2-hydroxy-3-(3-methoxy-benzylamino)-propyl]-carbamic acid tert-butyl ester (0.04 g, 0.09 mmol) in methylene chloride (1 mL) was treated with 4 N HCl in dioxane (1 mL) at ambient temperature in one portion. The reaction was stirred for 12 hours and the solvent removed at reduced pressure to give the product as a solid (0.033 g, 98%). MS: 337 (M+H, 100%).

Preparation B (3S,2R)-3-Amino-4-(3,5-difluoro-phenyl)-1-(3-methoxy-benzylamino)-butan-2-ol

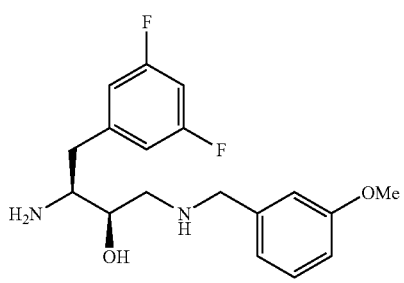

Following the general procedure for Preparation (A) using N-(2-t-butoxycarbonyl)-L-3,5-difluorophenylalanine-4-nitrophenyl ester as the starting material the title compound was obtained. MS: 337 (M+H, 100%).

Preparation C (3S,2R)3-Amino-4-(4-chloro-phenyl)-1-(3-methoxybenzylamino)-butan-2-ol

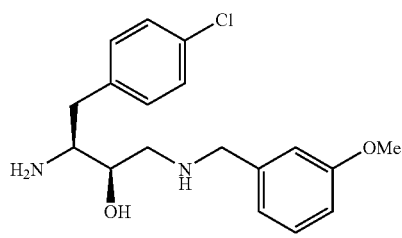

Following the general procedure for Preparation (A) using N-(2-t-butoxycarbonyl)-L-4-chlorophenylalanine-4-nitrophenyl ester as the starting material the title compound was obtained. MS: 335 (M+H, 100%).

Preparation D (3S,2R)(3-Amino-2-hydroxy-4-phenyl-butyl)-(3-methoxy-benzyl)-carbamic acid tert-butyl ester

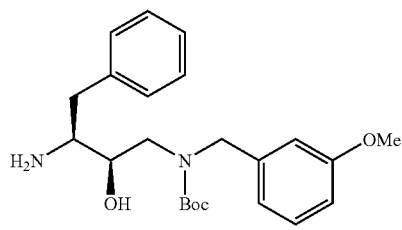

Step D(1). (1S,2S)2-(1-Azido-2-phenyl-ethyl)-oxirane

A solution of 1.0 g (2.5 mmol) of 4-Nitro-benzenesulfonic acid 3-azido-2-hydroxy-4-phenyl-butyl ester (Kick, E. K.; Ellman, J. A. *J. Med. Chem.* 1995, 38, 1427-30) in 12 mL of Ethanol and 8 mL of ethyl acetate is treated with KOH (157 mg, 2.8 mmol). After 2 h at rt 10 mL of water is added and 20 mL of CH$_2$Cl$_2$ is added. The organic layer is separated, washed with brine and Na$_2$SO$_4$, and concentrated. Chromatography eluting with hexanes/ethyl acetate 5:1 provides 450 mg (95%) of the desired product. $^1$H NMR (δ) 7.21-7.36 (m, 5H), 3.58 (dt, 2H, J=9, 5 Hz), 3.05 (m, 1H) 2.97 (dd, 1H, J=13.9, 4.8), 2.77-2.83 (m, 3H).

Step D(2). (3S,2R)3-Azido-1-(3-methoxy-benzylamino)-4-phenyl-butan-2-ol

A solution of the compound of intermediate D(1) (225 mg, 1.18 mmol) in 9 mL of isopropyl alcohol is treated with 3-methoxybenzylamine (1.74 mmol, 230 μL). The solution was heated to 85° C. and stirred for 3 h. The reaction mixture was then directly concentrated and the product obtained by chromatography eluting with 2% methanol in CH$_2$Cl$_2$ to obtain 200 mg (52%) of the desired product as a clear oil. MS (M+H)$^+$=327.3

Step D(3). (3S,2R) (3-Azido-2-hydroxy-4-phenyl-butyl)-(3-methoxy-benzyl)-carbamic acid tert-butyl ester A solution of the compound of intermediate D(2) (100 mg, 0.308 mmol) in 2 mL of $CH_2Cl_2$ is treated with di(tert-butyl) dicarbonate (0.33 mmol, 73 mg) and triethylamine (0.46 mmol, 63 µL). After stirring at rt for 2 h water was added (5 mL) and the organic layer was separated. The aqueous layer was extracted with 2 additional 10 mL portions of ethyl acetate and the combined organic layer was dried over $Na_2SO_4$ and concentrated. Chromatography eluting with a gradient of hexanes/ethyl acetate 4:1 to 1:1 provided 125 mg (95%) of the desired product. MS (M+H-Boc)$^+$=327.3, NMR (δ) 1.47 (s, 9H, Boc group)

Step D(4): Preparation D. (3S,2R)(3-Amino-2-hydroxy-4-phenyl-butyl)-(3-methoxy-benzyl)-carbamic acid tert-butyl ester A solution of the compound of intermediate D(3) (125 mg, 0.29 mmol) was dissolved in 3 mL of methanol and 25 mg of 5% palladium on carbon was added. The suspension was placed under 50 psi of hydrogen on a parr apparatus and shaken overnight. The catalyst was removed by filtration and the product was obtained by concentration with no purification necessary (100 mg, 86%). MS (M+H)$^+$=401.3

Preparation E (3S,2R)(3-Amino-2-hydroxy-5-methyl-hexyl)-(3-methoxy-benzyl)-carbamic acid tert-butyl ester

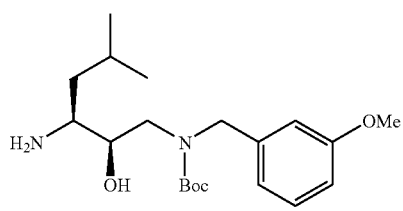

Step E(1). {1(S)-[1(R)-Hydroxy-2-(3-methoxy-benzylamino)-ethyl]-3-methyl-butyl}-carbamic acid benzyl ester Following the general procedure for intermediate A(4) using N-(benzyloxycarbonyl)-L-leucine-4-nitrophenyl ester as the starting material the title compound is obtained. MS (M+H)$^+$=401.4.

Step E(2). (3(S)-Benzyloxycarbonylamino-2(R)-hydroxy-5-methyl-hexyl)-(3-methoxy-benzyl)-carbamic acid tert-butyl ester Following the general procedure for the synthesis of intermediate D(4) 1.0 g of the compound of Step E(1) is converted to 800 mg (80%) of the title compound. MS (M+H)$^+$=501.4, (M+Na)==523.4.

Step E(3): Preparation E. (3(S)-Amino-2(R)-hydroxy-5-methyl-hexyl)-(3-methoxy-benzyl)-carbamic acid tert-butyl ester In a Parr flask 60 mg of 5% palladium on carbon was suspended in 5 ml of methanol. The compound of intermediate E(2) (300 mg, 0.6 mmol) was added and the resulting slurry was placed under 40 psi of hydrogen for 16 h in a Parr apparatus. The catalyst was then removed by filtration and the title compound of Preparation (E) (250 mg, 85%) was isolated by concentrating the resulting solution. MS (M+H)$^+$=367.4

Preparation F (3S,2R)(3-Amino-2-hydroxy-4-phenyl-butyl)-(3-methoxy-benzyl)-carbamic acid benzyl ester

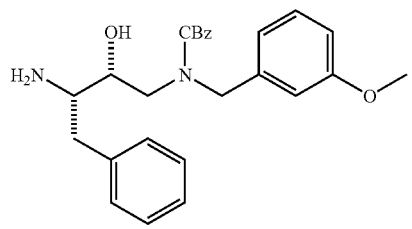

Step F(1). (1S,2R)[1-Benzyl-2-hydroxy-3-(3-methoxy-benzylamino)-propyl]-carbamic acid tert-butyl ester Following the general procedure for the preparation of Preparation (A), step A(4), but using N-Boc-phenylalanine as the starting material the compound of step F(1) was obtained. MS ESI (M+H)$^+$=401.3.

Step F(2). (1S,2R){1-Benzyl-3-[benzyloxycarbonyl-(3-methoxy-benzyl)-amino]-2-hydroxy-propyl}-carbamic acid tert-butyl ester The compound from step F(1) (1.5 g, 3.7 mmol) was dissolved in 30 mL of $CH_2Cl_2$ and benzyl chloroformate (0.6 mL, 3.9 mmol) and triethylamine (1 mL) were added. After stirring at rt for 2 h, the reaction solution was diluted with water and extracted with 2 50 mL portions of $CH_2Cl_2$. The combined organic layers were dried and concentrated to provide a crude product which was purified by chromatography eluting with 25-50% ethyl acetate in hexanes to provide 1.7 g (86%) of the desired product.

Step F(3). Preparation F. (3S,2R)(3-Amino-2-hydroxy-4-phenyl-butyl)-(3-methoxy-benzyl)-carbamic acid benzyl ester The compound from step F(2) (29 mg, 0.054 mmol) was dissolved in 3 mL of 4.0 M HCl in dioxane. After 1 h at rt, the solvent was removed by evaporation to provide the amine HCl salt which was used without further purification. ESI MS (M+H)=435.3.

Preparation G (3S,2R)-3-Amino-4-(2-fluoro-phenyl)-1-(3-methoxy-benzylamino)-butan-2-ol

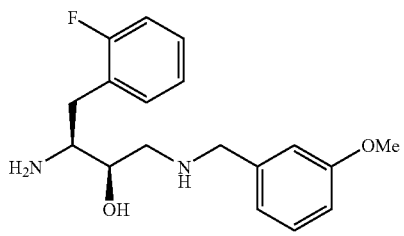

Following the general procedure for Preparation (A) using N-(2-t-butoxycarbonyl)-L-2-fluorophenylalanine-4-nitrophenyl ester as the starting material the title compound was obtained. MS: 319.3 (M+H, 100%).

Preparation H (3S,2R)-3-Amino-4-(2-fluoro-phenyl)-1-(3-chloro-benzylamino)-butan-2-ol

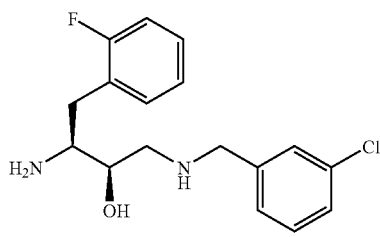

Step H(1): Following the general procedure for the synthesis of the compound of Preparation A(3) but using N-(2-t-butoxycarbonyl)-L-2-fluorophenylalanine-4-nitrophenyl ester as the starting material the epoxide was obtained. APCI MS: (M+H)$^+$=282.

Step H(2): Following the general procedure for the synthesis of the compound of Preparation A(4) but using the epoxide from step H(1) and 3-chlorobenzylamine the amine of step H(2) was prepared. APCI MS: (M+H)$^+$=423.

Step H(3): Following the general procedure for the synthesis of the compound of Preparation A(5) but using the amine from step H(2) the title compound of Preparation (H) was prepared. APCI MS: (M+H)$^+$=323.

Preparation I (3S)-(3-Amino-2-hydroxy-4-phenyl-butyl)-(3-methoxy-benzyl)-carbamic acid tert-butyl ester

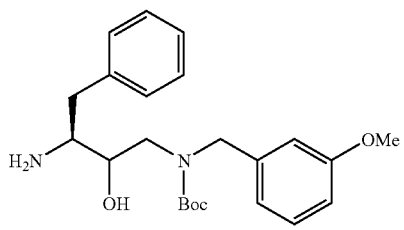

Step I(1): Following the general procedure for the synthesis of the compound of Preparation (A) but using N-(2-t-butoxycarbonyl)-L-phenylalanine-4-nitrophenyl ester as the starting material and omitting the crystallization step in the preparation of the intermediate I(3), the compound of Preparation (I) was prepared as an approximately 1:2 mixture of the erythro:threo diastereomers at C2. ESI MS (M+H)$^+$=401.43.

Preparation J (3S,2R)-3-Amino-1-(3-chloro-benzylamino)-4-phenyl-butan-2-ol

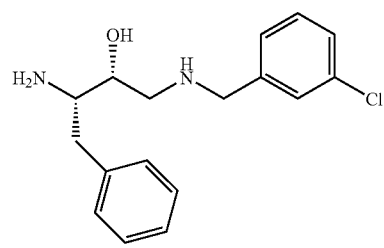

Step J(1): Following the general procedure for the synthesis of the compound of Preparation A(3) but using N-(2-t-butoxycarbonyl)-L-phenylalanine-4-nitrophenyl ester as the starting material the epoxide was obtained. APCI MS: (M+H)$^+$=264.

Step J(2): Following the general procedure for the synthesis of the compound of Preparation A(4) but using the epoxide from step J(1) and 3-chlorobenzylamine the amine of step J(2) was prepared. APCI MS: (M+H)$^+$=405.2.

Step J(3): Following the general procedure for the synthesis of the compound of Preparation A(5) but using the amine from step J(2) the title compound of Preparation (H) was prepared as the solid HCl salt. APCI MS: (M+H)$^+$=305.2.

Preparation K (3S,2R)-3-Amino-4-phenyl-1-prop-2-ynylamino-butan-2-ol

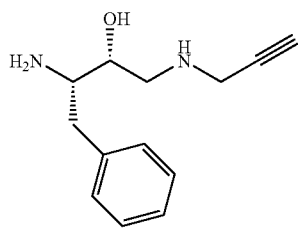

Step K(1): Following the general procedure for the synthesis of the compound of Preparation A(4) but using the epoxide from step J(1) and propargylamine the amine of step K(1) was prepared. APCI MS: (M+H)$^+$=319.

Step K(2): Following the general procedure for the synthesis of the compound of Preparation A(5) but using the amine from step K(1) the title compound of Preparation (K) was prepared as the solid HCl salt. APCI MS: (M+H)$^+$=219.

Preparation L (3S,2R) (3-Amino-2-hydroxy-4-phenyl-butyl)-cyclopropylmethyl-carbamic acid tert-butyl ester

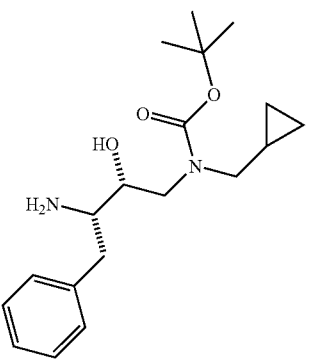

Following the general procedure for Preparation (A) (steps A4-A5) using (1S,2S) (1-Oxiranyl-2-phenyl-ethyl)-carbamic-acid benzyl ester as the starting material, the title compound was obtained as a colorless oil (136 mg) in a 44% yield. LC-MS (column=XTERRA C18 S7, 3×50 mm, start % B=0, final % B=100, gradient time=2 min, flow rate=5 ml/min) m/e 335.28 (M+H)$^+$, $t_R$ 1.30 min.

Preparation M (3S,2R)-(3-Amino-2-hydroxy-4-phenyl-butyl)-(3,5-difluoro-benzyl)-carbamic acid tert-butyl ester

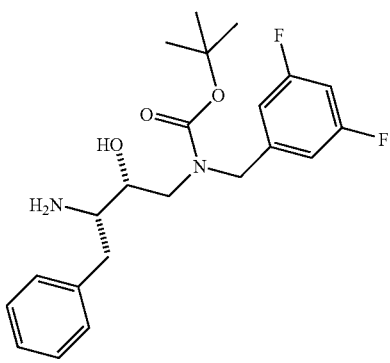

Following the general procedure for Preparation (A) (steps A4-A5) using (1S,2S) (1-Oxiranyl-2-phenyl-ethyl)-carbamic acid benzyl ester as the starting material the title compound was obtained. LC-MS (column=XTERRA C18 S7, 3×50 mm, start % B=0, final % B=100, gradient time=2 min, flow rate=5 ml/min) m/e 407.27 (M+H)$^+$, $t_R$ 1.44 min.

Preparation N (3S,2R)-(3-Amino-2-hydroxy-4-phenyl-butyl)-(3-trifluoromethyl-benzyl)-carbamic acid tert-butyl ester

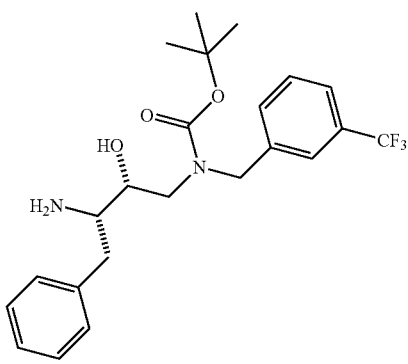

Following the general procedure for Preparation (A) (steps A4-A5) using (1S,2S)(1-Oxiranyl-2-phenyl-ethyl)-carbamic acid benzyl ester as the starting material the title compound was obtained as an amber oil (728 mg) in a quantitative yield. LC-MS (column=XTERRA C18 S7, 3×50 mm, start % B=0, final % B=100, gradient time=2 min, flow rate=5 ml/min) m/e 439.24 (M+H)$^+$, $t_R$ 1.60 min.

Preparation O (3S,2R)-(3-Amino-2-hydroxy-4-phenyl-butyl)-benzyl-carbamic acid tert-butyl ester

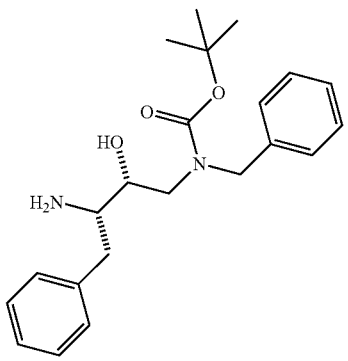

Following the general procedure for Preparation (A) (steps A4-A5) using (1S,2S)(1-Oxiranyl-2-phenyl-ethyl)-carbamic acid benzyl ester as the starting material the title compound was obtained as an colorless oil (190 mg) in a 52% yield. LC-MS (column=XTERRA C18 S7, 3×50 mm, start % B=0, final % B=100, gradient time=2 min, flow rate=5 ml/min) m/e 371.30 (M+H)$^+$, $t_R$ 1.47 min.

Preparation P (3S,2R)-(3-Amino-2-hydroxy-4-phenyl-butyl)-(3-fluoro-5-trifluoromethyl-benzyl)-carbamic acid tert-butyl ester

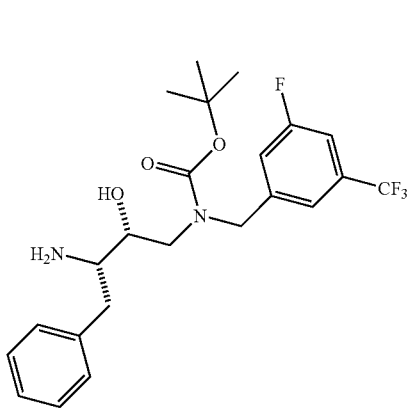

Following the general procedure for Preparation (A) (steps A4-A5) using (1S,2S)(1-Oxiranyl-2-phenyl-ethyl)-carbamic acid benzyl ester as the starting material the title compound was obtained as an amber oil (580 mg) in a 64% yield. LC-MS (column=XTERRA C18 S7, 3×50 mm, start % B=0, final % B=100, gradient time=2 min, flow rate=5 ml/min) m/e 457.23 (M+H)$^+$, $t_R$ 1.65 min.

Preparation Q (3S,2R)-(3-Amino-2-hydroxy-4-phenyl-butyl)-(2-cyano-ethyl)-carbamic acid tert-butyl ester

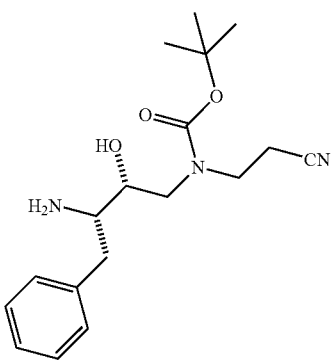

Following the general procedure for Preparation (A) (steps A4-A5) using (1S,2S)(1-Oxiranyl-2-phenyl-ethyl)-carbamic acid benzyl ester as the starting material the title compound was obtained as an amber oil (250 mg) in a 32% yield. LC-MS (column=XTERRA C18 S7, 3×50 mm, start % B=0, final % B=100, gradient time=2 min, flow rate=5 ml/min) m/e 234.33 (M+H)$^+$, $t_R$ 1.08 min.

EXAMPLE 1

(2S)-2-(3-Acetylamino-3-isopropyl-2-oxo-pyrrolidin-1-yl)-N-[(1S,2R)-1-(3,5-difluoro-benzyl)-2-hydroxy-3-(3-methoxy-benzylamino)-propyl]-4-phenyl-butyramide

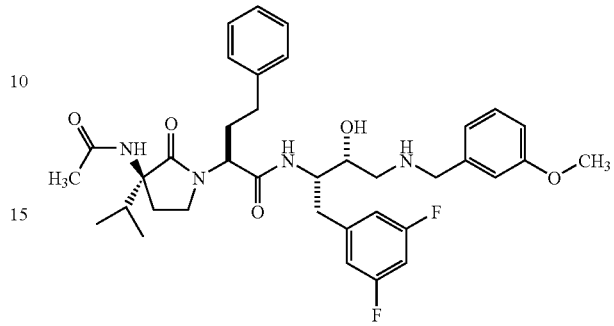

Step (1a): Cs$_2$CO$_3$ was added to a stirred solution of N-Cbz-Valine (7.03 g, 27.9 mmol) in dry DMF (45 mL). The reaction mixture was stirred for 15 min after which allyl bromide (5.0 mL, 56 mmol) was added dropwise. The reaction mixture was stirred overnight and then filtered through celite. The filtrate was diluted with ethyl acetate, washed with water (3×) and brine (1×). The organic phase was dried over MgSO$_4$, filtered and concentrated in vacuo. The residue was purified by silica gel column chromatography to yield 8.1 g (99%) allyl ester. ESI (M+Na)$^+$=314.3. $^1$H-NMR (CDCl$_3$) δ7.33 (m, 5H), 5.88 (m, 1H), 5.49 (d, j=8.8 Hz, 1H), 5.35-5.16 (m, 2H), 5.10 (s, 2H), 4.62 (m, 2H), 4.36-4.31 (m, 1H), 2.20-2.15 (m, 1H), 0.96 (d, J=7 Hz, 3H), 0.89 (d, J=7 Hz, 3H).

Step (1b): A freshly prepared LDA solution (14.31 mmol) was added to a stirred mixture of allylic ester from (1a) (1.39 g, 4.77 mmol) and ZnCl$_2$ (10.5 mL, 5.25 mmol) in 20 mL THF at −20° C. The mixture was allowed to warm up to room temperature overnight. The reaction solution was diluted with ether and hydrolyzed with 1 N hydrochloric acid. The aqueous phase was extracted with ether. The combined ether extracts were washed with brine, dried over MgSO$_4$, filtered and concentrated. The residue was purified by silica gel chromatography to provide acid 0.39 g (28%) of viscous oil. ESI (M−H)−=290.2.

Step (1c): Acid from (1b) (200 mg, 0.686 mmol), DIEA (0.385 mL, 2.74 mmol) PyBOP (713 mg, 3.19 mmol) were mixed in 5 mL of CH$_2$Cl$_2$ and stirred for 5 min. homo-Phe methyl ester (265 mg, 1.372 mmol) was then added and the mixture was stirred for over night. The reaction solution was concentrated in vacuo. The residue was purified by silica gel chromatography to provide amide 0.60 g (75%). ESI (M+H)$^+$=467.4; (M+Na)$^+$=489.3. $^1$H-NMR (CDCl$_3$) δ7.36-7.15 (m, 10H), 5.72-5.70 (m, 1H), 5.14-5.09 (m, 3H), 4.65-4.58 (m, 1H), 3.71 (s, 3H), 2.95-1.95 (m, 9H), 1.01-0.94 (dd, J=5.5 Hz, 6H).

Step (1d): Ozone was bubbled through a solution of amide from (1c) in 10 mL of CH$_2$Cl$_2$ (0.83 g, 1.78 mmol) at −78° C. until a blue color persisted. Residual ozone was removed with a stream of oxygen. Triphenyl phosphine (0.70 g, 2.67 mmol) was added, and the reaction mixture was allowed to warm to rt. After 1 h, the solution was concentrated under reduced pressure. The residue was purified by chromatography on silica gel to provide aldehyde 0.59 g (70%). ESI (M+H)$^+$=469.5. $^1$H-NMR (CDCl$_3$) δ7.32-7.18 (m, 10H), 5.60-4.88 (m, 3H), 5.30 (s, 2H), 3.73-3.67 (dd, J=7.4 Hz, 2H), 2.95-2.07 (m, 4H), 1.0-0.95 (m, 6H).

Step (1e): 6 mL of TFA/Et$_3$SiH (1:1) was added to the solution of aldehyde from (1d) (0.59 g, 1.26 mmol) in 10 mL of CH$_2$Cl$_2$ at 0° C. The mixture was stirred at 0° C. for 3 h. The reaction solution was concentrated under reduced pressure.

The residue was purified by chromatography on silica gel to provide lactam 0.41 g (72%). ESI (M+H)$^+$=453.4. $^1$H-NMR (CDCl$_3$) δ7.36-7.17 (m, 10H), 5.29-4.60 (m, 3H), 3.71-3.67 (ss, 3H), 3.60-3.40 (m, 1H), 3.40-3.25 (m, 1H), 2.85-2.05 (m, 6H), 1.01-0.92 (m, 6H).

Step (1f): A solution of lactam from (1e) (350 mg, 0.77 mmol) in 15 mL of Methanol/Ethyl Acetate (1:1) was hydrogenated over 10% palladium on carbon (100 mg) for overnight. The solution was filtered through celite and concentrated under reduced pressure to afford the desired amine 0.23 g (95%). ESI (M+H)$^+$=319.4. $^1$H-NMR (CDCl$_3$) δ7.32-7.16 (m, 5H), 4.79-4.70 (m, 1H), 3.70-3.68 (s, 3H), 3.50-3.40 (m, 1H), 3.30-3.20 (m, 1H), 2.65-1.20 (m, 6H), 1.35-0.86 (m, 6H).

Step (1g): A mixture of amine (0.23 g, 0.73 mmol) from (1f), acetic anhydride (0.5 mL, 0.53 mmol), DIEA (1.0 mL, 7.1 mmol) and DMAP (50 mg, 0.41 mmol) in 5 mL of CH$_2$Cl$_2$ were stirred at room temperature for overnight. The reaction solution was concentrated and the residue was purified by chromatography on silica gel to provide amide 0.20 g(76%). ESI (M+H)$^+$=361.4; (M+Na)$^+$=383.4.

Step (1 h): The amide (0.20 g, 0.56 mmol) from (1g) was dissolved in 10 mL of THF/H$_2$O (1:1). LiOH (100 mg, 2.44 mmol) was added and the mixture was stirred for overnight. It was then diluted with ethyl acetate and acidified with 1N HCl. The aqueous layer was extracted with 3× ethyl acetate. The combined organic layer was dried over MgSO$_4$, filtered and evaporated under reduced pressure to give acid 0.19 g (98%). ESI (M–H)$^-$=345.3. $^1$H-NMR (CDCl$_3$) δ7.28-7.16 (m, 5H), 5.30 (s, 3H), 4.81-4.77 (m, 1H), 4.13-3.42 (m, 3H), 2.80-1.80 (m, 6H), 2.07 (s, 3H), 1.30-1.23 (m, 1H), 0.99-0.81 (dd, J=6.9 Hz, 6H).

Step (1i): A mixture of acid from (1 h) (15 mg, 0.043 mmol), PyBOP (24 mg, 0.018 mmol), and DIEA (20 μL, 0.14 mmol) in 4 mL of CH$_2$Cl$_2$ was stirred at room temperature for 5 min. Amine-HCl salt Preparation (B) (15 mg, 0.040 mmol) in 1 mL of CH$_2$Cl$_2$ was added and the solution was continued to stir for overnight. The reaction solution was concentrated under reduced pressure and the residue was purified on preparative LC-MS (reverse phase HPLC) to afford the desired product. ESI (M+H)$^+$=665.34. $^1$H-NMR (CDCl$_3$) δ8.21-6.40 (m, 10H), 4.50-3.20 (m, 10H), 3.78 (s, 3H), 2.50-1.40 (m, 10 H), 2.02 (s, 3H), 1.07-0.90 (dd, J=6.6 Hz, 6H).

EXAMPLE 2

(2S)-2-(3(S)-Acetylamino-3-((S)-sec-butyl)-2-oxo-pyrrolidin-1-yl)-N-[(1S,2R)-1-(3,5-difluoro-benzyl)-2-hydroxy-3-(3-methoxy-benzylamino)-propyl]-4-phenyl-butyramide

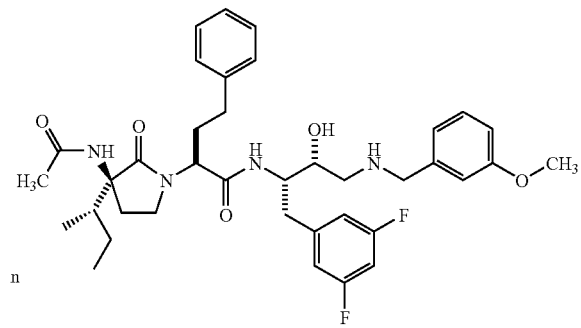

Step (2a): L-Isoleucine (10.0 g, 76.24 mmol), benzaldehyde (8.57 g, 76.24 mmol) and 4 Å molecular sieve (20 g) were added to a solution of NaOH (3.05 g, 76.24 mmol) in anhydrous MeOH (100 mL). The mixture was stirred at room temperature for overnight. After removal of molecular sieve by filtration with celite, the filtrate was evaporated under reduced pressure to give a solid, which was further dried under vacuum for 8 h to give Schiff base 18.0 g (98%) as an off-white solid. $^1$H-NMR (DMSO-d$_6$) δ 8.12 (s, 1H), 7.65 (m, 2H), 7.36 (m, 3H), 2.45 (m, 1H), 1.38 (m, 1H), 0.91 (m, 1H), 0.76 (m, 6H).

Step (2b): 250 mL of CH$_2$Cl$_2$ was added to the Schiff base from (2a) (12.0 g, 49.74 mmol). The solution was cooled to –20° C. After which 10.7 mL (74.61 mmol, 1.5 eq) benzyl chloroformate was added. Stirred at –20° C. for 96 h, warmed to room temperature, and diluted with CH$_2$Cl$_2$. The reaction mixture was washed 2× each with water, aq. NaHCO$_3$, aq. sodium bisulfite and water again. The organic layer was dried over MgSO$_4$, filtered, and the filtrate was concentrated and the residue was purified by chromatography on silica gel to give oxazolidinone 11 g (63%) as oil. APCI (M+H)$^+$=354.3. $^1$H-NMR (CDCl$_3$) δ 7.54-7.26 (m, 10H), 6.76 (s, 1H), 5.23 (s, 2H), 4.36-4.34 (dd, J=5.8 Hz, 1H), 1.80 (m, 1H), 1.60-1.20 (m, 2H), 0.86-0.80 (m, 6H).

Step (2c): 570 mg (1.613 mmol) of oxazolidinone from (2b) in 10 mL anhydrous of THF was cooled to –78° C. Then added 0.22 mL (2.42 mmol, 1.5 eq) of allyl iodide followed by 4.8 mL of 0.5N (2.4 mmol, 1.5 eq) potassium bis(trimethylsilyl)amide. TLC at 60 min showed the reaction was complete, so it was quenched with aqueous NH$_4$Cl and warmed to room temperature. Then the solution was diluted with water and extracted with ethyl acetate. The combined ethyl acetate extracts were washed with dilute aqueous NH$_4$Cl, dried over MgSO$_4$, filtered, and the filtrate was concentrated. The residue was purified by silica gel chromatography to give disubstituted oxazolidinone 567 mg (89%). ESI (M+H)$^+$=394.4. $^1$H-NMR (CDCl$_3$) δ7.42-7.26 (m, 10H), 6.34 (s, 1H), 5.68-5.57 (m, 1H), 5.16-5.12 (dd, J=9 Hz, 2H), 5.06 (s, 2H), 2.72-2.66 (m, 2H), 1.70-1.30 (m, 2H), 1.12-0.88 (m, 6H).

Step (2d): 567 mg (1.44 mmol) of disubstituted oxazolidinone from (2c) was dissolved in 40 mL of THF-MeOH (3:1). 10 mL 2N NaOH was added and the mixture was refluxed for 2 h. The THF and MeOH was evaporated, diluted ethyl acetate and acidified with HCl. Extracted 2× with ethyl acetate, dried the organic layer with MgSO$_4$, filtered and the filtrate was evaporated. The residue was pumped on high vacuum to give crude acid 695 mg. ESI (M–H)$^-$=304.3.

Step (2e): 695 mg of acid (2.27 mmol) from (2d), 15 mL of CH$_2$Cl$_2$, 488 mg HOBt (3.19 mmol, 1.4 eq) and 655 mg EDC (3.42 mmol, 1.5 eq) were mixed and stirred for 5 min. 660 mg (3.42 mmol, 1.5 eq) of homo-Phe methyl ester and 0.80 mL of DIEA (5.68 mmol, 2.5 eq) were then added and the mixture was stirred for 4 h. The reaction solution was diluted with ethyl acetate and washed with 5% citric acid and 5% NaHCO$_3$, dried over MgSO$_4$, filtered, and the filtrate was evaporated. The residue was purified by silica gel chromatography to provide Amide 0.53 g (76.7% for steps 2d and 2e). ESI (M+H)$^+$=481.5. $^1$H-NMR (CDCl$_3$) δ7.36-7.14 (m, 10H), 5.80-5.65 (m, 2H), 5.20-5.00 (m, 2H), 5.08 (s, 2H), 4.65-4.55 (m, 1H), 3.70 (s, 3H), 2.90-1.90 (m, 7H), 1.63-1.00 (m, 2H), 1.00-0.91 (m, 6H).

Step (2f): Ozone was bubbled through a solution of alkene from (2e) in 10 mL of CH$_2$Cl$_2$ (0.78 g, 1.62 mmol) at –78° C. until a blue color persisted. Residual ozone was removed with a stream of oxygen. Triphenyl phosphine (0.60 g, 2.29 mmol) was added, and the reaction mixture was allowed to warm to rt. After 1 h, the solution was concentrated under reduced pressure. The residue was purified by chromatography on silica gel to provide aldehyde 0.47 g (61%). ESI (M+H)$^+$=483.4, (M+Na)$^+$=505.4.

Step (2g): 5 mL of TFA/Et$_3$SiH (1:1) was added to the solution of aldehyde from (2f) (0.47 g, 0.97 mmol) in 10 mL of CH$_2$Cl$_2$ at 0° C. The mixture was stirred at 0° C. for 3 h. The reaction solution was concentrated under reduced pressure. The residue was purified by chromatography on silica gel to provide lactam 0.23 g (50%). ESI (M+H)$^+$=467.38. $^1$H-NMR (CDCl$_3$) δ7.34-7.16 (m, 10H), 5.45 (br, 1H), 5.05 (s, 2H), 4.87-4.82 (dd, J=4 Hz, 1H)), 3.65-3.35 (m, 2H), 3.67 (s, 3H), 2.90-1.45 (m, 8H), 1.20-1.00 (m, 1H), 0.98-0.90 (m, 6H).

Step (2h): A solution of lactam from (2g) (225 mg, 0.48 mmol) in Methanol (15 mL) was hydrogenated over 10% palladium on carbon (40 mg) for overnight. The solution was filtered through celite and concentrated under reduced pressure to afford the desired amine. ESI (M+H)$^+$=333.4. $^1$H-NMR (CDCl$_3$) δ7.29-7.16 (m, 5H), 4.78-4.60 (m, 3H), 3.68 (s, 3H), 3.44-3.37 (m, 2H), 2.68-1.85 (m, 8H), 1.20-1.00 (m, 1H), 0.96-0.91 (m, 6H).

Step (2i): A mixture of acetic acid (54 mL, 0.91 mmol), HATU (348 mg, 0.92 mmol), and DIEA (257 μL, 0.91 mmol) in 5 mL of DMF was stirred at room temperature for 5 min. Amine (152 mg, 0.46 mmol) from (2h) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified by chromatography on silica gel to provide lactam 160 mg (94%). ESI (M+H)$^+$=375.2. $^1$H-NMR(CDCl$_3$) δ7.33-7.17 (m, 5H), 6.07 (br, 1H), 4.66-4.61 (m, 1H), 3.73 (s, 3H), 3.60-3.20 (m, 2H), 2.70-1.60 (m, 8H), 1.20-1.00 (m, 1H), 0.98-0.86 (m, 6H).

Step (2j): Compound (0.20 g, 0.53 mmol) from (2h) was dissolved in 5 mL of THF/H$_2$O (4:1). LiOH (120 mg, 2.9 mmol) was added and the mixture was stirred for overnight. It was then diluted with ethyl acetate, acidified with 1N HCl. The aqueous layer was extracted with 3× ethyl acetate. The combined organic layer was dried over MgSO$_4$, filtered and evaporated under reduced pressure to give acid 98 mg (85%). ESI (M−H)$^−$=359.2.

Step (2k): A mixture of acid from (2j) (6 mg, 0.017 mmol), HATU (7 mg, 0.018 mmol), and DIEA (7 μL, 0.05 mmol) in 2 mL of DMF was stirred at room temperature for 5 min. Amine Preparation (B) (5.6 mg, 0.017 mmol) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified on preparative LC-MS (reverse phase HPLC) to afford the desired product. ESI (M+H)$^+$=679.36. $^1$H-NMR (CDCl$_3$) δ8.00 (d, J=5 Hz, 1H), 7.28-6.50 (m, 12H), 4.20-1.40 (m, 21H), 3.79 (s, 3H), 1.91 (s, 3H), 1.20-1.05 (m, 1H), 1.05-0.92 (m, 6H).

EXAMPLE 3

(2S)-2-(3(S)-Acetylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

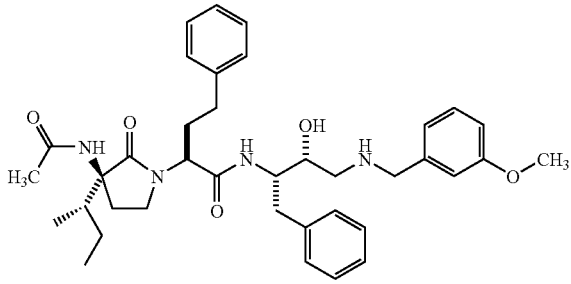

Step (3a): 20.0 mg of acid (0.056 mmol) from (2j), 3 mL of DMF, 9.4 mg HOBt (0.061 mmol) and 11.7 mg EDC (0.061 mmol) were mixed and stirred for 5 min. 22 mg (0.055 mmol) of amine Preparation (D) and DIEA (16 μL, 0.114 mmol) were then added and the mixture was stirred for overnight. The reaction solution was diluted with ethyl acetate and washed with 5% citric acid and 5% NaHCO$_3$, dried over MgSO$_4$, filtered, and the filtrate was evaporated. The residue was treated with 2 mL of TFA/CH$_2$Cl$_2$ (1:1) at rt for 30 min and evaporated under reduced pressure. The residue was purified by preparative LC-MS to give the product 9.1 mg (27%). ESI (M+H)$^+$=643.38. $^1$H-NMR (CDCl$_3$) δ7.91-7.88 (d, J=9.1 Hz, 1H), 7.28-6.88 (m, 14H), 6.24 (br, 1H), 4.20-4.00 (m, 2H), 3.79 (s, 3H), 3.41-2.00 (m, 20H), 1.91 (s, 3H), 1.80-1.05 (m, 3H), 1.02-0.87 (m, 6H).

EXAMPLE 4

2(S)-(3(S)-((S)-sec-butyl)-2-oxo-3-propionylamino-pyrrolidin-1-yl)-N—(S)-{1(R)-[1-hydroxy-2-(3-methoxy-benzylamino)-ethyl]-3-methyl-butyl}-4-phenyl-butyramide

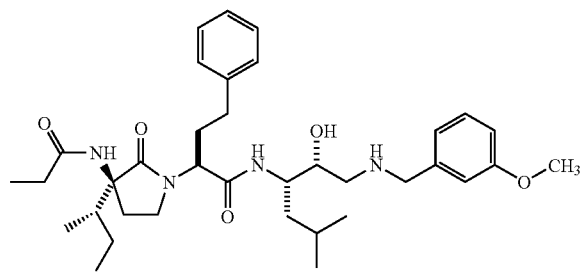

Step (4a): A mixture of propionic acid (0.12 g, 1.61 mmol), HATU (0.57 g, 1.5 mmol), and DIEA (450 μL, 2.58 mmol) in 3 mL of DMF was stirred at room temperature for 10 min. Amine (0.30 g, 0.90 mmol) from (2h) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified by chromatography on silica gel to provide amide 0.26 g (74%). ESI (M+H)$^+$=389.56. $^1$H-NMR (CDCl$_3$) δ 7.31-7.16 (m, 5H), 6.25 (br, 1H), 4.85-4.80 (m, 1H), 3.73-1.50 (m, 11H), 3.69 (s, 3H), 1.20-0.80 (m, 11H).

Step (4b): Compound (0.26 g, 0.67 mmol) from (4a) was dissolved in 5 mL of THF. 5 mL 1N LiOH was added and the mixture was stirred for 2 h. It was then diluted with ethyl acetate, acidified with 1N HCl. The aqueous layer was extracted with 3× ethyl acetate. The combined organic layer was dried over MgSO$_4$, filtered and evaporated under reduced pressure to give acid 0.21 g (84%). ESI (M+H)$^+$=375.59.

Step (4c): A mixture of acid from (4b) (37.4 mg, 0.1 mmol), HATU (76 mg, 0.2 mmol), and DIEA (70 μL, 0.4 mmol) in 2 mL of DMF was stirred at room temperature for 10 min. Amine Preparation (E) (45 mg, 0.15 mmol) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was treated with 2 mL of TFA/CH$_2$Cl$_2$ (1:3) at rt for 10 min and evaporated under reduced pressure. The residue was purified on preparative LC-MS (reverse phase HPLC) to afford the desired product 36.8 mg (59%). ESI (M+H)$^+$=623.64. $^1$H-NMR (CD$_3$OD) δ8.00-6.80 (m, 9H), 4.55-1.40 (m, 22H), 3.75 (s, 3H), 1.30-0.70 (m, 15H).

EXAMPLE 5

(2S)-2-(3-((S)-sec-butyl)-3-(2-methoxy-acetylamino)-2-oxo-pyrrolidin-1-yl)-N—(S)-{1(R)-[1-hydroxy-2-(3-methoxy-benzylamino)-ethyl]-3-methyl-butyl}-4-phenyl-butyramide

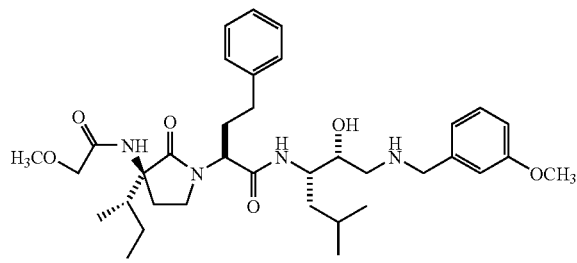

Step (5a): A mixture of methoxyacetic acid (0.14 g, 1.56 mmol), HATU (0.57 g, 1.5 mmol), and DIEA (450 μL, 2.58 mmol) in 3 mL of DMF was stirred at room temperature for 10 min. Amine (0.30 g, 0.90 mmol) from (2h) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified by chromatography on silica gel to provide amide 0.27 g (75%). ESI (M+H)$^+$=405.53.

$^1$H-NMR (CDCl$_3$) δ7.30-7.18 (m, 5H), 7.04 (br, 1H), 4.89-4.84 (m, 1H), 3.98-1.80 (m, 9H), 3.92 (s, 2H), 3.69 (s, 3H), 3.43 (s, 3H), 1.65-1.10 (m, 2H), 1.05-0.90 (m, 6H).

Step (5b): Compound (0.27 g, 0.69 mmol) from (5a) was dissolved in 5 mL of THF. 5 mL 1N LiOH was added and the mixture was stirred for 2 h. It was then diluted with ethyl acetate, acidified with 1N HCl. The aqueous layer was extracted with 3× ethyl acetate. The combined organic layer was dried over MgSO$_4$, filtered and evaporated under reduced pressure to give acid 0.22 g (82%). ESI (M+H)$^+$=391.59.

Step (5c): A mixture of acid from (5b) (39 mg, 0.1 mmol), HATU (76 mg, 0.2 mmol), and DIEA (70 μL, 0.4 mmol) in 2 mL of DMF was stirred at room temperature for 10 min. Amine Exmaple E (45 mg, 0.15 mmol) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was treated with 2 mL of TFA/CH$_2$Cl$_2$ (1:3) at rt for 10 min and evaporated under reduced pressure. The residue was purified on preparative LC-MS (reverse phase HPLC) to afford the desired product 24.2 mg (34%). ESI (M+H)$^+$=640.63.
$^1$H-NMR (CD$_3$OD) δ8.00-6.80 (m, 9H), 4.20-1.00 (m, 22H), 4.10 (s, 2H), 3.75 (s, 3H), 3.35 (s, 3H), 1.00-0.70 (m, 12H).

EXAMPLE 6

(2S)-2-(3(R)-Acetylamino-3(-cyclopropylmethyl)-2-oxo-pyrrolidin-1-yl)-N-[(1S,2R)-1-benzyl-2-hydroxy-3-(3-methoxy-benzylamino)-propyl]-4-phenyl-butyramide

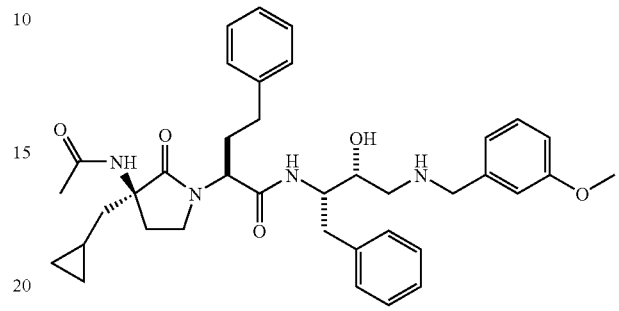

Step (6a): To 3.2 mL of diisopropylamine (22.75 mmol) in 30 mL of dry THF at −70° C. was added 9.1 mL of a 2.5 M solution of n-BuLi in hexanes (22.75 mmol), and the LDA thus formed was stirred for 15 min at that temperature. Separately, a 4.86 g portion (19 mmol) of tert-butyl 2-tert-butyl-4-methoxy-2,5-dihydro-1,3-imidazole-1-carboxylate (Boc-BDI, Seebach, D. and Hoffmann, M. (1998), *European Journal of Organic Chemistry* (7), 1337-1351.) was dissolved in 30 mL of dry THF and was also chilled to −70° C. The LDA was added via cannula to the Boc-BDI solution and the reaction solution was stirred for 40 min. Allyl iodide (1.82 mL, 19 mmol, freshly purified over alumina) was then added and the reaction solution was stirred at −70° C. for an additional hour. After this time, an additional 9.10 mL (22.75 mmol) of n-BuLi was added and reaction solution was stirred for 30 min. Cyclopropylmethyl bromide (1.83 g, 19 mmol, freshly purified over alumina) was then added and the reaction solution was brought to 0° C. and stirred at that temperature for 1 h. A saturated aqueous ammonium chloride solution (20 mL) was then added, and ether (200 mL) was added. The organic layer was separated and the aqueous layer was extracted with one additional equal portion of ether. The combined organic layers were dried and concentrated to an oil, which was purified by chromatography eluting with 5% ethyl acetate in hexanes to afford a 73% yield (4.85 g) of the desired product. ESI MS, (M+H)$^+$=351.6

Step (6b): The imidate from step (6a) (3.5 g, 10 mmol) was dissolved in 50 mL of a 9:1 solution of CH$_2$Cl$_2$ and TFA. The reaction solution was stirred at rt for 7 h. The solution was then neutralized with a satd. NaHCO$_3$ solution and 300 mL of CH$_2$Cl$_2$ was added. The organic layer was removed and the aqueous layer was extracted with an additional portion of CH$_2$Cl$_2$. The combined organic layers were dried and concentrated to an oil which was carried on to step (6c) without further purification.

Step (6c): The oil from step (6b) was dissolved in 300 mL of THF and 30 mL of a 15% solution of TFA in water was added. The reaction solution was stirred at rt for 4 days. The mixture was then extracted with ether (30 mL) and the ether was discarded. The aqueous layer was neutralized to pH 10 with a 10% aqueous solution of ammonium hydroxide, and the resulting solution was extracted 3× with 100 mL of ether. The combined organic layers were dried and concentrated to an oil (1 g, 54% from step (6b)) which was carried on to step (6d) without further purification. ESI MS, (M+H)$^+$=184.5

Step (6d): To 1 g of the amine from step (6c) (5.46 mmol) dissolved in 10 mL of CH$_2$Cl$_2$ was added 4 mL of a 2N solution of NaOH, followed by benzyl chloroformate (1.2 mL, 8.2 mmol). The reaction solution was stirred at rt for 18 h and then was diluted with 300 mL of CH$_2$Cl$_2$ and a satd. NaHCO$_3$ solution. The organic layer was separated, dried, and concentrated to an oil. Purification by chromatography eluting with 10-20% ethyl acetate in hexanes provided the protected quaternary amino acid ester (1.6 g, 92%). ESI MS, (M+H)$^+$=318.5

Step (6e): The ester from step (6d) 1.4 g (4.4 mmol) was dissolved in 25 mL of methanol and 1.85 g of LiOH (44 mmol) dissolved in 14 mL of water was added. The solution was transferred in to 11 3.5 mL microwave tubes and heated with a microwave to 120° C. for 360 seconds. The samples were then combined, and the methanol was removed by rotary evaporation. The reaction solution was diluted with 50 mL of water and 20 mL of ethyl acetate. The organic layer was separated and discarded. The aqueous layer was brought to pH 3 with 1N HCl and extracted with 2×100 mL of ethyl acetate. The combined organic layers were separated, dried, and concentrated to an oil (1.17 g, 86%) which was taken on without further purification. ESI MS, (M+H)$^+$=304.4.

Step (6f): The acid from step (6e) (1.17 g, 3.86 mmol) was dissolved in 30 mL of CH$_2$Cl$_2$ and 15 mL of DMF. Homophenylalanine methyl ester (0.89 g, 4.6 mmol) was added, followed by DIEA (2.7 mL, 15.4 mmol) and PyBOP (2.41 g, 4.6 mmol). The reaction solution was stirred at rt for 18 h, then diluted with water (20 mL) and extracted with two 200 mL portions of CH$_2$Cl$_2$. The combined organic layers were separated, dried, and concentrated to an oil. Purification by chromatography eluting with 20-50% ethyl acetate in hexanes provided 1.45 g (78%) of the desired product. $^1$H NMR (δ, representative) (7.1-7.4, m, 10 H, 2 phenyl groups), 5.6-5.75 (m, 2H, alkene), 3.67 (s, 3H, methyl ester).

Step (6g): 0.5 g (1.04 mmol) of the compound from step (6f) was dissolved in 10 mL of CH$_2$Cl$_2$ and chilled to −70° C. Ozone was introduced by bubbling through the solution until a blue color persisted. Dioxygen was then bubbled through the solution until the blue color dissipated. The reaction solution was then treated with triphenylphosphine (0.33 g, 1.25 mmol) and the solution was brought to rt and stirred for 2 h. The reaction solution was then cooled to 0° C. and 10 mL of 1:1 solution of TFA and triethylsilane was added. The reaction solution was stirred for 3 h, and then the solvent was removed. The resulting product was purified by chromatography eluting with 10-20 ethyl acetate in hexanes to provide 0.150 g of the desired lactam (31%). ESI MS, (M+H)+=465.5.

Step (6h): The lactam from step (6g) was dissolved in 20 mL of methanol and 30 mg of 10% palladium on carbon was added. The reaction solution was placed in a Parr apparatus under 50 psi of dihydrogen and shaken for 2 h. The catalyst was then removed by filtration and the reaction solution was concentrated to an oil (0.10 g, 100%) and taken on without further purification Step (6i): The amine from step (6h) (0.10 g, 0.30 mmol) was dissolved in 5 mL of DMF. Acetic acid (22 μL, 0.36 mmol), HATU (0.14 g, 0.36 mmol) and DIEA (0.2 mL, 1.2 mmol) were added and the reaction solution was stirred at rt for 18 h. The reaction solution was then diluted with 5 mL of water and extracted with 2×25 mL of ethyl acetate. The combined organic layers were washed with a 1N HCl solution (5 mL) and a satd. NaHCO$_3$ solution (5 mL), dried, and concentrated to an oil. The product was purified by chromatography eluting with 20-50% ethyl acetate in hexanes to provide 2 separate diastereomers at the lactam stereocenter (diastereomer 1, 20 mg, diastereomer 2, 30 mg, 50%). ESI MS, (M+H)$^+$=373.5

Step (6j): The lower-eluting diastereomer from step (6i) (30 mg, 0.080 mmol) was dissolved in 3 mL of THF and a solution of 33 mg (0.80 mmol) of lithium hydroxide dissolved in 0.5 mL of water was added. After stirring at rt for 3 h, 5 mL each of water and ethyl acetate were added and the organic layer was separated and discarded. The aqueous layer was brought to pH 3 with 1N HCl and the reaction solution was extracted with ethyl acetate (2×30 mL). The combined organic layers were separated, dried, and concentrated to an oil (18 mg, 94%) which was taken on without further purification. ESI MS, (M+H)$^+$=359.5

Step (6k): To 18 mg (0.05 mmol) of the acid from step (6j) in 2 mL of DMF was added 24 mg (0.055 mmol) of intermediate 6 dissolved in 1 mL of DMF. HATU (22 mg 0.055 mmol) and DIEA (17 μL, 0.1 mmol) were added, and the reaction solution was stirred at rt for 18 h. The solution was then diluted with water and extracted with 2×25 mL of ethyl acetate. The combined organic layers were washed with a 1N HCl solution (5 mL) and a satd. NaHCO$_3$ solution (5 mL), dried, and concentrated to an oil. The product was purified by chromatography eluting with 80-100% ethyl acetate in hexanes to provide 20 mg (50%) of the desired product. ESI MS, (M+H)$^+$=775.8

Step (6l): The compound from step (6k) (20 mg, 0.025 mmol) was dissolved in 8 mL of methanol and 13 mg of 5% palladium on carbon was added. The reaction solution was place in a Parr apparatus and hydrogenated at 50 psi for 3 h. The catalyst was removed by filtration and the resulting solution was concentrated to an oil. The product was purified by chromatography eluting with 10% methanol in ethyl acetate to provide 10 mg (62%) of the desired product. ESI MS, (M+H)$^+$=641.6. $^1$H NMR (δ) (7.05-7.26, m, 14H), (6.88, s, 1H), (6.22, s, 1H), (4.15-4.2, m, 1H), (4.09, q, 1H, J=7.0), (3.77, s, 3H), (3.6-3.7, m, 1H), (3.12-3.18, m, 1H), (3.08, q, 1H, J=8.7), (2.94, dd, 1H, J=4.1, 0.8), (2.71, d, 2H, J=5.1), (2.1-2.4, m, 11H), (1.98, s, 2H), (1.63, dd, 1H, J=5.5, 1.0), (1.48, dd, 1H, J=7.7, 1.0), (1.23, t, 1H, J=6.9), (0.62-0.67, m, 1H), (0.56, d, 2H, J=7.4), (0.15, m, 2H).

EXAMPLE 7

(2S)-2-(3(S)-Acetylamino-3(-cyclopropylmethyl)-2-oxo-pyrrolidin-1-yl)-N-[(1S,2R)-1-benzyl-2-hydroxy-3-(3-methoxy-benzylamino)-propyl]-4-phenyl-butyramide

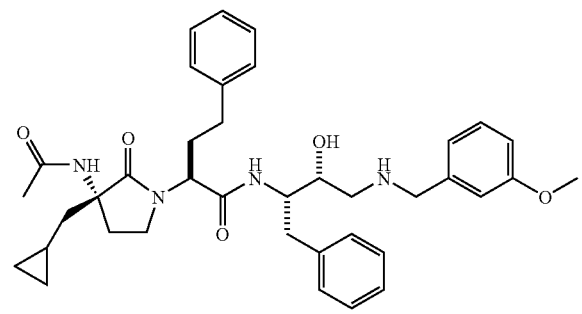

Following the general procedure for steps (6j-l) but using the higher eluting diastereomer from step (6i), the title compound was prepared. ESI MS, (M+H)$^+$=641.6.

EXAMPLE 8

(2S)-2-(3(S)-(2(S)-amino-5-carboxypentanoy-lamino)-3-((S)-sec-butyl)-2-oxo-pyrrolidin-1-yl)-N-[(1S,2R)-1-benzyl-2-hydroxy-3-(3-methoxy-benzy-lamino)-propyl]-4-phenyl-butyramide

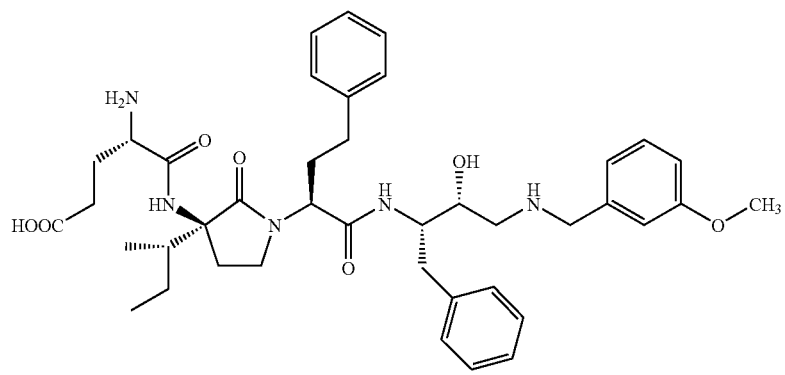

Step (8a): The lactam from step (2g) (2.0 g, 4.28 mmol) was dissolved in 100 mL of a 1:1 solution of THF and a 1 M lithium hydroxide solution. After 2 h at rt the reaction solution was concentrated to remove THF, and the resulting aqueous solution was acidified with HCL and extracted with ethyl acteate. The organic layers were combined, dried, and concentrated. The crude acid was purified by HPLC using the described standard conditions to provide 0.75 g (40%) of the purified material. ESI MS, $(M+H)^+=453.49$.

Step (8b): The acid from step (8a) (1.06 g, 2.35 mmol) was dissolved in 20 mL of DMF and treated with 1.64 mL (9.4 mmol) of DIEA and 2.31 g (6.1 mmol) of HATU. After the solution was stirred at rt for 10 min, the compound of Preparation (D) (1.0 g, 2.5 mmol) was added and the reaction solution was stirred at rt for 2 h. The reaction solution was diluted with water and extracted with 3 parts of a 2:1 solution of hexanes/DCM. The combined organic layers were dried and concentrated and the desired amide was isolated by chromatography eluting with a gradient of 40-60% ethyl acetate in hexanes to provide 1.99 g (97%). ESI MS, $(M+H)^+=835.31$.

Step (8c): A solution of the compound of Example (8b) (2.0 g, 2.34 mmol in Methanol (50 mL) was placed in a Parr apparatus and hydrogenated over 10% palladium on carbon (400 mg) at 60 psi for 24 h. The slurry was filtered through celite and the resulting solution was concentrated under reduced pressure to afford 1.5 g (91%) of the desired amine. ESI MS, $(M+H)^+=701.46$.

Step (8d): A solution of Boc-Glu(O-t-Bu)-OH (Bachem, 42 mg, 0.136 mmol) dissolved in DMF (0.6 mL) was treated with DIEA (63 µL, 0.36 mmol) and HATU (52 mg, 0.136 mmol). After 10 min, the amine from step (8c) (38 mg, 0.045 mmol) was added and the reaction solution was stirred at rt overnight. Water was then added, and the solution was extracted with 3 portions of ethyl acteate. The organic layers were combined and concentrated to a crude product, which was then dissolved in a 1:1 solution of TFA and DCM. After 2 h at rt, the solvents were removed and the residue was purified by preparative HPLC under the described conditions to provide 4.0 mg (12%) of the title compound of Example (8). ESI MS $(M+H)^+=730.52$. $^1$H NMR (300 MHz, CD$_3$OD) δ ppm 0.55 (d, J=6.59 Hz, 3 H), 0.95 (m, 5 H), 1.59 (m, 2 H), 1.91 (m, 2 H), 2.05 (m, 4 H), 2.51 (m, 6 H), 2.61 (s, 2 H), 2.82 (dd, J=12.81, 8.42 Hz, 2 H), 2.98 (m, 2 H), 3.15 (dd, J=14.28, 3.30 Hz, 2 H), 3.44 (d, J=3.66 Hz, 1 H), 3.74 (s, 2 H), 3.91 (m, 3 H), 4.13 (s, 3 H), 4.32 (dd, J=10.43, 4.94 Hz, 1 H), 6.85 (dd, J=8.06, 2.20 Hz, 1 H), 6.95 (d, J=7.69 Hz, 1 H), 6.99 (d, J=1.83 Hz, 1 H), 7.17 (m, 11 H), 8.01 (d, J=8.79 Hz, 1 H).

EXAMPLE 9

(2S)-2-(3(S)-(2-methoxy-acetylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

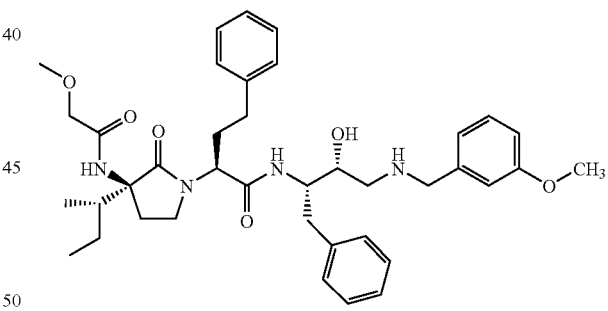

In a similar manner to the synthesis of the compound of Example (8), the amine from the compound of Example (8c) (55 mg, 0.1 mmol) was reacted with methoxyacetic acid and the Boc group was removed with 1:1 TFA/DCM to provide the compound of Example (9) (27 mg, 53%). ESI MS $(M+H)^+=673.42$ $^1$H NMR (300 MHz, CD$_3$OD) δ ppm 0.76 (d, J=6.59 Hz, 3 H), 0.95 (t, J=7.14 Hz, 3 H), 1.68 (s, 2 H), 1.90 (d, J=4.03 Hz, 1 H), 2.10 (m, 3 H), 2.50 (m, 3 H), 2.84 (m, 2 H), 3.10 (m, 2 H), 3.17 (dd, J=14.28, 3.66 Hz, 1 H), 3.34 (s, 3 H), 3.69 (d, J=2.20 Hz, 2 H), 3.75 (s, 3 H), 3.85 (m, 4 H), 4.11 (m, 4 H), 6.90 (dd, J=8.42, 2.56 Hz, 1 H), 6.96 (m, 2 H), 7.16 (m, 11 H), 7.68 (s, 1 H), 8.01 (d, J=8.79 Hz, 1 H).

EXAMPLE 10

(2S)-2-(3(S)-propionylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

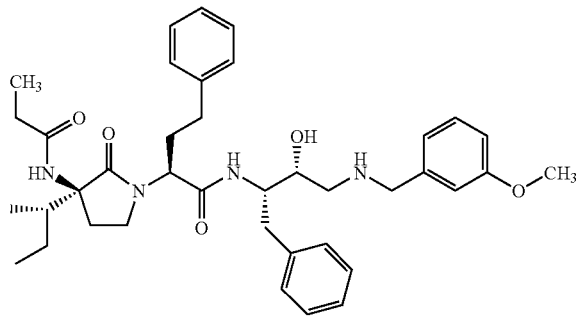

In a similar manner to the synthesis of the compound of Example (8), the amine from the compound of Example (8c) (55 mg, 0.1 mmol) was reacted with propionic acid and the Boc group was removed with 1:1 TFA/DCM to provide the compound of Example (10) (29 mg, 58%). ESI MS (M+H)$^+$=657.44

$^1$H NMR (300 MHz, Solvent) δ ppm 0.74 (d, J=6.96 Hz, 3H), 0.95 (t, J=6.96 Hz, 3 H), 1.05 (t, J=7.51 Hz, 3H), 1.63 (m, 2 H), 1.87 (m, 1 H), 2.07 (m, 2 H), 2.22 (m, 3 H), 2.45 (m, 1 H), 2.61 (m, 2 H), 2.85 (dd, J=12.63, 8.60 Hz, 2 H), 3.04 (m, 1 H), 3.11 (dd, J=14.28, 3.30 Hz, 1 H), 3.22 (dd, J=9.15, 3.30 Hz, 1H), 3.74 (s, 1 H), 3.74 (s, 3 H), 3.82 (dd, J=9.89, 4.76 Hz, 2 H), 3.90 (m, 1 H), 4.08 (m, 2 H), 4.14 (s, 2 H), 6.90 (dd, J=8.42, 2.56 Hz, 1 H), 6.96 (d, J=7.69 Hz, 1 H), 6.99 (d, J=2.20 Hz, 1 H), 7.17 (m, 11 H), 7.93 (s, 1 H), 8.09 (d, J=8.42 Hz, 1 H).

EXAMPLE 11

(2S)-2-(3(S)-acetylamino-3-((S)-sec-butyl)-2-oxo-pyrrolidin-1-yl)-N-[(1S,2R)-1-(2-fluorobenzyl)-2-hydroxy-3-(3-methoxy-benzylamino)-propyl]-4-phenyl-butyramide

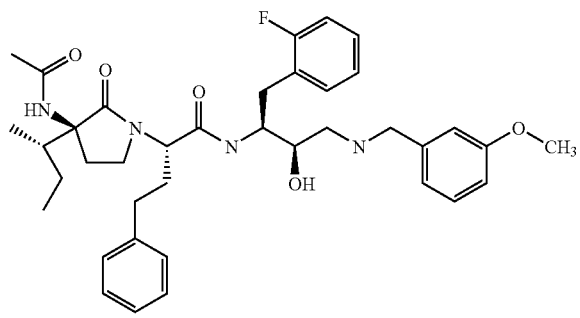

The acid of Example (2j) (5.0 mg, 0.014 mmol) was dissolved in 1 mL of DCM and coupled with the amine of Preparation (G) (20 mg, 0.06 mmol) using EDCl (0.06 mmol, 10 mg). After 2 h at rt, the solvent was removed and the crude compound was purified by preparative HPLC under the described standard conditions to provide 0.5 mg (7%) of the desired title compound of Example (11). ESI MS (M+H)$^+$=661.4

EXAMPLE 12

(2S)-2-(3(S)-acetylamino-3-((S)-sec-butyl)-2-oxo-pyrrolidin-1-yl)-N-[(1S,2R)-1-(2-fluorobenzyl)-2-hydroxy-3-(3-chloro-benzylamino)-propyl]-4-phenyl-butyramide

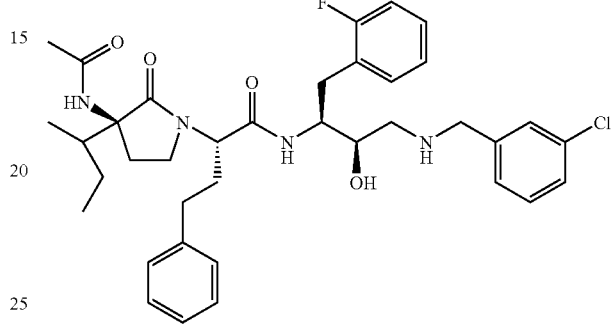

The acid of Example (2j) (5.0 mg, 0.014 mmol) was dissolved in 1 mL of DCM and coupled with the amine of Preparation (H2) (20 mg, 0.06 mmol) using EDCl (0.06 mmol, 10 mg). After 2 h at rt, the solvent was removed and the crude compound was purified by preparative HPLC under the described standard conditions to provide 0.5 mg (7%) of the desired title compound of Example (12). ESI MS (M+H)$^+$=665.4

EXAMPLE 13

(2S)-2-(3(S)-ethoxycarbonylamino-3-((S)-sec-butyl)-2-oxo-pyrrolidin-1-yl)-N-[(1S,2S)-1-benzyl-2-hydroxy-3-(3-methoxy-benzylamino)-propyl]-4-phenyl-butyramide

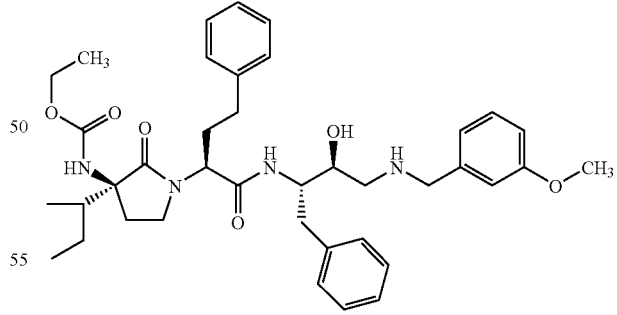

Step (13a): The lactam of Example (8a) (1.0 g, 2.34 mmol) was dissolved in 20 mL of DMF and treated with 1.6 mL (9.4 mmol) of DIEA and 2.3 g (6 mmol) of HATU. After the solution was stirred at rt for 10 min, the compound of Preparation (I) (1 g, 2.5 mmol) was added and the reaction solution was stirred at rt for 2 h. The reaction solution was diluted with water and extracted with 3 parts of a 2:1 solution of hexanes/DCM. The combined organic layers were dried and concentrated and the desired amide was isolated by chromatography eluting with a gradient of 40-60% ethyl acetate in hexanes to provide 1.98 g (96%) of the desired amide as a 2:1 mixture of diastereoisomers. ESI MS, (M+H)+=835.31.

Step (13b) A solution of the compound of Example (8b) (1.96 g, 2.25 mmol in Methanol (50 mL) was placed in a Parr apparatus and hydrogenated over 10% palladium on carbon (400 mg) at 60 psi for 24 h. The slurry was filtered through celite and the resulting solution was concentrated under reduced pressure to afford 1.5 g (91%) of the desired amine as a 2:1 mixture of diastereoisomers. ESI MS, (M+H)+=701.46.

Step (13c) The amine from step (13b) (60 mg, 0.085 mmol) was dissolved in 4 mL of CH₂Cl₂ and ethyl chloroformate (50 μL, 0.5 mmol) and DIEA (0.2 mL, 1.14 mmol) were added. After stirring at rt for 2 h, the reaction solution was treated with approximately 200 mg of polymer-bound trisamine resin (Argonaut Technologies) to remove excess chloroformate. The reaction solution was removed by filtration and the resin was washed with 3 additional 2 mL portions of DCM. The combined organic layers were dried and concentrated to provide a crude product which was treated directly with 2 mL of 1:1 TFA/DCM solution at rt for 1 h. Removal of the solvents and purification by prep HPLC under the standard reported conditions provided the compound of Example (13) (5.4 mg, 8%) as the earliest eluting diastereomer. ESI MS (M+H)+=673.32 ¹H NMR (500 MHz, Chloroform-d) δ ppm 0.93 (d, J=6.71 Hz, 3 H), 0.98 (d, J=7.02 Hz, 3 H), 1.16 (t, J=7.02 Hz, 3 H), 1.38 (d, J=6.71 Hz, 1 H), 1.43 (d, J=6.71 Hz, 1 H), 1.63 (d, J=13.73 Hz, 2 H), 1.85 (m, 5H), 2.18 (m, 3 H), 2.43 (m, 2 H), 2.82 (dd, J=12.36, 4.12 Hz, 1 H), 2.95 (m, 3 H), 3.12 (m, 1 H), 3.32 (td, J=9.46, 3.97 Hz, 1 H), 3.76 (s, 3 H), 3.91 (m, 1 H), 4.07 (m, 3 H), 5.19 (s, 1 H), 6.87 (dd, J=8.39, 2.29 Hz, 1 H), 6.92 (d, J=7.32 Hz, 1 H), 7.02 (s, 1 H), 7.08 (d, J=7.02 Hz, 1 H), 7.22 (m, 10 H), 7.62 (d, J=7.93 Hz, 1 H).

EXAMPLE 14

(2S)-2-(3(S)-ethoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

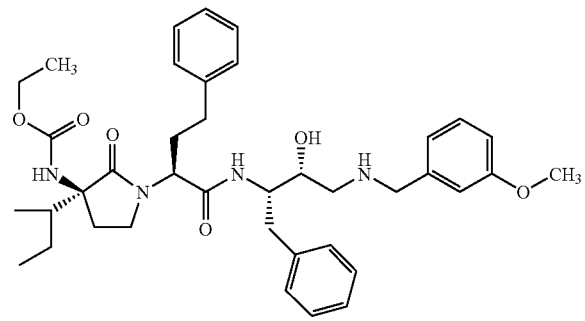

Purification of the compound of step (13c) by prep HPLC under the standard reported conditions provided the compound of Example (14) as the major, slower-eluting diastereomer (16.6 mg, 28%). ESI MS (M+H)+=673.4. ¹H NMR (500 MHz, Chloroform-d) δ ppm 0.89 (d, J=6.71 Hz, 3 H), 0.97 (t, J=7.32 Hz, 3 H), 1.11 (m, 1 H), 1.18 (t, J=7.02 Hz, 3 H), 1.60 (m, 1H), 1.69 (m, 1 H), 2.10 (m, 4 H), 2.21 (m, J=5.80 Hz, 1 H), 2.35 (m, 1 H), 2.42 (m, 1 H), 2.68 (dd, J=13.73, 10.07 Hz, 1 H), 2.82 (s, 1 H), 3.02 (m, 2 H), 3.15 (m, 2 H), 3.26 (d, J=14.34 Hz, 1 H), 3.51 (s, 1 H), 3.74 (d, J=4.58 Hz, 1 H), 3.76 (s, 3 H), 3.90 (m, 3 H), 4.06 (m, 2 H), 5.11 (s, 1 H), 6.87 (dd, J=8.24, 2.14 Hz, 1 H), 6.93 (d, J=7.32 Hz, 1 H), 7.04 (d, J=7.32 Hz, 2 H), 7.09 (m, 1 H), 7.22 (m, 9 H), 7.60 (s, 1 H).

EXAMPLE 15

(2S)-2-(3(S)-methoxycarbonylamino-3-((S)-sec-butyl)-2-oxo-pyrrolidin-1-yl)-N-[(1S,2S)-1-benzyl-2-hydroxy-3-(3-methoxy-benzylamino)-propyl]-4-phenyl-butyramide

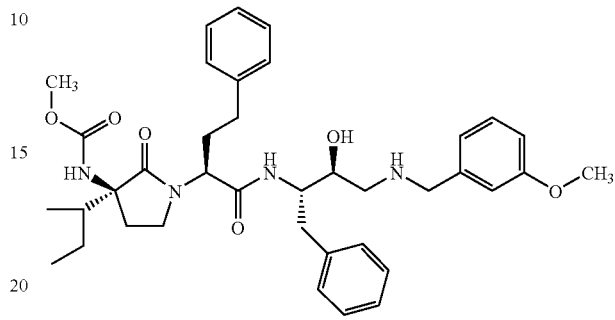

In a manner analogous to the synthesis of the compound of Example (13), but using methyl chloroformate, the title compound of Example (15) was prepared as the faster eluting diastereomer (3.3 mg, 4%). ESI MS (M+H)+=659.29. ¹H NMR (300 MHz, MeOH-d) δ ppm 0.99 (m, 10 H), 1.29 (s, 2 H), 1.74 (m, J=5.86 Hz, 4 H), 2.37 (d, J=8.42 Hz, 1 H), 2.79 (m, 2 H), 2.92 (m, 1 H), 3.03 (m, 2 H), 3.58 (s, 3 H), 3.59 (m, 2 H), 3.78 (s, 3 H), 3.80 (m, 2 H), 3.97 (m, 1 H), 4.15 (d, J=4.39 Hz, 1 H), 4.23 (m, 1 H), 6.99 (d, J=8.42 Hz, 2 H), 6.98 (m, 2 H), 7.28 (m, 10 H), 8.01 (s, 1 H).

EXAMPLE 16

(2S)-2-(3(S)-methoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

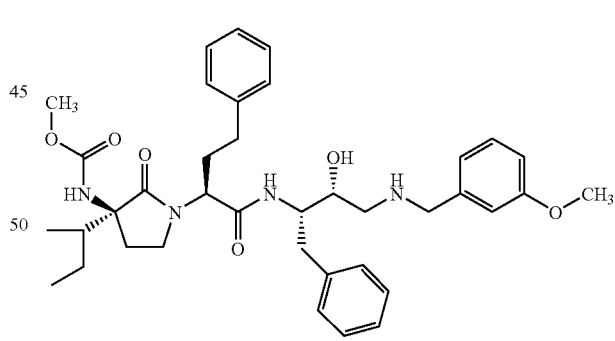

Purification of the compound of Example (15) by prep HPLC under the standard reported conditions provided the compound of Example (16) as the major, slower-eluting diastereomer (17.6 mg, 29%). ESI MS (M+H)+=659.4 ¹H NMR (300 MHz, MeOH-d) δ ppm 0.72 (d, J=7.34 Hz, 3 H), 0.95 (t, J=6.96 Hz, 3 H), 1.04 (m, 1 H), 1.65 (m, 2 H), 1.86 (m, 1 H), 2.12 (t, J=7.32 Hz, 2 H), 2.17 (m, 1 H), 2.47 (m, 1 H), 2.66 (m, 3 H), 2.88 (m, 2 H), 3.06 (m, 1 H), 3.15 (d, J=2.93 Hz, 1H), 3.20 (m, 1 H), 3.25 (d, J=8.06 Hz, 1 H), 3.58 (s, 3 H), 3.78 (s, 3 H), 3.88 (dd, J=8.24, 2.75 Hz, 2 H), 3.97 (m, 2 H), 4.17 (s, 2 H), 6.92 (dd, J=8.24, 2.38 Hz, 1 H), 7.01 (m, 2 H), 7.19 (m, 11 H), 8.01 (d, J=8.06 Hz, 1 H).

EXAMPLE 17

(2S)-2-(3(S)-propylureido-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

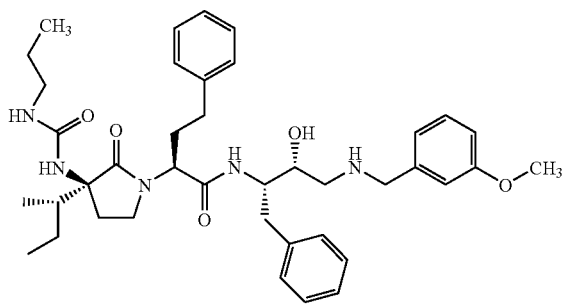

The amine from step (13b) (60 mg, 0.085 mmol) was dissolved in 1.5 mL of THF and propyl isocyanate (1000 μL, 10 mmol) was added. After stirring at rt for 48 h, the reaction solution was treated with 2 mL of DCM and approximately 200 mg of polymer-bound trisamine resin (Argonaut Technologies) to remove excess isocyanate. The reaction solution was removed by filtration and the resin was washed with 3 additional 2 mL portions of DCM. The combined organic layers were dried and concentrated to provide a crude product which was purified by Prep HPLC under the standard conditions described to provide 19 mg (30%) of the desired title compound of Example (17). ESI MS (M+H)$^+$=686.37. $^1$H NMR (300 MHz, Methanol-D) δ ppm 0.79 (d, J=6.59 Hz, 3 H), 0.85 (t, J=7.32 Hz, 3 H), 0.95 (t, J=7.14 Hz, 3 H), 1.06 (d, J=2.20 Hz, 1 H), 1.28 (m, 1H), 1.33 (dd, J=6.59, 2.56 Hz, 1 H), 1.42 (m, 2 H), 1.60 (m, 3 H), 2.09 (m, 3 H), 2.30 (m, 1 H), 2.46 (m, 1 H), 2.69 (m, 1 H), 2.84 (m, 2 H), 3.01 (t, J=6.77 Hz, 2 H), 3.07 (m, 1 H), 3.15 (m, 2 H), 3.69 (m, 2 H), 3.75 (s, 3 H), 3.90 (s, 3 H), 4.14 (s, 2 H), 6.91 (dd, J=8.06, 2.20 Hz, 1 H), 6.97 (m, 2 H), 7.17 (m, 11 H), 8.24 (d, J=8.05 Hz, 1 H).

EXAMPLE 18

(2S)-2-(3(S)-ethylureido-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

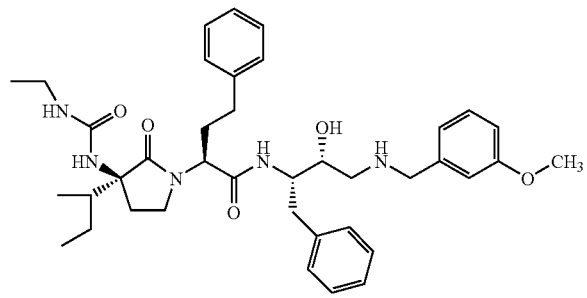

In a manner analogous to the synthesis of the compound of Example (17), but using ethyl isocyanate, the title compound of Example (18) was prepared as the major eluting diastereomer (3.3 mg, 4%). ESI MS (M+H)$^+$=672.39.

$^1$H NMR (300 MHz, Methanol-D) δ ppm 0.80 (d, J=6.59 Hz, 3 H) 0.96 (t, J=7.14 Hz, 3 H) 1.03 (t, J=7.32 Hz, 3 H) 1.17 (t, J=7.14 Hz, 1 H) 1.61 (m, 2 H) 1.90 (s, 1 H) 2.10 (m, 3 H) 2.30 (m, 1 H) 2.45 (m, 1 H) 2.63 (m, 3H) 2.87 (m, J=7.69 Hz, 1 H) 3.03 (d, J=6.96 Hz, 1 H) 3.08 (m, J=7.32 Hz, 3 H) 3.16 (m, 3 H) 3.68 (dd, J=9.89, 4.76 Hz, 1 H) 3.75 (s, 3 H) 3.88 (m, 3 H) 4.14 (s, 2 H) 6.91 (dd, J=7.87, 2.01 Hz, 1 H) 6.97 (m, 3 H) 7.18 (m, 10 H) 8.25 (d, J=7.32 Hz, 1 H)

EXAMPLE 19

(2S)-2-(3(S)-(trifluoroacetyl)amino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

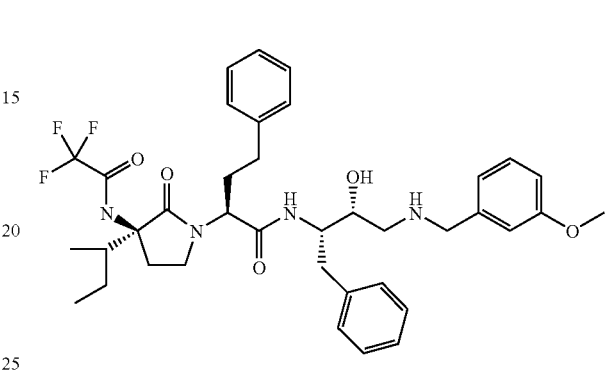

In a manner analogous to the synthesis of the compound of Example (17), but using trifluoroacetic anhydride, the title compound of Example (19) was prepared as the major eluting diastereomer (21.7 mg, 30%). ESI MS (M+H)$^+$=697.3

$^1$H NMR (300 MHz, Methanol-D) δ ppm 8.06 (s, 1 H), 7.57 (d, J=8.42 Hz, 1 H), 7.21 (m, 10 H), 6.98 (m, 4 H), 4.45 (dd, J=11.17, 3.48 Hz, 1 H), 4.32 (dd, J=11.17, 3.11 Hz, 1 H), 4.10 (m, 2 H), 3.96 (m, 1 H), 3.86 (ddd, J=13.36, 6.96, 6.77 Hz, 1 H), 3.77 (s, 3 H), 3.74 (dd, J=3.84, 2.01 Hz, 1 H), 2.98 (m, 3 H), 2.80 (dd, J=14.65, 12.08 Hz, 1 H), 2.40 (m, 3 H)) 2.07 (m, 1 H), 1.88 (m, 1 H), 1.49 (m, 1 H), 1.27 (dd, J=9.15, 6.59 Hz, 6 H), 1.04 (d, J=6.59 Hz, 2 H), 0.92 (t, J=6.96 Hz, 3 H).

EXAMPLE 20

(2S)-2-(3(S)-(3-3H-imidazol-4-yl-propionylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

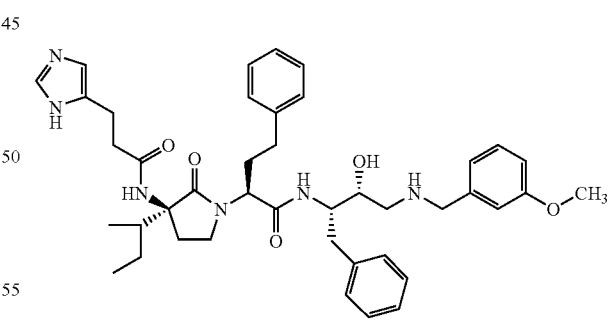

A solution of deaminohistidine (100 mg, 0.71 mmol) dissolved in 2 mL of DMF was treated with DIEA (200 μL, 1.15 mmol) and HATU (200 mg, 0.52 mmol). After 10 min at rt, a solution of 60 mg (0.085 mmol) of the amine of step (8b) was added and the reaction solution was stirred at rt for 3 h. A 5 mL portion of water was then added, and the mixture was extracted with three 5 mL portions of ethyl acetate. The organic layers were separated, dried, and concentrated, and the crude product was treated directly with 2 mL of 1:1 TFA/DCM solution at rt for 1 h. Removal of the solvents and purification by prep HPLC under the standard reported conditions provided the compound of Example (20) (13 mg, 20%) as the earliest eluting diastereomer. ESI MS (M+H)⁺=723.4. ¹H NMR (300 MHz, DEUTERIUM OXIDE) δ ppm 0.68 (d, J=6.59 Hz, 3 H), 0.95 (t, J=6.59 Hz, 3 H), 1.04 (d, J=18.68 Hz, 1 H), 1.63 (m, 3 H), 2.09 (m, 4 H), 2.45 (m, 1 H), 2.60 (m, 6 H), 2.86 (m, 1 H), 2.94 (m, 2 H), 3.03 (m, 1 H), 3.14 (dd, J=14.10, 3.11 Hz, 1 H), 3.22 (d, J=7.32 Hz, 1 H), 3.33 (q, J=4.27 Hz, 1 H), 3.75 (s, 3H), 3.84 (m, 1 H), 3.94 (m, 2 H), 4.09 (d, J=4.76 Hz, 1 H), 4.12 (d, J=5.13 Hz, 1 H), 4.16 (s, 1 H), 6.88 (dd, J=8.24, 1.65 Hz, 1 H), 6.99 (m, 2 H), 7.18 (m, 11H), 8.05 (m, 2 H), 8.62 (d, J=1.46 Hz, 1 H).

EXAMPLE 21

(2S)-2-(3(S)-(3-3H-imidazol-4-yl-propionylamino)-3-((S)-sec-butyl)-2-oxo-pyrrolidin-1-yl)-N-[(1S,2S)-1-benzyl-2-hydroxy-3-(3-methoxy-benzylamino)-propyl]-4-phenyl-butyramide

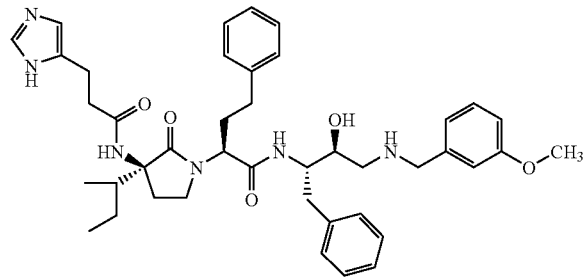

Purification of the compound of Example (20) by prep HPLC under the standard reported conditions provided the compound of Example (21) as the minor, slower-eluting diastereomer (9.0 mg, 14%). ESI MS (M+H)⁺=723.4. ¹H NMR (500 MHz, CHLOROFORM-D) δ ppm 0.89 (d, J=6.41 Hz, 3 H), 0.94 (t, J=7.32 Hz, 3 H), 1.08 (s, 2 H), 1.60 (m, 2 H), 1.73 (m, 2 H), 2.10 (m, 3 H), 2.24 (d, J=8.24 Hz, 1 H), 2.35 (m, 1 H), 2.46 (m, 2 H), 2.64 (m, 2 H), 2.89 (m, J=5.80 Hz, 1 H), 2.96 (m, 2 H), 3.07 (d, J=15.26 Hz, 2 H), 3.21 (d, J=4.58 Hz, 2 H), 3.46 (s, 1 H), 3.72 (s, 3 H), 3.98 (m, 4 H), 6.84 (dd, J=8.24, 2.14 Hz, 1 H), 6.90 (d, J=7.32 Hz, 1 H), 7.02 (m, 4 H), 7.19 (m, 8 H), 7.52 (dd, J=8.42, 4.39 Hz, 1 H), 8.47 (dd, J=8.42, 1.47 Hz, 1 H), 8.75 (dd, J=4.58, 1.28 Hz, 1 H), 9.35 (s, 1 H).

EXAMPLE 22

(2S)-2-(3(S)-(2-aminoacetylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

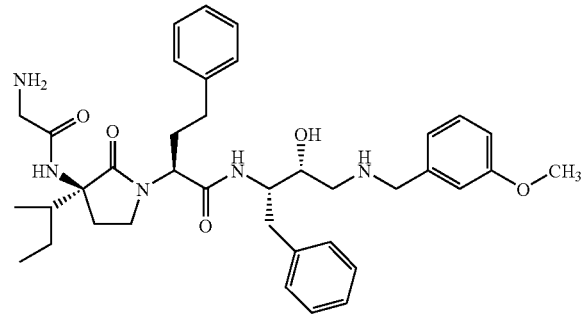

In a manner analogous to the synthesis of the compound of Example (20), but using N-Boc glycine, the title compound of Example (22) was prepared as the major, faster-eluting dias-tereomer (19.9 mg, 31%). ESI MS (M+H)⁺=658.4 ¹H NMR (300 MHz, CD₃OD) δ ppm 0.59 (d, J=6.59 Hz, 3 H), 0.99 (m, 5 H), 1.60 (m, 3 H), 1.77 (m, 1 H), 1.93 (m, 1 H), 2.15 (m, 2 H), 2.44 (m, 2 H), 2.66 (m, 2 H), 2.84 (m, 2 H), 3.03 (m, 1 H), 3.20 (dd, J=14.28, 3.30 Hz, 1 H), 3.45 (m, J=9.89, 9.89, 4.03 Hz, 1 H), 3.66 (s, 2 H), 3.76 (s, 3 H), 3.82 (m, 1 H), 4.00 (m, 2 H), 4.17 (s, 2 H), 4.39 (dd, J=10.07, 5.31 Hz, 1 H), 6.85 (dd, J=8.06, 1.83 Hz, 1H), 6.98 (d, J=7.69 Hz, 2 H), 7.03 (d, J=1.83 Hz, 1H), 7.23 (m, 11 H), 8.08 (d, J=8.79 Hz, 1 H).

EXAMPLE 23

(2S)-2-(3(S)—(2-aminoacetylamino)-3-((S)-sec-butyl)-2-oxo-pyrrolidin-1-yl)-N-[(1S,2S)-1-benzyl-2-hydroxy-3-(3-methoxy-benzylamino)-propyl]-4-phenyl-butyramide

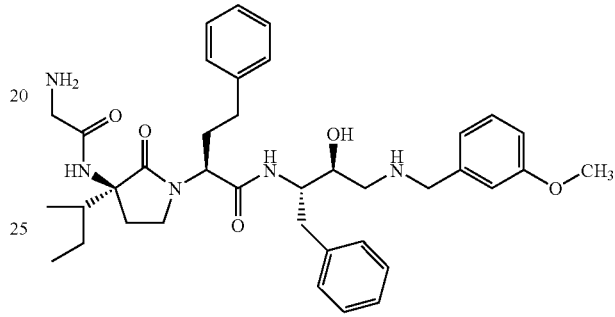

Purification of the compound of Example (22) by prep HPLC under the standard reported conditions provided an enriched sample of the compound of Example (23) as the minor, slower-eluting diastereomer (2.1 mg, 3%) contaminated with the compound of Example (22) (~2:1 favoring the compound of Example (23). ESI MS (M+H)⁺=658.4 ¹H NMR (300 MHz, CD₃OD) δ ppm 0.96 (t, J=7.14 Hz, 3 H), 1.08 (d, J=6.59 Hz, 3 H), 1.52 (m, 2H), 1.75 (dd, J=8.24, 6.77 Hz, 2 H), 2.30 (m, 6 H), 2.54 (m, 2 H), 2.97 (m, 3 H), 3.12 (m, 2 H), 3.76 (m, 1 H), 3.80 (s, 3 H), 3.83 (s, 1 H), 3.96 (m, 1 H), 4.08 (m, 1 H), 4.18 (m, 2 H), 4.36 (dd, J=11.35, 2.56 Hz, 1 H), 4.46 (dd, J=11.35, 3.30 Hz, 1 H), 6.99 (m, 1H), 7.06 (dd, J=6.23, 2.20 Hz, 2 H), 7.12 (dd, J=7.14, 1.65 Hz, 2 H), 7.26 (m, 11 H), 7.77 (d, J=8.79 Hz, 1H).

EXAMPLE 24

(2S)-2-(3(S)-(3-hydroxypropionylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

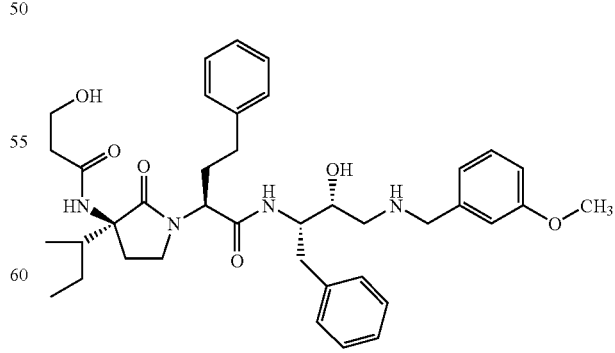

In a manner analogous to the synthesis of the compound of Example (20), but using 3-hydroxypropionic acid, the title compound of Example (24) was prepared (10.6 mg, 16%). ESI MS (M+H)⁺=673.4. ¹H NMR (300 MHz, CD₃OD) δ ppm 0.80 (d, J=6.59 Hz, 3 H), 0.99 (t, J=6.96 Hz, 3 H), 1.66 (d, J=6.59 Hz, 3 H), 2.13 (m, 2H), 2.48 (m, 2 H), 2.63 (m, 2 H), 2.88 (m, 2 H), 3.11 (m, 2 H), 3.21 (m, 2 H), 3.67 (m, 2 H), 3.75 (d, J=2.56 Hz, 1 H), 3.77 (s, 2 H), 3.78 (s, 3 H), 3.88 (m, 3 H), 3.97 (s, 2 H), 4.15 (dd, J=8.79, 5.86 Hz, 2H), 6.93 (dd, J=8.24, 2.38 Hz, 1 H), 7.01 (m, 2 H), 7.21 (m, 11 H), 8.10 (m, 2 H).

EXAMPLE 25

(2S)-2-(3(S)-(4-hydroxybutyrylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide

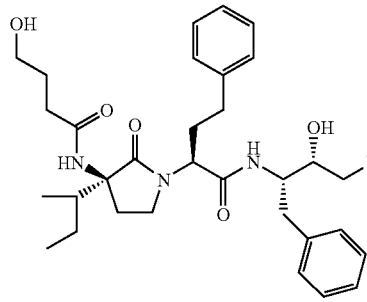

In a manner analogous to the synthesis of the compound of Example (20), but using 4-hydroxybutyric acid, the title compound of Example (25) was prepared (11.8 mg, 18%). ESI MS (M+H)$^+$=687.4. $^1$H NMR (300 MHz, CD$_3$OD) δ ppm 0.75 (m, 1 H), 0.76 (d, J=6.59 Hz, 3 H), 0.97 (t, J=6.77 Hz, 3 H), 1.07 (m, 1 H), 1.67 (m, 3H), 1.77 (m, 3 H), 1.98 (m, 1 H), 2.07 (m, 3 H), 2.21 (dd, J=9.70, 4.94 Hz, 1 H), 2.31 (m, 3 H), 2.46 (m, 2H), 2.63 (m, 2 H), 2.84 (m, 3 H), 3.04 (d, J=1.83 Hz, 1 H), 3.10 (dd, J=7.69, 2.93 Hz, 1 H), 3.17 (m, 1 H), 3.24 (dd, J=9.34, 5.68 Hz, 2 H), 3.32 (s, 1 H), 3.54 (td, J=6.41, 2.20 Hz, 2 H), 3.77 (s, 3 H), 3.84 (dd, J=10.07, 4.58 Hz, 1 H), 3.90 (m, 2 H), 3.96 (s, 1 H), 4.10 (m, 2 H), 4.16 (s, 2 H), 4.36 (t, J=6.41 Hz, 1H), 6.91 (dd, J=8.42, 2.56 Hz, 1 H), 6.99 (m, 2 H), 8.02 (d, J=8.79 Hz, 1 H), 8.09 (m, 1 H).

EXAMPLE 26

(2S)-2-(3(S)-(ethylsulfonamido)-3-((S)-sec-butyl)-2-oxo-pyrrolidin-1-yl)-N-[(1S)-1-benzyl-2-hydroxy-3-(3-methoxy-benzylamino)-propyl]-4-phenyl-butyramide

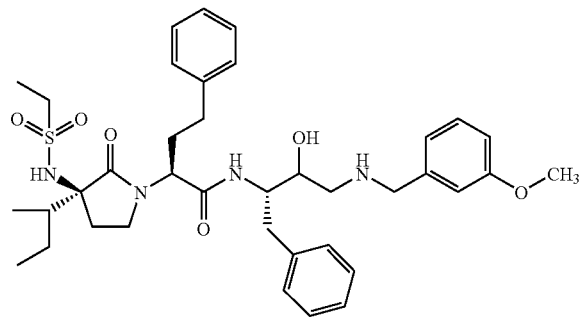

The amine from step (13b) (60 mg, 0.085 mmol) was dissolved in 4 mL of DCM and ethyl sulfonyl chloride (15 µL, 0.158 mmol), DIEA (100 µL, 0.63 mmol), and a catalytic amount of DMAP was added. The reaction solution was heated to reflux temperature for 3 h. The solution was cooled, and the solvents were removed, and the residue was directly deprotected with 4 mL of a 1:1 solution of TFA in DCM for 1 h at rt, followed by removal of the solvents. Purification of the residue by prep LC/MS under the standard described conditions provided the compound of Example (26) as a 1.3:1 mixture of diastereomers at the alcohol center (16.7 mg, 25%). ESI MS (M+H)$^+$=693.4. $^1$H NMR (300 MHz, CD$_3$OD) δ ppm 0.67 (d, J=6.96 Hz, 1 H), 0.97 (m, 6 H), 1.25 (t, J=7.32 Hz, 3 H), 1.93 (m, 3 H), 2.19 (m, 1 H), 2.36 (m, 1 H), 2.54 (m, 2 H), 2.67 (m, 1 H), 2.76 (q, J=7.44 Hz, 2 H), 2.94 (m, 2 H), 3.43 (m, 3H), 3.61 (m, 1 H), 3.72 (d, J=6.96 Hz, 2 H), 3.75 (s, 2 H), 3.94 (s, 3 H), 4.10 (d, J=3.66 Hz, 1 H), 4.17 (d, J=3.66 Hz, 1 H), 4.56 (m, 1 H), 4.68 (dd, J=9.52, 4.76 Hz, 1 H), 5.46 (d, J=10.25 Hz, 1 H), 6.80 (dd, J=8.42, 2.56 Hz, 1 H), 6.87 (d, J=5.86 Hz, 1 H), 6.97 (m, 4 H), 7.22 (m, 8 H).

EXAMPLE 27

(2S)-2-(3(S)-(propylsulfonamido)-3-((S)-sec-butyl)-2-oxo-pyrrolidin-1-yl)-N-[(1S)-1-benzyl-2-hydroxy-3-(3-methoxy-benzylamino)-propyl]-4-phenyl-butyramide

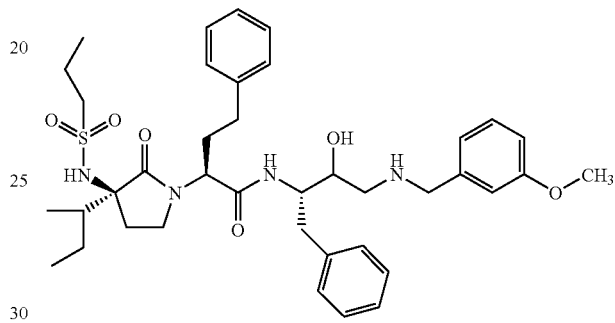

In a manner similar to the synthesis of the compound of Example (26), but using propylsulfonyl chloride the title compound of Example (27) was prepared (24.3 mg, 37%) as a 1:1 mixture of diastereomers at the alcohol center. ESI MS (M+H)$^+$707.4. $^1$H NMR (300 MHz, CD$_3$OD) δ ppm 0.58 (m, 1 H), 0.67 (d, J=6.59 Hz, 1 H), 0.97 (m, 8 H), 1.76 (m, 2H), 1.94 (m, 3 H), 2.35 (m, 1 H), 2.54 (m, 2 H), 2.72 (m, 2 H), 2.82 (m, 1 H), 2.96 (m, 1 H), 3.11 (dd, J=13.36, 6.04 Hz, 1 H), 3.40 (m, 3 H), 3.74 (m, 4 H), 3.93 (m, 3 H), 4.16 (m, 2 H), 4.38 (m, 1 H), 4.55 (m, 1 H), 4.68 (dd, J=9.52, 4.76 Hz, 1 H), 5.10 (m, 1 H), 5.46 (d, J=9.52 Hz, 1 H), 6.80 (dd, J=8.06, 2.20 Hz, 1H), 6.95 (m, 4 H), 7.22 (m, 9 H).

EXAMPLE 28

(2S)-2-(3(S)-acetylamino-3-(isobutyl)-2-oxo-pyrrolidin-1-yl)-N-[(1S,2R)-1-benzyl-2-hydroxy-3-(3-methoxy-benzylamino)-propyl]-4-phenyl-butyramide

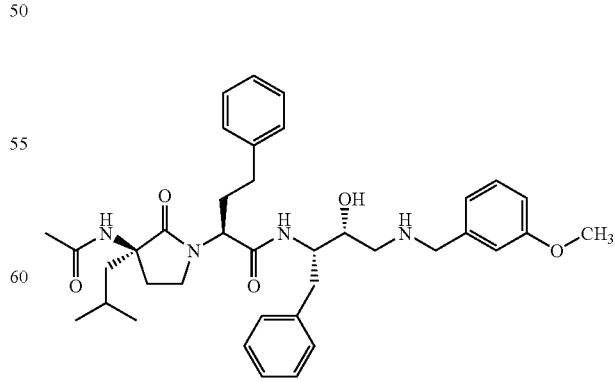

In a manner similar to the synthesis of the compound of Example (3), but using the γ-lactam prepared from L-Leucine the title compound of Example (28) was prepared. ESI MS (M+H)⁺=243.4 ¹H NMR (300 MHz, CD₃OD) δ ppm 1.02 (d, J=6.59 Hz, 6 H), 1.50 (dd, J=14.46, 7.14 Hz, 1 H), 1.68 (dd, J=14.28, 5.49 Hz, 1H), 1.83 (dd, J=12.27, 6.41 Hz, 1 H), 1.92 (s, 3 H), 2.05 (m, 2 H), 2.24 (dd, J=10.25, 6.59 Hz, 2 H), 2.34 (s, 5 H), 2.64 (dd, J=13.91, 10.62 Hz, 1 H), 2.89 (s, 1 H), 3.10 (s, 1 H), 3.19 (m, 2 H), 3.28 (dd, J=14.46, 4.21 Hz, 1 H), 3.41 (dd, J=8.24, 6.77 Hz, 1 H), 3.78 (s, 3 H), 4.10 (d, J=4.39 Hz, 3 H), 5.98 (s, 1 H), 6.91 (m, 2 H), 7.03 (d, J=8.42 Hz, 2 H), 7.10 (m, J=8.06 Hz, 1 H), 7.23 (m, 9 H), 7.75 (d, J=9.15 Hz, 1H).

EXAMPLE 29

(2S)-2-(3(S)-acetylamino-3-((S)-sec-butyl)-2-oxo-pyrrolidin-1-yl)-N-[(1S,2R)-1-benzyl-2-hydroxy-3-(3-chloro-benzylamino)-propyl]-4-phenyl-butyramide

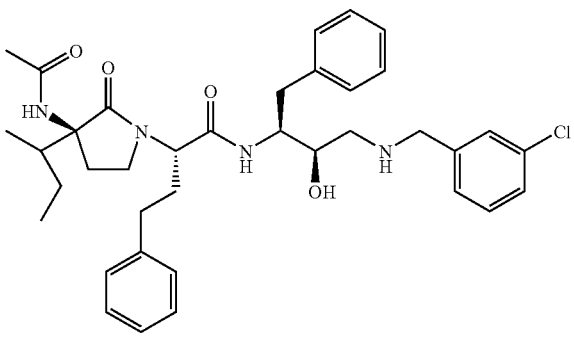

Following the general procedure for the synthesis of the compound of Example (3) but using the intermediate of Preparation (J) the title compound was prepared. Purification by prep HPLC under the standard described conditions provided 6.5 mg of the title compound of Example (30) as the TFA salt. ESI MS (M+H)⁺=647.7

EXAMPLE 30

(2S)-2-(3(S)-acetylamino-3-((S)-sec-butyl)-2-oxo-pyrrolidin-1-yl)-N-[(1S,2R)-1-benzyl-2-hydroxy-3-(propargylamino)-propyl]-4-phenyl-butyramide

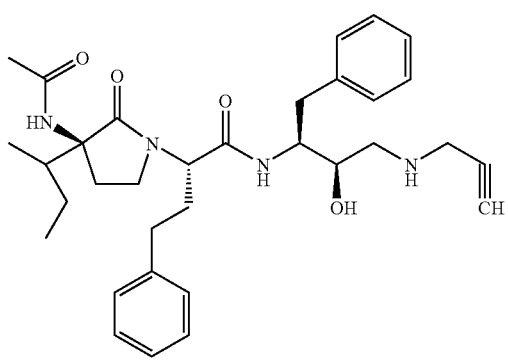

Following the general procedure for the synthesis of the compound of Example (3) but using the intermediate of Preparation (K) the title compound was prepared. Purification by prep HPLC under the standard described conditions provided 2.0 mg of the title compound of Example (30) as the TFA salt. ESI MS (M+H)⁺=561

EXAMPLE 31

(2S)-2-(3(S)-acetylamino-3-((S)-sec-butyl)-2-oxo-pyrrolidin-1-yl)-N-[(1S,2R)-1-benzyl-2-hydroxy-3-(cyclopropylmethyl)amino-propyl]-4-phenyl-butyramide

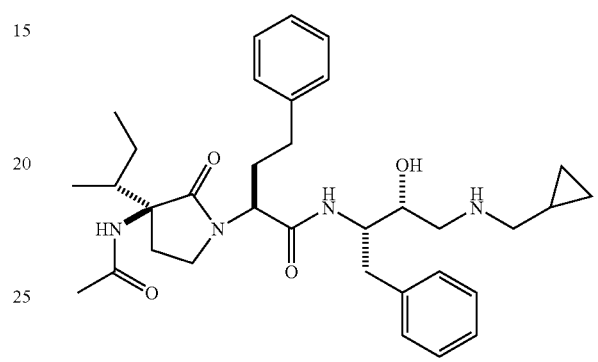

Following the general procedure for Example (3), but using the intermediate of Preparation (L) the title compound was prepared and isolated as a white solid TFA salt (11.6 mg) in a 35% yield. LC-MS (column=XTERRA C18 S7, 3×50 mm, start % B=0, final % B=100, gradient time=2 min, flow rate=5 ml/min) m/e 578.51 (M+H)⁺, t_R 1.46 min.

EXAMPLE 32

(2S)-2-(3(S)-acetylamino-3-(isobutyl)-2-oxo-pyrrolidin-1-yl)-N-[(1S,2R)-1-benzyl-2-hydroxy-3-(cyclopropylmethyl)amino-propyl]-4-phenyl-butyramide

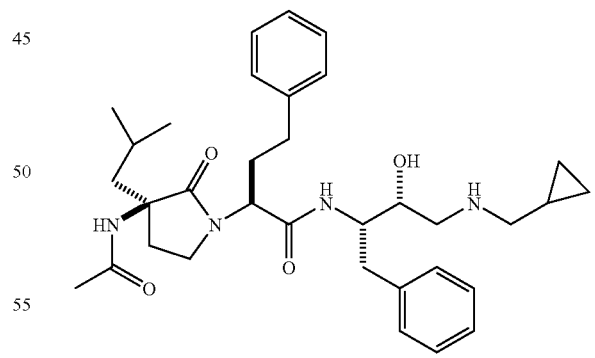

Following the general procedure for Example (3), but using the lactam from Example (28) and the amine of intermediate (L) the title compound was prepared and isolated as a white solid TFA salt (6.3 mg) in a 29% yield. LC-MS (column=XTERRA C18 S7, 3×50 mm, start % B=0, final % B=100, gradient time=2 min, flow rate=5 ml/min) m/e 577.49 (M+H)⁺, t_R 1.52 min. ¹H NMR (400 MHz, CHLOROFORM-D) δ ppm 0.32 (m, 3 H) 0.64 (d, J=7.58 Hz, 3 H) 1.02 (m, 2 H) 1.52 (m, 1 H) 1.68 (m, 1 H) 1.84 (m, 1 H) 2.23 (m, 13 H) 3.33

(m, 8H) 3.88 (m, 1 H) 4.13 (m, 1 H) 6.06 (m, 1 H) 7.15 (m, 10 H) 7.80 (m, 1 H) 8.85 (s, 1 H) 9.23 (s, 1 H).

EXAMPLE 33

(2S)-2-(3(S)-acetylamino-3-((S)-sec-butyl)-2-oxo-pyrrolidin-1-yl)-N-[(1S,2R)-1-benzyl-2-hydroxy-3-(3,5-difluorobenzylamino)-propyl]-4-phenyl-butyramide

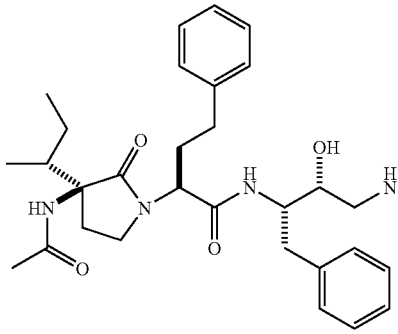

Following the general procedure for Example (3), but using the intermediate of Preparation (M) the title compound as a TFA salt was obtained as a pale-yellow solid (10.3 mg) in a 6% yield. LC-MS (column=XTERRA C18 S7, 3×50 mm, start % B=0, final % B=100, gradient time=2 min, flow rate=5 ml/min) m/e 649.52 (M+H)$^+$, $t_R$ 1.59 min. $^1$H NMR (400 MHz, CHLOROFORM-D) δ ppm 0.93 (m, 6 H) 1.14 (m, 1 H) 1.57 (m, 1 H) 1.73 (m, 1 H) 1.94 (s, 3 H) 2.09 (m, J=6.60 Hz, 2 H) 2.30 (m, 2 H) 3.15 (m, 13 H) 4.13 (m, 2 H) 6.10 (m, 1 H) 6.82 (m, 1 H) 7.16 (m, 12 H) 7.93 (s, 1H).

EXAMPLE 34

(2S)-2-(3(S)-acetylamino-3-((S)-sec-butyl)-2-oxo-pyrrolidin-1-yl)-N-[(1S,2R)-1-benzyl-2-hydroxy-3-((3-trifluoromethylbenzyl)amino)-propyl]-4-phenyl-butyramide

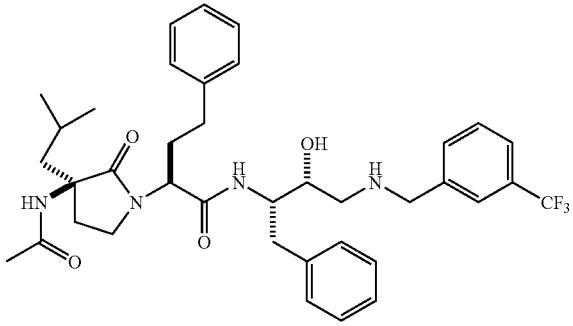

Following the general procedure for Example (3), but using the intermediate of Preparation (N) the title compound as a TFA salt was obtained as a white solid (15.3 mg) in 49% yield. LC-MS (column=XTERRA C18 S7, 3×50 mm, start % B=0, final % B=100, gradient time=2 min, flow rate=5 ml/min) m/e 681.54 (M+H)$^+$, $t_R$ 1.69.min. $^1$H NMR (400 MHz, CHLOROFORM-D) δ ppm 0.96 (m, 7 H) 1.48 (dd, J=14.43, 6.85 Hz, 1 H) 1.66 (m, 1 H) 1.81 (m, 4 H) 2.05 (m, 2H) 2.26 (m, 4 H) 2.63 (dd, J=13.82, 10.39 Hz, 1 H) 3.11 (m, 6 H) 3.43 (m, 1 H) 3.84 (m, 1 H) 4.16 (m, 4H) 6.00 (m, 1 H) 7.06 (m, 3 H) 7.21 (m, 6 H) 7.47 (t, J=7.70 Hz, 1 H) 7.67 (m, 4 H).

EXAMPLE 35

2-(3(S)-Acetylamino-3(S)-isobutyl-2-oxo-pyrrolidin-1-yl)-N-[(1S,2R)-1-benzyl-2-hydroxy-3-benzylamino-propyl]-4-phenyl-butyramide

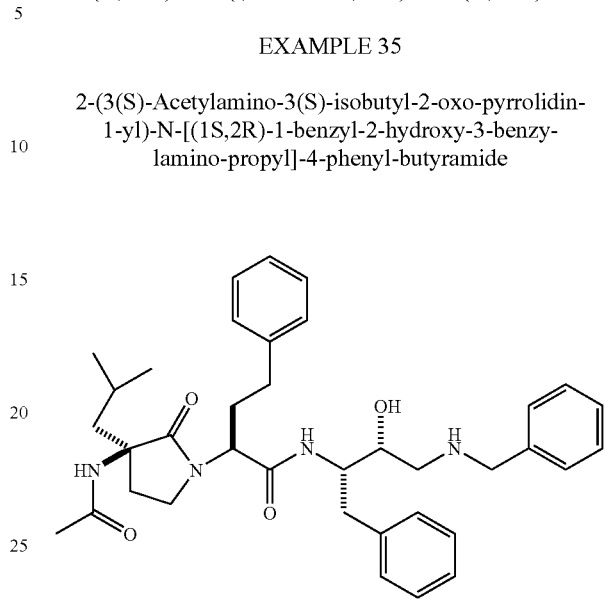

Following the general procedure for Example (3), but using the intermediate of Preparation (O), the title compound as a TFA salt was obtained as a beige solid (29.2 mg) in 43% yield. LC-MS (column=XTERRA C18 S7, 3×50 mm, start % B=0, final % B=100, gradient time=2 min, flow rate=5 ml/min) m/e 613.40 (M+H)$^+$, $t_R$ 1.55.min. $^1$H NMR (400 MHz, CHLOROFORM-D) δ ppm 0.92 (m, 7 H) 1.49 (dd, J=14.31, 6.72 Hz, 1 H) 1.65 (m, 1 H) 1.81 (m, 1 H) 1.90 (s, 3H) 2.03 (m, 2 H) 2.31 (m, 4 H) 2.63 (dd, J=13.57, 10.64 Hz, 1 H) 3.07 (m, 6 H) 3.46 (m, 1 H) 3.86 (m, 1H) 4.10 (s, 4 H) 4.85 (s, 4 H) 6.10 (s, 1 H) 7.18 (m, 10 H) 7.69 (d, J=8.80 Hz, 1 H).

EXAMPLE 36

(2S)-2-(3(S)-acetylamino-3-((S)-sec-butyl)-2-oxo-pyrrolidin-1-yl)-N-[(1S,2R)-1-benzyl-2-hydroxy-3-(3-fluoro,5-(trifluoromethyl)benzylamino)-propyl]-4-phenyl-butyramide

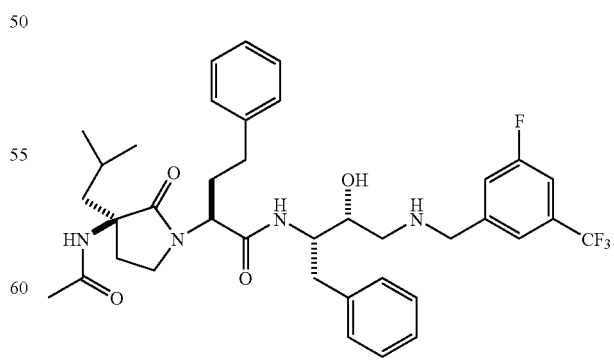

Following the general procedure for Example (3), but using the intermediate of Preparation (P) the title compound as a TFA salt was obtained as a white solid (6.0 mg) in 23% yield.

LC-MS (column=XTERRA C18 S7, 3×50 mm, start % B=0, final % B=100, gradient time=2 min, flow rate=5 ml/min) m/e 699.48 (M+H)+, $t_R$ 1.69 min.

EXAMPLE 37

2-(3(S)-Acetylamino-3(S)-isobutyl-2-oxo-pyrrolidin-1-yl)-N-[(1S,2R)-1-benzyl-3-(2-cyano-ethylamino)-2-hydroxy-propyl]-4-phenyl-butyramide

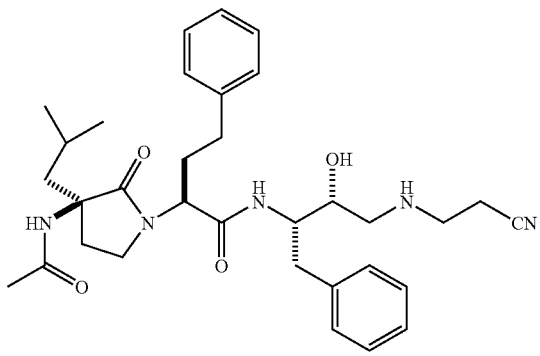

Following the general procedure for Example (3), but using the intermediate from Preparation (Q) the title compound as a TFA salt was obtained as a colorless residue (15.0 mg) in 65% yield. LC-MS (column=XTERRA C18 S7, 3×50 mm, start % B=0, final % B=100, gradient time=2 min, flow rate=5 ml/min) m/e 576.59 (M+H)+, $t_R$ 1.55.min. $^1$H NMR (400 MHz, CHLOROFORM-D) δ ppm 1.02 (dd, J=6.60, 1.71 Hz, 6H) 1.50 (dd, J=14.43, 6.85 Hz, 1 H) 1.69 (m, 1 H) 1.83 (m, J=12.84, 6.48 Hz, 1 H) 2.02 (s, 3 H) 2.14 (m, 1 H) 2.36 (m, 4 H) 3.14 (m, 10 H) 3.95 (m, 1 H) 4.13 (m, 1H) 5.67 (m, 4 H) 6.13 (s, 1 H) 7.17 (m, 10 H) 7.98 (d, J=8.80 Hz, 1 H).

EXAMPLE 38

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(2-methoxyphenyl)-butyramide

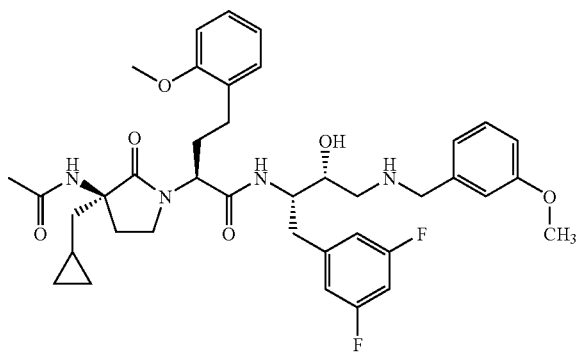

Step (38a) 2-tert-Butoxycarbonylamino-succinic acid 1-benzyl ester 4-(2,5-dioxo-pyrrolidin-1-yl) ester. A solution of BOC-Asp-OBzl (1.49 g, 4.61 mmol) and N-Hydroxy succinimide (584 mg, 5.07 mmol) in EtOAc (20 ml) was cooled to 0° C. 1,3-Dicyclohexylcarbodiimide (1.05 g, 5.07 mmol) was added portionwise. White precipitate began forming. The resulting mixture was stirred at 0° C. for 10 min. and then allowed to warm to rt. After stirring for 6 h. at rt the mixture was filtered and concentrated in vacuo to give 2-tert-butoxycarbonylamino-succinic acid 1-benzyl ester 4-(2,5-dioxo-pyrrolidin-1-yl) ester as a clear, colorless oil which was used without further purification.

Step (38b): 2-tert-Butoxycarbonylamino-4-hydroxy-butyric acid benzyl ester. A solution of NaBH$_4$ (262 mg, 6.92 mmol) in 4:1 THF:H$_2$O (20 ml) was cooled to 0° C. To this mixture was slowly added a solution of the ester from step (38a) (4.61 mmol) in THF (12 ml). Gas was evolved. When gas evolution ceased, the mixture was quenched by the careful addition of saturated aqueous ammonium chloride. The resulting solution was stirred at 0° C. for an additional 15 min. EtOAc (200 ml) was added and the resulting mixture was washed with saturated aqueous NaCl. The organic layer was dried over MgSO$_4$ and concentrated in vacuo. Purification by flash chromatography (silica, 0-10% MeOH/CHCl$_3$) gave 2-tert-butoxycarbonylamino-4-hydroxy-butyric acid benzyl ester (350 mg, 25% for 2 steps) as a clear, colorless oil: $^1$H NMR (300 MHz, Methanol-D) δ 7.23-7.43 (m, 5 H), 5.06-5.25 (m, 2 H), 4.00-4.57 (m, 2 H), 3.54-3.69 (m, 1 H), 1.67-2.12 (m, 2 H), 1.29-1.50 (m, 9 H). LC-MS (Method A, retention time: 1.25 min).

Step (38c): 2-tert-Butoxycarbonylamino-4-iodo-butyric acid benzyl ester. To a solution of triphenylphosphine (734 mg, 2.80 mmol) and imidazole (191 mg, 2.80 mmol) in CH$_2$Cl$_2$ (10 ml) at rt was added iodine (711 mg, 2.80 mmol) portionwise over 5 min. The mixture first turned yellow, then brown and developed precipitate. The mixture was stirred at rt until no pieces of iodine were visible (approx. 5 min.). A solution of alcohol from step (38b) (721 mg, 2.33 mmol) in CH$_2$Cl$_2$ (5 ml) was added and the resulting mixture was stirred at rt for 1 h. The reaction was filtered and concentrated in vacuo. Purification by flash chromatography (silica, 0-25% EtOAc/Hexane) gave 2-tert-butoxycarbonylamino-4-iodo-butyric acid benzyl ester (430 mg, 44%) as a slightly yellow oil: $^1$H NMR (500 MHz, Methanol-D) δ 7.24-7.42 (m, 5 H), 5.07-5.25 (m, 2 H), 4.16-4.31 (m, 1 H), 3.12-3.29 (m, 2 H), 2.01-2.35 (m, 2 H), 1.42 (s, 9 H). LC-MS (Method A, retention time: 1.71 min), MS m/z 420 (M$^+$+1).

Step (38d): General Procedure. 2-tert-Butoxycarbonylamino-4-phenyl-butyric acid benzyl esters. A suspension of 325 mesh Zinc dust (1.387 g, 28.62 mmol) in DMF (2.5 ml) was treated with 1,2-dibromoethane (123 μl, 1.43 mmol). The mixture was heated to 60° C. and stirred for 30 min. After cooling to rt, chlorotrimethylsilane (37 μl, 0.29 mmol) was added and the resulting mixture was stirred at rt for 30 min. A solution of iodide (38c) (2.0 g, 4.77 mmol) in DMF (2.5 ml) was then added and the mixture was heated to 35° C. After stirring for 1 h. at 35° C., at which time TLC indicated there was no starting iodide remaining, the mixture was allowed to cool to rt Pd$_2$(dba)$_3$ (87 mg, 0.095 mmol), tri-o-tolyl phosphine (116 mg, 0.38 mmol), and 2-methoxyiodobenzene (step (38d), or other aryl iodides) (4.77 mmol) were added and the mixture was stirred at rt for 16 h. The reaction was diluted with EtOAc and washed with saturated aqueous NaCl. The organic layer was dried over MgSO$_4$ and concentrated in vacuo. Purification by flash chromatography (silica, 0-25% EtOAc/Hexane) gave the desired 2-tert-Butoxycarbonylamino-4-(2-methoxyphenyl)-butyric acid benzyl ester (30-60%) or other desired similar esters. 2-tert-Butoxycarbonylamino-4-(2-methoxyphenyl)-butyric acid benzyl ester: $^1$H NMR (500 MHz, Methanol-D) δ 7.25-7.41 (m, 5 H), 7.15 (t, J=7.02 Hz, 1 H), 7.04 (d, J=7.32 Hz, 1 H), 6.89 (d, J=7.93 Hz, 1 H), 6.82 (t, J=7.32 Hz, 1 H), 5.02-5.20 (m, 2 H), 3.91-4.12

(m, 1 H), 3.78 (s, 3 H), 2.56-2.72 (m, 2 H), 1.79-2.14 (m, 2 H), 1.29-1.49 (m, 9 H). LC-MS (Method A, retention time: 1.82 min), MS m/z 400 (M$^+$+1).

Step (38e): 2-Amino-4-(2-methoxyphenyl)-butyric acid benzyl ester. A solution of ester from step (38d) (2.86 mmol) in CH$_2$Cl$_2$ (5 ml) was treated with trifluoroacetic acid (5 ml). The mixture was stirred at rt for 1 h. The reaction was then concentrated in vacuo. The residue was taken up in EtOAc. The resulting solution was washed with saturated aqueous NaHCO$_3$, saturated aqueous NaCl, dried over MgSO$_4$ and concentrated in vacuo. Purification by flash chromatography (silica, 0-20% MeOH/CHCl$_3$) gave the desired amine (quantitative). $^1$H NMR (500 MHz, Methanol-D) δ 7.29-7.43 (m, 5 H), 7.14-7.21 (m, 1 H), 7.04 (dd, J=7.32, 1.53 Hz, 1 H), 6.91 (d, J=8.24 Hz, 1H), 6.78-6.86 (m, 1 H), 5.20 (q, J=12.21 Hz, 2 H), 3.82 (t, J=6.26 Hz, 1 H), 2.56-2.79 (m, 2 H), 1.96-2.16 (m, 2H). LC-MS (Method A, retention time: 1.32 min), MS m/z 300 (M$^+$+1).

Step (38f): The acid from step (6e) (250 mg, 825 μmol, 1 eq) and the amine from step (38e) (296 mg, 990 μmol, 1.2 eq) were dissolved in CH$_2$Cl$_2$ (6.5 mL) and DMF (3.2 mL). PyBOP (515 mg, 990 μmol, 1.2 eq) was then added, followed by DIEA (575 μL, 3.30 mmol, 4 eq). The reaction was allowed to stir at room temperature overnight. Water was added, and the mixture extracted three times into CH$_2$Cl$_2$. The combined organic layers were dried over MgSO$_4$, filtered, and concentrated in vacuo. Chromatography (5% to 40% EtOAc/Hexane) yielded 336.6 mg of product (70% yield).

$^1$H NMR (500 MHz, CHLOROFORM-D) δ ppm 7.32 (m, 10 H), 7.17 (m, 1 H), 7.03 (dd, J=7.32, 1.53 Hz, 1 H), 6.83 (m, 2 H), 6.66 (d, J=7.63 Hz, 1 H), 5.92 (m, 1 H), 5.68 (m, 1 H), 5.07 (m, 6 H), 4.70 (m, 1 H), 3.76 (m, 3 H), 2.96 (m, 1 H), 2.65 (m, 1 H), 2.57 (m, 1 H), 2.48 (dd, J=14.50, 6.56 Hz, 1 H), 2.15 (m, 1 H), 2.04 (m, 2 H), 1.81 (dd, J=14.50, 5.95 Hz, 1 H), 0.59 (m, 1H), 0.37 (m, 2 H), 0.03 (m, 2 H). LC-MS (Method B, retention time: 2.820 min), MS m/z 585 (M$^+$+1).

Step (38g): The amide from step (38f) (333 mg, 570 mmol, 1 eq) was dissolved in ether (1.8 mL). A solution of sodium periodate (265 mg) in water (1.8 mL) was added, followed by a 2.5 wt % solution of osmium tetroxide in t-butanol (390 μL). The combined reagents were stirred rapidly at room temperature overnight. Ether was added, mixed with the reaction mixture and decanted (2 times). The combined organic layers were dried over MgSO$_4$, filtered, and concentrated in vacuo. The resulting residue was dissolved in CH$_2$Cl$_2$ and cooled to 0° C. Simultaneously, triethyl silane (2.6 mL) and TFA (2.6 mL) was added over approx. 90 seconds. The reaction was kept at 0° C. for 3 h. Solvents were removed in vacuo. Chromatography (5% to 40% EtOAc/Hexane) yielded 163.8 mg product (50% yield). $^1$H NMR (500 MHz, CHLOROFORM-D) δ ppm 7.31 (m, 10 H), 7.15 (m, 2 H), 6.83 (m, 2 H), 5.08 (m, 4 H), 4.87 (dd, J=11.14, 4.43 Hz, 1 H), 4.11 (m, 1 H), 3.76 (m, 3 H), 3.40 (m, 2 H), 2.71 (m, 1 H), 2.56 (m, 1 H), 2.44 (m, 2 H), 2.24 (m, 1 H), 1.92 (m, 1 H), 1.65 (m, 1 H), 1.54 (m, 1 H), 0.70 (m, 1 H), 0.38 (m, 2 H), −0.01 (m, 2 H). LC-MS (Method A, retention time: 1.973 min), MS m/z 571 (M$^+$+1).

Step (38h): The lactam from step (38g) (160 mg, 281 μmol) was dissolved in ethanol (25 mL). Ten percent Pd on carbon was added, and the reaction stirred under balloon pressure hydrogen for 4 h. The reaction was filtered over celite, and concentrated in vacuo. The residue was dissolved in pyridine, and acetic anhydride was added. After stirring at room temperature overnight, the solvents were removed in vacuo. Chromatography yielded pure lactam acid. $^1$H NMR (500 MHz, CD$_3$OD) δ ppm 7.17 (m, 2 H), 6.91 (d, J=7.93 Hz, 1 H), 6.83 (t, J=6.87 Hz, 1 H), 4.70 (dd, J=11.29, 4.27 Hz, 1 H), 3.83 (s, 3 H), 3.60 (m, 2 H), 2.88 (m, 1 H), 2.54 (m, 2 H), 2.39 (m, 1 H), 2.18 (m, 1 H), 2.05 (m, 1 H), 1.94 (s, 3 H), 1.75 (m, 1 H), 1.59 (dd, J=13.89, 7.17 Hz, 1 H), 0.85 (m, 1 H), 0.49 (m, 2 H), 0.18 (m, 1 H), 0.09 (m, 1 H). LC-MS (Method A, retention time: 1.823 min), MS m/z 389 (M$^+$+1).

Step (38i): The acid from step (38h) (22.1 mg, 57.0 μmol) and the amine of Preparation (B) (31.0 mg, 71.2 μmol, 1.25 eq) were dissolved in DMF (670 μL). PyBOP (36 mg) and DIEA (40 μL) were added, and the reaction stirred at room temperature overnight. The reaction was purified by reverse-phase chromatography, and concentrated in vacuo. The residue was stirred in 1:1 TFA/CH$_2$Cl$_2$ for 2 h, then concentrated in vacuo. The residue was trapped on SCX resin, then eluted with 2 M NH$_3$/MeOH to provide the title compound of Example (38) after concentration in vacuo. $^1$H NMR (500 MHz, CHLOROFORM-D) δ ppm 7.40 (d, J=9.16 Hz, 1 H), 7.16 (m, 2 H), 7.05 (m, 1 H), 6.86 (m, 3 H), 6.78 (m, 4 H), 6.52 (m, 1 H), 6.30 (s, 1 H), 4.10 (m, 1 H), 3.78 (m, 9 H), 3.62 (m, 1 H), 3.36 (m, 1 H), 3.21 (q, J=8.44 Hz, 1 H), 2.94 (m, 1 H), 2.71 (m, 3 H), 2.52 (m, 3 H), 2.36 (m, 1 H), 2.25 (m, 1 H), 2.01 (m, 5 H), 1.74 (dd, J=14.04, 5.49 Hz, 1 H), 1.48 (dd, J=14.19, 7.78 Hz, 1H), 1.27 (m, 1 H), 0.78 (dd, J=7.63, 5.19 Hz, 1 H), 0.58 (m, 2 H), 0.17 (m, 2 H). LC-MS (Method B, retention time: 2.263 min), MS m/z 707 (M$^+$+1).

EXAMPLE 39

(2S)-2-(3(S)-acetylamino-3-cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3,4-methylenedioxyphenyl)-butyramide

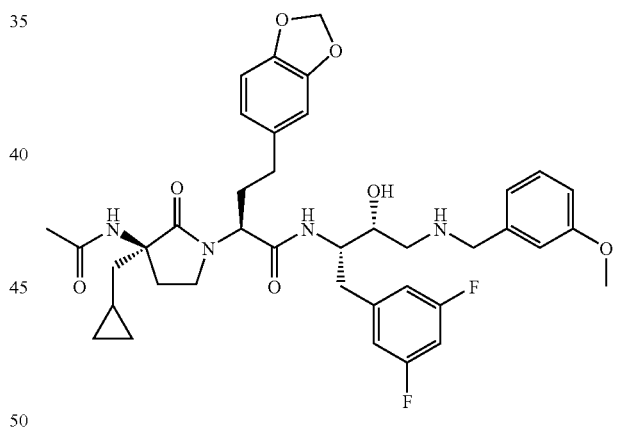

Step (39a): The iodide of step (38c) was reacted in the manner of step (38d) with 1-iodo-3,4-methylenedioxybenzene to provide the compound of step (39a). $^1$H NMR (500 MHz, Methanol-D) δ 7.25-7.40 (m, 5H), 6.53-6.74 (m, 3 H), 5.87 (s, 2 H), 5.04-5.24 (m, 2H), 4.09 (q, J=7.02 Hz, 1 H), 2.46-2.65 (m, 2 H), 1.79-2.09 (m, 2 H), 1.26-1.50 (m, 9 H). LC-MS (Method A, retention time: 1.83 min), MS m/z 414 (M$^+$+1).

Step (39b): Boc-amino acid (39a) was reacted in the manner of step (38e) to provide the amine of step (39b). $^1$H NMR (500 MHz, Methanol-D) δ 7.33-7.47 (m, 5H), 6.51-6.73 (m, 3 H), 5.84-5.91 (m, 2 H), 5.15-5.40 (m, 2 H), 4.05 (t, J=6.26 Hz, 1 H), 2.44-2.70 (m, 2H), 1.99-2.23 (m, 2 H). LC-MS (Method A, retention time: 1.26 min), MS m/z 314 (M$^+$+1).

Step (39c): The acid from step (6e) (200 mg, 660 μmol, 1 eq) and the amine of step (39b) (248 mg, 792 μmol, 1.2 eq)

were reacted in the manner of step (38f). $^1$H NMR (500 MHz, CHLOROFORM-D) δ ppm 7.32 (m, 10 H), 6.66 (m, 2 H), 6.56 (d, J=1.53 Hz, 1 H), 6.51 (d, J=7.93 Hz, 1 H), 5.89 (s, 2 H), 5.79 (m, 1 H), 5.67 (m, 1 H), 5.21 (m, 1 H), 5.09 (m, 5 H), 4.66 (m, 1 H), 2.91 (dd, J=14.34, 7.63 Hz, 1 H), 2.49 (m, 3 H), 2.10 (m, 1 H), 1.96 (m, 2 H), 1.82 (dd, J=14.34, 6.10 Hz, 1 H), 0.57 (m, 1 H), 0.38 (m, 2 H), 0.02 (m, 2 H) LC-MS (Method B, retention time: 2.777 min), MS m/z 599 (M$^+$+1).

Step (39d): The product from step (39c) was reacted in the manner of step (38g). $^1$H NMR (500 MHz, CHLOROFORM-D) δ ppm 7.31 (m, 10 H), 6.67 (m, 3 H), 5.89 (s, 2 H), 5.48 (s, 1 H), 5.09 (m, 4 H), 4.85 (dd, J=10.83, 4.43 Hz, 1 H), 3.35 (m, 2 H), 2.58 (m, 2 H), 2.40 (m, 2 H), 2.24 (m, 1 H), 2.02 (m, 1 H), 1.63 (m, 1 H), 1.52 (m, 1 H), 0.69 (m, 1 H), 0.38 (m, 2 H), −0.01 (m, 2H). LC-MS (Method A, retention time: 1.933 min), MS m/z 585 (M$^+$+1).

Step (39e): The product from step (39d) was reacted in the manner of step (38h) and taken on without further purification.

Step (39f): The product from step (39e) was reacted in the manner of step (38i) to produce the title compound of Example (39). $^1$H NMR (500 MHz, CHLOROFORM-D) δ ppm 7.46 (m, 1 H), 7.23 (m, 2 H), 6.66 (m, 10 H), 6.28 (s, 1 H), 5.90 (m, 2 H), 4.11 (m, 1 H), 3.78 (m, 5 H), 3.55 (m, 1 H), 3.31 (m, 1 H), 3.17 (m, 1 H), 2.98 (dd, J=14.19, 3.51 Hz, 1 H), 2.71 (m, 3 H), 2.35 (m, 5 H), 2.01 (m, 5 H), 1.70 (dd, J=14.19, 5.34 Hz, 1 H), 1.47 (dd, J=14.04, 7.93 Hz, 1 H), 0.76 (m, 1 H), 0.60 (m, 2 H), 0.19 (m, 2 H). LC-MS (Method B, retention time: 2.107 min), MS m/z 721 (M$^+$+1).

EXAMPLE 40

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-fluorophenyl)-butyramide

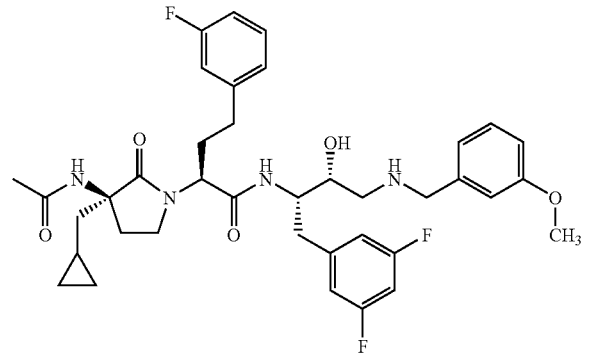

Step (40a): The iodide of step (38c) was reacted in the manner of step (38d) with 1-iodo-3-fluorobenzene to provide the compound of step (40a). $^1$H NMR (500 MHz, Methanol-D) δ 7.27-7.41 (m, 5 H), 6.83-7.28 (m, 4 H), 5.06-5.23 (m, 2 H), 4.11 (d, J=4.58 Hz, 1 H), 2.57-2.73 (m, 2 H), 1.84-2.13 (m, 2H), 1.27-1.49 (m, 9 H).

Step (40b): Boc-amino acid from step (40a) was reacted in the manner of step (38e) to provide the compound of step (40b). $^1$H NMR (500 MHz, Methanol-D) δ 7.34-7.48 (m, 5 H), 7.23-7.31 (m, 1 H), 6.89-6.98 (m, 2 H), 6.86 (d, J=10.07 Hz, 1 H), 5.21-5.38 (m, 2 H), 4.08 (t, J=6.10 Hz, 1 H), 2.54-2.79 (m, 2 H), 2.00-2.30 (m, 2 H). LC-MS (Method A, retention time: 1.30 min), MS m/z 288 (M$^+$+1).

Step (40c): The acid from step (6e) (250 mg, 825 μmol, 1 eq) and the amine from step (40b) (284 mg, 990 μmol, 1.2 eq) were reacted in the manner of step (38f). $^1$H NMR (500 MHz, CHLOROFORM-D) δ ppm 7.32 (m, 10 H), 7.19 (m, 1 H), 6.86 (m, 2 H), 6.74 (m, 2 H), 5.68 (m, 2 H), 5.20 (m, 1 H), 5.10 (m, 5 H), 4.67 (dd, J=12.51, 7.32 Hz, 1 H), 2.90 (dd, J=14.19, 7.78 Hz, 1H), 2.57 (m, 2 H), 2.49 (m, 1 H), 2.15 (m, 1 H), 1.97 (m, 2 H), 1.85 (dd, J=14.34, 6.10 Hz, 1 H), 0.58 (m, 1H), 0.39 (m, 2 H), 0.03 (m, 2 H). LC-MS (Method A, retention time: 1.967 min), MS m/z 573 (M$^+$+1).

Step (40d): The product from step (40c) was reacted in the manner of step (38g). $^1$H NMR (500 MHz, CHLOROFORM-D) δ ppm 7.32 (m, 10 H), 7.20 (m, 1 H), 6.96 (m, 2 H), 6.86 (m, 1 H), 5.46 (s, 1 H), 5.09 (m, 4 H), 4.87 (dd, J=10.99, 4.58 Hz, 1 H), 3.36 (m, 2 H), 2.67 (m, 2 H), 2.38 (m, 2 H), 2.31 (m, 1 H), 2.03 (m, 1 H), 1.63 (m, 1 H), 1.51 (dd, J=14.34, 7.02 Hz, 1 H), 0.69 (m, 1 H), 0.39 (m, 2 H), 0.00 (m, 2 H). LC-MS (Method A, retention time: 1.953 min), MS m/z 559 (M$^+$+1).

Step (40e): The product from step (40d) was reacted in the manner of step (38h). LC-MS (Method A, retention time: 1.283 min), MS m/z 377 (M$^+$+1).

Step (40f): The product from step (40e) was reacted in the manner of step (38i) to provide the title compound of Example (40). $^1$H NMR (500 MHz, CHLOROFORM-D) δ ppm 7.41 (d, J=9.16 Hz, 1 H), 7.20 (m, 2 H), 6.82 (m, 8 H), 6.53 (m, 1 H), 6.29 (s, 1 H), 4.13 (m, 1 H), 3.79 (m, 6 H), 3.56 (m, 1 H), 3.33 (m, 1 H), 3.16 (m, 1 H), 2.96 (dd, J=14.34, 3.66 Hz, 1 H), 2.69 (m, 3 H), 2.46 (m, 4 H), 2.23 (m, 1 H), 2.12 (m, 1 H), 2.01 (m, 3 H), 1.70 (dd, J=14.04, 5.49 Hz, 1 H), 1.47 (dd, J=14.04, 7.93 Hz, 1 H), 0.76 (m, 1 H), 0.60 (m, 2 H), 0.19 (m, 2 H). LC-MS (Method B, retention time: 2.160 min), MS m/z 695 (M$^+$+1).

EXAMPLE 41

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(4-fluorophenyl)-butyramide

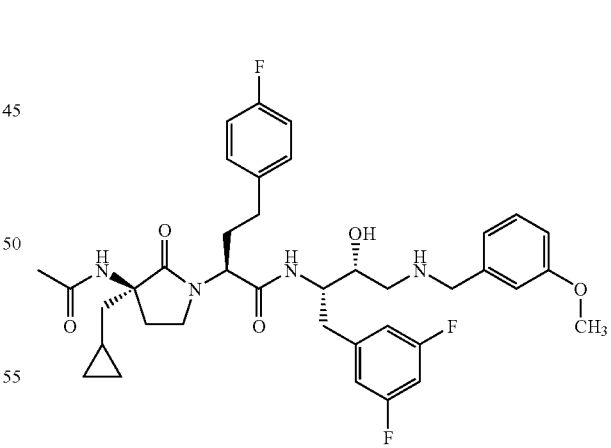

Step (41a): The iodide of step (38c) was reacted in the manner of step (38d) with 1-iodo-4-fluorobenzene to provide the compound of step (41a). $^1$H NMR (500 MHz, Methanol-D) δ 7.26-7.44 (m, 5 H), 6.68-7.20 (m, 4 H), 5.03-5.24 (m, 2 H), 3.92-4.15 (m, 1 H), 2.50-2.75 (m, 2 H), 1.82-2.11 (m, 2 H), 1.30-1.52 (m, 9 H).

Step (41b): Boc-amino acid from step (41a) was reacted in the manner of step (38e) to provide the compound of step (41b). $^1$H NMR (500 MHz, Methanol-D) δ 7.33-7.47 (m, 5 H), 7.08-7.16 (m, 2 H), 6.93-7.04 (m, 2 H), 5.20-5.38 (m, 2 H), 4.07 (t, J=6.26 Hz, 1 H), 2.50-2.79 (m, 2 H), 2.05-2.23 (m, 2 H). LC-MS (Method A, retention time: 1.32 min), MS m/z 288 (M$^+$+1).

Step (41c): The acid from step (6e) (250 mg, 825 μmol, 1 eq) and the amine from step (41b) (284 mg, 990 μmol, 1.2 eq) were reacted in the manner of step (38f). $^1$H NMR (500 MHz, CHLOROFORM-D) δ ppm 7.33 (m, 12 H), 7.01 (m, 2 H), 6.92 (m, 2 H), 6.69 (d, J=7.63 Hz, 1 H), 5.69 (m, 2 H), 5.18 (m, 6 H), 4.66 (m, 1 H), 2.90 (m, 1 H), 2.52 (m, 3 H), 2.12 (m, 1 H), 1.96 (m, 2 H), 1.85 (m, 1 H), 0.57 (m, 1 H), 0.39 (m, 2 H), 0.03 (m, 2 H). LC-MS (Method B, retention time: 2.840 min), MS m/z 573 (M$^+$+1).

Step (41d): The product from step (41c) was reacted in the manner of step (38g). $^1$H NMR (500 MHz, CHLOROFORM-D) δ ppm 7.30 (m, 10 H), 7.15 (m, 2 H), 6.93 (m, 2 H), 5.46 (s, 1 H), 5.09 (m, 4 H), 4.85 (dd, J=10.99, 4.27 Hz, 1 H), 3.36 (s, 2 H), 2.63 (m, 2 H), 2.39 (m, 2 H), 2.27 (m, 1 H), 2.08 (m, 1 H), 1.62 (dd, J=14.04, 6.41 Hz, 1 H), 1.50 (m, 1 H), 0.70 (m, 1 H), 0.39 (m, 2 H), 0.02 (m, 2 H). LC-MS (Method A, retention time: 1.947 min), MS m/z 559 (M$^+$+1).

Step (41e): The product from step (41d) was reacted in the manner of step (38h). LC-MS (Method A, retention time: 1.280 min), MS m/z 377 (M$^+$+1).

Step (41f): The product from step (41e) was reacted in the manner of step (38i) to provide the title compound of Example (41). $^1$H NMR (500 MHz, CHLOROFORM-D) δ ppm 7.41 (d, J=9.16 Hz, 1 H), 7.21 (m, 2 H), 7.06 (m, 2 H), 6.92 (m, 4 H), 6.77 (m, 3 H), 6.52 (m, 1 H), 4.12 (m, 1 H), 3.79 (m, 5 H), 3.56 (m, 1 H), 3.33 (m, 1 H), 3.16 (m, 1 H), 2.96 (dd, J=14.19, 3.81 Hz, 1 H), 2.70 (m, 3 H), 2.44 (m, 4 H), 2.22 (m, 1 H), 2.09 (m, 1 H), 2.00 (m, 3 H), 1.69 (dd, J=14.04, 5.49 Hz, 1 H), 1.47 (dd, J=14.04, 7.93 Hz, 1 H), 0.76 (m, 1 H), 0.59 (m, 2 H), 0.19 (m, 2 H). LC-MS (Method B, retention time: 2.153 min), MS m/z 695 (M$^+$+1).

EXAMPLE 42

(2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-methoxyphenyl)-butyramide

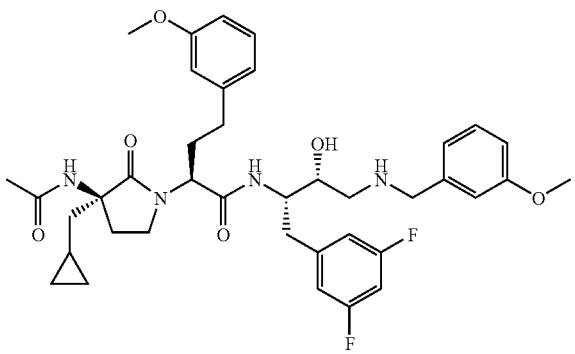

Step (42a): The iodide of step (38c) was reacted in the manner of step (38d) with 1-iodo-3-methoxybenzene to provide the compound of step (42a). $^1$H NMR (300 MHz, Methanol-D) δ 7.24-7.42 (m, 5 H), 6.98-7.12 (m, 2 H), 6.80 (d, J=8.42 Hz, 2 H), 5.01-5.25 (m, 2 H), 3.99-4.21 (m, 1 H), 3.74 (s, 3 H), 2.45-2.69 (m, 2 H), 1.76-2.13 (m, 2 H), 1.27-1.52 (m, 9 H). LC-MS (Method A, retention time: 1.83 min), MS m/z 400 (M$^+$+1).

Step (42b): The boc-amino acid from step (42a) was reacted in the manner of step (38e) to provide the compound of step (42b). $^1$H NMR (300 MHz, Methanol-D) δ 7.24-7.43 (m, 5 H), 7.02 (d, J=8.42 Hz, 2 H), 6.72-6.84 (m, 2 H), 5.06-5.24 (m, 2 H), 3.73 (s, 3 H), 3.46 (t, J=6.40 Hz, 1 H), 2.40-2.70 (m, 2 H), 1.72-2.08 (m, 2 H). LC-MS (Method A, retention time: 1.28 min), MS m/z 300 (M$^+$+1).

Step (42c): The acid from step (6e) (269.5 mg, 889 μmol, 1 eq) and the amine from step (42b) (319.1 mg, 1.067 mmol, 1.2 eq) were reacted in the manner of step (38f).

$^1$H NMR (500 MHz, CHLOROFORM-D) δ ppm 7.32 (m, 12 H), 7.16 (t, J=7.93 Hz, 1 H), 6.68 (m, 4 H), 5.80 (s, 1H), 5.66 (m, 1 H), 5.19 (m, 1 H), 5.08 (m, 5 H), 4.69 (m, 1 H), 3.75 (s, 3 H), 2.90 (m, 2 H), 2.52 (m, 2 H), 2.15 (m, 1 H), 2.00 (m, 1 H), 1.79 (dd, J=14.50, 5.95 Hz, 1 H), 0.56 (m, 1 H), 0.38 (m, 2 H), 0.02 (m, 2 H). LC-MS (Method B, retention time: 2.790 min), MS m/z 585 (M$^+$+1).

Step (42d): The product from step (42c) was reacted in the manner of step (38g) and taken on without further purification.

Step (42e): The product from step (42d) was reacted in the manner of step (38h) and taken on without further purification.

Step (42f): The product from step (42e) was reacted in the manner of step (38i). $^1$H NMR (500 MHz, CHLOROFORM-D) δ ppm 7.42 (d, J=9.16 Hz, 1 H), 7.17 (m, 3 H), 6.69 (m, 11 H), 6.29 (s, 1 H), 3.79 (m, 8 H), 3.57 (dd, J=9.61, 5.34 Hz, 1 H), 3.31 (m, 1 H), 3.16 (q, J=8.55 Hz, 1 H), 2.96 (dd, J=14.19, 3.51 Hz, 1 H), 2.70 (m, 2 H), 2.47 (m, 4 H), 2.18 (m, 2 H), 2.03 (s, 3 H), 1.70 (dd, J=14.04, 5.49 Hz, 2 H), 1.47 (dd, J=14.04, 7.93 Hz, 2 H), 0.77 (m, 1 H), 0.60 (m, 2 H), 0.19 (m, 2 H). LC-MS (Method B, retention time: 2.167 min), MS m/z 707 (M$^+$+1).

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art.

The enzyme thus obtained can be put in contact with a test compound and with an appropriate substrate on which enzyme-mediated peptide bond hydrolysis is known to occur. The ability of the test compound to diminish the rate of substrate hydrolysis can then be quantified as a measure of inhibition potency. Appropriate substrates can be prepared as peptides, proteins, or chemically modified versions of peptides or proteins, that contain an amino acid sequence that is recognized as a substrate by the enzyme. For example, the amino acid sequence immediately proximal to the beta-cleavage site within Swedish mutant APP is known to be recognized as a substrate for BACE. It has been demonstrated that the amino acid sequence X-EVNLDAEFK(Y), (SEQ. ID. NO.:1), in which X is a chemical group appended to the N-terminus of the peptide and Y is a chemical group appended to the epsilon amino group of the C-terminal lysine side chain, is efficiently cleaved by BACE at the peptide bond between the L and D residues. Longer peptide and protein substrates can also be designed by extending the amino acid composition on the N-terminal, the C-terminal, or both ends.

In one known application of (SEQ. ID. NO.:1), X is a 7-methoxycoumarin-4-acetyl (MCA) group and Y is a dinitrophenyl (DNP) group [Marcinkeviciene, J. et al., (2001) "Mechanism of inhibition of beta-site amyloid precursor protein-cleaving enzyme (BACE) by a statine-based peptide." *J. Biol. Chem.* 276: 23790-23794]. When this peptide is intact, the natural fluorescence of the MCA group is quenched by its proximity to the DNP group. Upon enzyme-mediated hydrolysis, the MCA and DNP groups are separated onto different peptide fragments and the fluorescence of the MCA group is thus revealed. The increase in fluorescence intensity that accompanies enzyme-mediated peptide hydrolysis can be measured as a function of time to quantify the velocity of enzyme catalysis. In a typical assay system the BACE enzyme is diluted into a buffer system composed of 50 mM acetate, pH 4.5 containing 0.25 mg/ml bovine serum albumin. To this is added neat dimethyl sulfoxide (DMSO) or a stock solution of test compound dissolved in DMSO so that the final amount of DMSO in all assays is held constant at 2.5% (v:v). The enzymatic reaction is then initiated by addition of a stock solution of the substrate peptide to a known concentration. The fluorescence increase with time after substrate addition is monitored with an appropriate fluorescence detection instrument, such as a microplate reader or spectrofluorometer. The slope of the signal vs. time plot (progress curve) for samples to which only DMSO was added is taken as a measure of the uninhibited velocity and represents 100% enzymatic activity. The diminution of velocity that is observed at a known concentration of test compound is used to define the % inhibition of activity as follows: % inhibition=100*(1−(vi/v0) where vi is the velocity in the presence of test compound at a known concentration and v0 is the velocity of the uninhibited enzyme. A compound is considered active in this assay if its $IC_{50}$ is less than 50 µM. Activity of example compounds of the invention is provided in Table 1, wherein +++ denotes activity of 0.1 µM or greater potency, ++ denotes potency in the range of 0.1 to 1.0 µM and + denotes potency in the range between 1 µM and 50 µM.

TABLE 1

| Compounds of Example | Activity Rating[a] |
|---|---|
| 1 | +++ |
| 2 | +++ |
| 3 | +++ |
| 4 | ++ |
| 5 | + |
| 6 | + |
| 7 | +++ |
| 8 | +++ |
| 9 | +++ |
| 10 | +++ |
| 11 | ++ |
| 12 | ++ |
| 13 | + |
| 14 | +++ |
| 15 | + |
| 16 | +++ |
| 17 | ++ |
| 18 | +++ |
| 19 | ++ |
| 20 | ++ |
| 21 | ++ |
| 22 | ++ |
| 23 | + |
| 24 | +++ |
| 25 | +++ |
| 26 | + |
| 27 | + |
| 28 | +++ |
| 29 | +++ |
| 30 | +++ |
| 31 | ++ |
| 32 | ++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |

[a]Activity based on $IC_{50}$ values:
+++ = <0.1 µM
++ = 0.1-1.0 µM
+ = 1.0-50 µM In an alternative application using the amino acid sequence X-EVNLDAEFK(Y)(SEQ ID NO:1), X is an acetyl group and Y is DNP. This peptide is put in contact with BACE and the test compound in a fashion similar to that described above. After a fixed period of time the enzymatic reaction is stopped by denaturing the enzyme by addition of a known amount of trifluoroacetic acid (TFA) or by heating the sample in a boiling water bath for 5 min. The sample is then loaded onto a C18 or other appropriate reverse phase HPLC column and the substrate peptide is separated from the product peptide fragments by isocratic or gradient elution methods well known to those trained in the art. The substrate and the C-terminal product peptide fragment can be identified by the absorbance at ca. 350 nm imparted by the DNP group. The area under the C-terminal product peak can be quantified as a measure of enzyme activity and the diminution of this activity can be used to define the inhibition potency of test compounds as described above. A compound is considered active in this assay if its $IC_{50}$ is less than 50 µM.

In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R.

PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature,* 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3 ® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 µg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 µM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present invention are considered active when tested in the above assay if the $IC_{50}$ value for the test compound is less than 50 µM. A preferred $IC_{50}$ value is less than 1 µM. A more preferred $IC_{50}$ value is less than 0.1 µM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), *J. Neurochem.* 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at –80° C. until analysis. For Aβ detection, plasma is diluted 15-fold in PBS with 0.1% Chaps while CSF is diluted 15-fold in 1% Chaps with protease inhibitors (5 µg/ml leupeptin, 30 µg/ml aprotinin, 1 mM phenylmethylsulfonylfluoride, 1 µM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. AD levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

All references cited herein are hereby incorporated in their entirety herein by reference.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents, or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I)

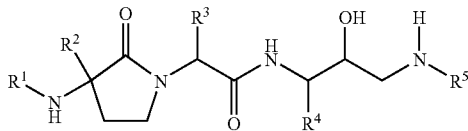

or a stereoisomer; or a pharmaceutically acceptable salt thereof, wherein $R^1$ is selected from the group consisting of —C(=O)$R^{1a}$, —S(=O)$R^{1a}$, —S(=O)$_2R^{1a}$, —C(=O)O$R^{1a}$, —C(=O)NH$R^{1a}$, and $C_1$-$C_6$ alkyl optionally substituted with $R^{1b}$;

$R^{1a}$ is $C_1$-$C_6$ alkyl optionally substituted with $R^{1b}$;

$R^{1b}$ is independently selected from the group consisting of halogen, —CF$_3$, —OCF$_3$, —CO$_2R^6$, —C(=O)NR$^6R^6$, —NR$^6$C(=O)R$^6$, —NR$^6R^6$, —NR$^6$SO$_2R^6$, —C(=O)R$^6$, —S(=O)R$^6$, —SO$_2R^6$, —SO$_2$NR$^6R^6$, —SR$^6$, —S(C$_1$-C$_4$ haloalkyl), —OR$^6$, —O(C$_1$-C$_4$ haloalkyl), —(C$_3$-C$_7$)cycloalkyl, -imidazole, -thiazole, -oxazole, —(C$_2$-C$_6$)alkenyl, and —(C$_2$-C$_6$)alkynyl;

$R^2$ is selected from the group consisting of $C_1$-$C_4$ alkyl, $C_2$-$C_4$ alkenyl, $C_2$-$C_4$ alkynyl, and $C_3$-$C_6$ cycloalkyl in which each group is optionally substituted with halogen, —CF$_3$, —OCF$_3$, —CH$_3$, —CH$_2$CH$_3$, —OCH$_3$, —OCH$_2$CH$_3$, or —(C$_3$-C$_7$)cycloalkyl;

$R^3$ is selected from the group consisting of $C_1$-$C_4$ alkyl, $C_2$-$C_4$ alkenyl, and $C_2$-$C_4$ alkynyl optionally substituted with $R^{3a}$, or phenyl optionally substituted with $R^{3b}$;

$R^{3a}$ is selected from the group consisting of $R^{3b}$, $C_3$-$C_6$ cycloalkyl optionally substituted with $R^{3b}$, phenyl optionally substituted with $R^{3b}$, and 3,4-methylenedioxyphenyl;

$R^{3b}$ is independently selected at each occurrence from the group consisting of halogen, —NO$_2$, —CN, —C$_1$-C$_4$alkyl, —OH, —OCH$_3$, —OCH$_2$CH$_3$, —CF$_3$, —OCF$_3$, —SCF$_3$, —C(=O)R$^6$, —NR$^6$C(=O)R$^6$, —NR$^6$SO$_2R^6$, —NR$^6R^6$, —OC(=O)NR$^6R^6$, —NR$^6$C(=O)NR$^6R^6$, —C(=O)NR$^6R^6$, —C(=O)OR$^6$, —SR$^6$, —S(=O)R$^6$, —S(=O)$_2R^6$, and —S(=O)$_2$NR$^6R^6$;

$R^4$ is selected from the group consisting of $C_1$-$C_4$ alkyl, $C_2$-$C_4$ alkenyl, and $C_2$-$C_4$ alkynyl optionally substituted with $R^{4a}$;

$R^{4a}$ is selected from $R^{4b}$, or phenyl optionally substituted with $R^{4b}$;

$R^{4b}$ is selected from the group consisting of halogen, —NO$_2$, —CN, —NCS, —CH$_3$, —CH$_2$CH$_3$, —CH$_2$CH$_2$CH$_3$, —CH(CH$_3$)$_2$, —CF$_3$, —OCF$_3$, —SCF$_3$, —OH, —OCH$_3$, —OCH$_2$CH$_3$, —SH, —SCH$_3$, —SCH$_2$CH$_3$, —CO$_2$H, —CO$_2$CH$_3$, —CO$_2$CH$_2$CH$_3$, —NH$_2$, —NH(CH$_3$), —N(CH$_3$)$_2$, —C(=O)NH$_2$, —C(=O)NH(CH$_3$), —C(=O)N(CH$_3$)$_2$, —C(=O)H, —C(=O)CH$_3$, —NHC(=O)CH$_3$, and —NHSO$_2$CH$_3$;

$R^5$ is $C_1$-$C_{10}$ alkyl optionally substituted with $R^{5a}$;

$R^{5a}$ is selected from the group consisting of $R^{5b}$, $C_3$-$C_8$ cycloalkyl, $C_2$-$C_6$ alkenyl, $C_2$-$C_6$ alkynyl, and phenyl optionally substituted with $R^{5b}$;

$R^{5b}$ is selected from the group consisting of $R^6$, halogen, —CN, —CF$_3$, —NO$_2$, —NCS, —OCF$_3$, —CO$_2$H, —C(=O)H, —OR$^6$, —NR$^6R^6$, —OC(=O)NR$^6R^6$, —NR$^6$C(=O)NR$^6R^6$, —C(=O)NR$^6R^6$, —C(=O)OR$^6$, —SR$^6$, —S(=O)R$^6$, —S(=O)$_2R^6$, and —S(=O)$_2$NR$^6R^6$; and $R^6$ is independently selected at each occurrence from the group consisting of hydrogen, $C_1$-$C_6$ alkyl and phenyl.

2. The compound of claim 1 having the Formula (I)

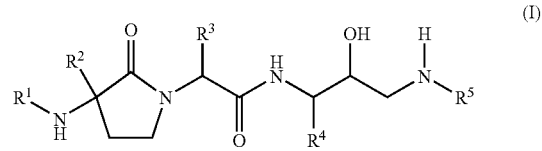

or a stereoisomer; or a pharmaceutically acceptable salt thereof, wherein $R^1$ is selected from the group consisting of —C(=O)$R^{1a}$, —S(=O)$R^{1a}$, —S(=O)$_2R^{1a}$, —C(=O)O$R^{1a}$, and —C(=O)NH$R^{1a}$;

$R^{1a}$ is $C_1$-$C_6$ alkyl optionally substituted with $R^{1b}$;

$R^{1b}$ is independently selected from the group consisting of halogen, —CF$_3$, —OCF$_3$, —CO$_2R^6$, —C(=O)NR$^6R^6$, —NR$^6$C(=O)R$^6$, —NR$^6R^6$, —OR$^6$, —(C3-C7)cycloalkyl, -imidazole, -thiazole, -oxazole, —(C$_2$-C$_6$)alkenyl, and —(C$_2$-C$_6$)alkynyl;

$R^2$ is selected from the group consisting of $C_1$-$C_4$ alkyl, $C_2$-$C_4$ alkenyl, $C_2$-$C_4$ alkynyl, and $C_3$-$C_6$ cycloalkyl in which each group is optionally substituted with halogen, —CF$_3$, —OCF$_3$, —CH$_3$, —CH$_2$CH$_3$, —OCH$_3$, —OCH$_2$CH$_3$, or $C_3$-$C_7$ cycloalkyl;

$R^3$ is $C_1$-$C_4$ alkyl optionally substituted with $R^{3a}$;

$R^{3a}$ is selected from the group consisting of $R^{3b}$, $C_3$-$C_6$ cycloalkyl optionally substituted with $R^{3b}$, phenyl optionally substituted with $R^{3b}$, and 3,4-methylenedioxyphenyl;

$R^{3b}$ is independently selected at each occurrence from the group consisting of halogen, $-NO_2$, $-CN$, $-C_1$-$C_4$alkyl, $-OH$, $-OCH_3$, $-OCH_2CH_3$, $-CF_3$, $-OCF_3$, $-SCF_3$, $-C(=O)R^6$, $-NR^6C(=O)R^6$, $-NR^6SO_2R^6$, $-NR^6R^6$, $-OC(=O)NR^6R^6$, $-NR^6C(=O)NR^6R^6$, $-C(=O)NR^6R^6$, $-C(=O)OR^6$, $-SR^6$, $-S(=O)R^6$, $-S(=O)_2R^6$, and $-S(=O)_2NR^6R^6$;

$R^4$ is $C_1$-$C_4$ alkyl optionally substituted with $R^{4a}$;

$R^{4a}$ is $R^{4b}$ or phenyl optionally substituted with $R^{4b}$;

$R^{4b}$ is selected from the group consisting of halogen, $-NO_2$, $-CN$, $-NCS$, $-CH_3$, $-CH_2CH_3$, $-CH_2CH_2CH_3$, $-CH(CH_3)_2$, $-CF_3$, $-OCF_3$, $-SCF_3$, $-OH$, $-OCH_3$, $-OCH_2CH_3$, $-SH$, $-SCH_3$, $-SCH_2CH_3$, $-CO_2H$, $-CO_2CH_3$, $-CO_2CH_2CH_3$, $-NH_2$, $-NH(CH_3)$, $-N(CH_3)_2$, $-C(=O)NH_2$, $-C(=O)NH(CH_3)$, $-C(=O)N(CH_3)_2$, $-C(=O)H$, $-C(=O)CH_3$, $-NHC(=O)CH_3$, and $-NHSO_2CH_3$;

$R^5$ is $C_1$-$C_{10}$ alkyl optionally substituted with $R^{5a}$;

$R^{5a}$ is selected from the group consisting of $R^{5b}$, $C_3$-$C_8$ cycloalkyl, $C_2$-$C_6$ alkenyl, $C_2$-$C_6$ alkynyl optionally substituted with $R^{5b}$, and phenyl optionally substituted with $R^{5b}$;

$R^{5b}$ is selected from the group consisting of $R^6$, halogen, $-CN$, $-CF_3$, $-NO_2$, $-NCS$, $-OCF_3$, $-CO_2H$, $-C(=O)H$, $-OR^6$, $-NR^6R^6$, $-OC(=O)NR^6R^6$, $-NR^6C(=O)NR^6R^6$, $-C(=O)NR^6R^6$, $-C(=O)OR^6$, $-SR^6$, $-S(=O)R^6$, $-S(=O)_2R^6$, and $-S(=O)_2NR^6R^6$; and $R^6$ is independently selected at each occurrence from the group consisting of hydrogen, $C_1$-$C_6$ alkyl and phenyl.

3. The compound of claim 2 having the Formula (I)

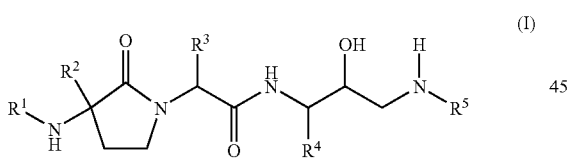

(I)

or a stereoisomer; or a pharmaceutically acceptable salt thereof, wherein $R^1$ is selected from the group consisting of $-C(=O)R^{1a}$, $-S(=O)R^{1a}$, $-S(=O)_2R^{1a}$, $-C(=O)OR^{1a}$, and $-C(=O)NHR^{1a}$;

$R^{1a}$ is $C_1$-$C_6$ alkyl optionally substituted with $R^{1b}$;

$R^{1b}$ is independently selected from the group consisting of halogen, $-CF_3$, $-OCF_3$, $-CO_2R^6$, $-C(=O)NR^6R^6$, $-NR^6C(=O)R^6$, $-NR^6R^6$, $-OR^6$, $-(C3-C7)$cycloalkyl, -imidazole, -thiazole, -oxazole, $-(C_2-C_6)$alkenyl, and $-(C_2-C_6)$alkynyl;

$R^2$ is selected from the group consisting of $C_1$-$C_4$ alkyl, $C_2$-$C_4$ alkenyl, $C_2$-$C_4$ alkynyl, and $C_3$-$C_6$ cycloalkyl in which each group is optionally substituted with halogen, $-CF_3$, $-OCF_3$, $-CH_3$, $-CH_2CH_3$, $-OCH_3$, $-OCH_2CH_3$, and $C_3$-$C_7$ cycloalkyl;

$R^3$ is $C_1$-$C_4$ alkyl optionally substituted with $R^{3a}$;

$R^{3a}$ is selected from the group consisting of $R^{3b}$, $C_3$-$C_6$ cycloalkyl optionally substituted with $R^{3b}$, phenyl optionally substituted with $R^{3b}$, and 3,4-methylenedioxyphenyl;

$R^{3b}$ is independently selected at each occurrence from the group consisting of halogen, $-NO_2$, $-CN$, $-(C_1-C_4)$ alkyl, $-CF_3$, $-OH$, $-OCH_3$, $-OCH_2CH_3$, $OCF_3$, $-SCF_3$, $-C(=O)R^6$, $-NR^6C(=O)R^6$, $-NR^6SO_2R^6$, $-NR^6R^6$, $-OC(=O)NR^6R^6$, $-NR^6C(=O)NR^6R^6$, $-C(=O)NR^6R^6$, $-C(=O)OR^6$, $-SR^6$, $-S(=O)R^6$, $-S(=O)_2R^6$, and $-S(=O)_2NR^6R^6$;

$R^4$ is $C_1$-$C_4$ alkyl substituted with $R^{4a}$;

$R^{4a}$ is selected from the group consisting of

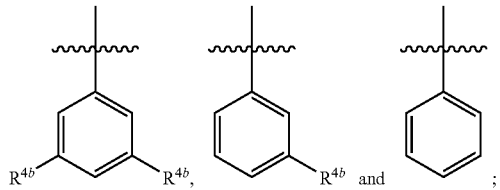

$R^{4b}$ is selected from the group consisting of F, Cl, Br, $-CH_3$, $-CH_2CH_3$, $-CF_3$, $-OCF_3$, $-SCF_3$, $-OH$, $-OCH_3$, $-SH$, $-SCH_3$, $-CO_2H$, $-CO_2CH_3$, $-NH_2$, $-NH(CH_3)$, $-N(CH_3)_2$, $-C(=O)NH_2$, $-C(=O)CH_3$, and $-NHC(=O)CH_3$;

$R^5$ is $C_1$-$C_{10}$ alkyl optionally substituted with $R^{5a}$;

$R^{5a}$ is selected from the group consisting of $R^{5b}$, $C_3$-$C_8$ cycloalkyl optionally substituted with $R^{5b}$, $C_2$-$C_6$ alkynyl optionally substituted with $R^{5b}$, and phenyl optionally substituted with $R^{5b}$;

$R^{5b}$ is selected from the group consisting of $R^6$, halogen, $-CN$, $-CF_3$, $-NO_2$, $-OCF_3$, $-CO_2H$, $-C(=O)H$, $-OR^6$, $-NR^6R^6$, $-OC(=O)NR^6R^6$, $-NR^6C(=O)NR^6R^6$, $-C(=O)NR^6R^6$, $-C(=O)OR^6$, $-SR^6$, $-S(=O)R^6$, $-S(=O)_2R^6$, and $-S(=O)_2NR^6R^6$; and $R^6$ is independently selected at each occurrence from the group consisting of hydrogen, $C_1$-$C_6$ alkyl and phenyl.

4. The compound of claim 3 having the Formula (I)

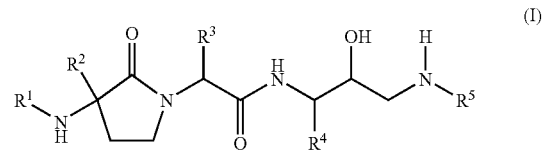

(I)

or a stereoisomer; or a pharmaceutically acceptable salt thereof, wherein $R^1$ is selected from the group consisting of $-C(=O)R^{1a}$, $S(=O)R^{1a}$, $-S(=O)_2R^{1a}$, $-C(=O)OR^{1a}$, and $-C(=O)NHR^{1a}$;

$R^{1a}$ is $C_1$-$C_6$ alkyl optionally substituted with $R^{1b}$;

$R^{1b}$ is independently selected from the group consisting of halogen, —CF3, —OCF3, —NR6R6, —OR6, —(C3-C7)cycloalkyl, -imidazole, thiazole, and oxazole;

$R^2$ is selected from the group consisting of $C_1$-$C_4$ alkyl optionally substituted with halogen, $-CF_3$, $-OCH_3$, $-OCH_2CH_3$, or $C_3$-$C_7$ cycloalkyl;

$R^3$ is $C_1$-$C_4$ alkyl optionally substituted with $R^{3a}$;

$R^{3a}$ is selected from the group consisting of phenyl optionally substituted with $R^{3b}$, and 3,4-methylenedioxyphenyl;

$R^{3b}$ is independently selected at each occurrence from the group consisting of F, Cl, $R^6$, —$CF_3$, OH, —$OCH_3$, —$OCH_2CH_3$, and —$NR^6R^6$;

$R^4$ is $C_1$-$C_4$ alkyl substituted with $R^{4a}$;

$R^{4a}$ is selected from the group consisting of

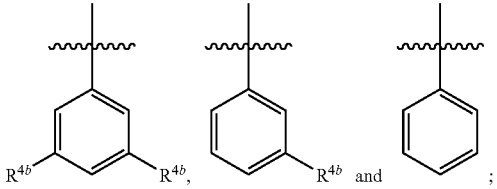

$R^{4b}$ is selected from the group consisting of F, Cl, Br, —$CH_3$, —$CF_3$, —OH, —$OCH_3$, —$NH_2$, —$NH(CH_3)$, and —$N(CH_3)_2$;

$R^5$ is $C_1$-$C_2$ alkyl optionally substituted with $R^{5a}$;

$R^{5a}$ is selected from the group consisting of $R^{5b}$, $C_3$-$C_4$ cycloalkyl optionally substituted with $R^{5b}$, alkynyl, and phenyl optionally substituted with $R^{5b}$;

$R^{5b}$ is selected from the group consisting of $R^6$, Cl, —CN, —$OR^6$, and —$NR^6R^6$; and $R^6$ is independently selected at each occurrence from the group consisting of hydrogen, $C_1$-$C_6$ alkyl and phenyl.

5. The stereoisomer compound of claim 4 having the Formula (Ia)

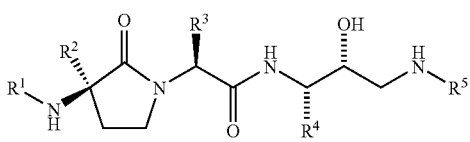

or a pharmaceutically acceptable salt thereof.

6. The compound of claim 1 of selected from the group consisting of
- (2S)-2-(3(S)-Acetylamino-3-((S)-sec-butyl)-2-oxo-pyrrolidin-1-yl)-N-[(1S,2R)-1-(3,5-difluoro-benzyl)-2-hydroxy-3-(3-methoxy-benzylamino)-propyl]-4-phenyl-butyramide;
- (2S)-2-(3(S)-Acetylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-Acetylamino-3-(-cyclopropylmethyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-(2(S)-amino-5-carboxypentanoylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-(2-methoxy-acetylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-propionylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-ethoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-methoxycarbonylamino-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-ethylureido-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-(3-hydroxypropionylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-(4-hydroxybutyrylamino)-3-((S)-sec-butyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-acetylamino-3-(isobutyl)-2-oxo-pyrrolidin-1-yl)-N-[(1S,2R)-1-benzyl-2-hydroxy-3-(3-methoxy-benzylamino)-propyl]-4-phenyl-butyramide;
- (2S)-2-(3(S)-acetylamino-3-((S)-sec-butyl)-2-oxo-pyrrolidin-1-yl)-N-[(1S,2R)-1-benzyl-2-hydroxy-3-(3-chloro-benzylamino)-propyl]-4-phenyl-butyramide;
- (2S)-2-(3(S)-acetylamino-3-((S)-sec-butyl)-2-oxo-pyrrolidin-1-yl)-N-[(1S,2R)-1-benzyl-2-hydroxy-3-(propargylamino)-propyl]-4-phenyl-butyramide;
- (2S)-2-(3(S)-acetylamino-3-((S)-sec-butyl)-2-oxo-pyrrolidin-1-yl)-N-[(1S,2R)-1-benzyl-2-hydroxy-3-(3,5-difluorobenzylamino)-propyl]-4-phenyl-butyramide;
- (2S)-2-(3(S)-acetylamino-3-((S)-sec-butyl)-2-oxo-pyrrolidin-1-yl)-N-[(1S,2R)-1-benzyl-2-hydroxy-3-((3-trifluoromethylbenzyl)amino)-propyl]-4-phenyl-butyramide;
- 2-(3(S)-Acetylamino-3(S)-isobutyl-2-oxo-pyrrolidin-1-yl)-N-[(1S,2R)-1-benzyl-2-hydroxy-3-benzylamino-propyl]-4-phenyl-butyramide;
- (2S)-2-(3(S)-acetylamino-3-((S)-sec-butyl)-2-oxo-pyrrolidin-1-yl)-N-[(1S,2R)-1-benzyl-2-hydroxy-3-(3-fluoro,5-(trifluoromethyl)benzylamino)-propyl]-4-phenyl-butyramide;
- 2-(3(S)-Acetylamino-3(S)-isobutyl-2-oxo-pyrrolidin-1-yl)-N-[(1S,2R)-1-benzyl-3-(2-cyano-ethylamino)-2-hydroxy-propyl]-4-phenyl-butyramide;
- (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(2-methoxyphenyl)-butyramide;
- (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3,4-methylenedioxyphenyl)-butyramide;
- (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-fluorophenyl)-butyramide;
- (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(4-fluorophenyl)-butyramide; and
- (2S)-2-(3(S)-acetylamino-3-(cyclopropylmethyl)-2-oxo-pyrrolidin-1-yl)-N-[(1S,2R)-1-(3,5-difluorobenzyl)-2-hydroxy-3-(3-methoxybenzylamino)-propyl]-4-(3-methoxyphenyl)-butyramide;

or a pharmaceutically acceptable salt thereof.

7. A pharmaceutical composition comprising a compound of claim 1 in association with a pharmaceutically acceptable carrier or diluent.

* * * * *